United States Patent
Miles

(10) Patent No.: US 9,012,719 B2
(45) Date of Patent: Apr. 21, 2015

(54) MODIFICATION OF MULTIDOMAIN ENZYME FOR EXPRESSION IN PLANTS

(75) Inventor: Stacy M. Miles, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 227 days.

(21) Appl. No.: 13/148,294

(22) PCT Filed: Feb. 4, 2010

(86) PCT No.: PCT/US2010/023149
§ 371 (c)(1),
(2), (4) Date: Oct. 20, 2011

(87) PCT Pub. No.: WO2010/091149
PCT Pub. Date: Aug. 12, 2010

(65) Prior Publication Data
US 2012/0030840 A1 Feb. 2, 2012

Related U.S. Application Data

(60) Provisional application No. 61/150,688, filed on Feb. 6, 2009, provisional application No. 61/180,153, filed on May 21, 2009.

(51) Int. Cl.
C12N 15/82 (2006.01)
C12N 9/42 (2006.01)
A01H 5/00 (2006.01)
C12N 9/34 (2006.01)

(52) U.S. Cl.
CPC .......... *C12N 15/8246* (2013.01); *C12N 9/2428* (2013.01); *C12Y 302/01091* (2013.01); *C12N 9/2437* (2013.01)

(58) Field of Classification Search
None
See application file for complete search history.

(56) References Cited

U.S. PATENT DOCUMENTS

| | | | | |
|---|---|---|---|---|
| 5,792,641 | A * | 8/1998 | Schulein et al. | 435/209 |
| 6,054,637 | A * | 4/2000 | Boller et al. | 800/298 |
| 6,747,137 | B1 * | 6/2004 | Weinstock et al. | 536/23.1 |
| 7,297,478 | B1 | 11/2007 | Reinl et al. | |
| 7,507,752 | B2 * | 3/2009 | He et al. | 514/317 |
| 8,237,014 | B2 * | 8/2012 | Blaylock et al. | 800/278 |
| 2006/0053514 | A1 * | 3/2006 | Wu et al. | 800/284 |

FOREIGN PATENT DOCUMENTS

| WO | 0116338 | 3/2001 |
|---|---|---|
| WO | 2008095033 | 8/2008 |

OTHER PUBLICATIONS

Gustavsson et al, 2001, Protein Engineering, 14:711-715.*
Arakane et al, 2003, Insect Biochem. & Mol. Bio., 33:631-648.*
Gustaysson et al, 2001, Protein Engineering, 14:711-715.*
Bothast et al, 2005, Appl. Micro. Biotech., 67:19-25.*
Hood et al, 2007, Plant Biotech. J., 5:709-719.*
Howard et al., "Identification and analysis of polyserine linker domains in prokaryotic proteins with emphasis on the marine bacterium *Microbulbifer degradans*", Protein Sci. (2004) 13, pp. 1422-1425.
Von Ossowski et al., "Protein Disorder: Conformational Distribution of the Flexible Linker in a Chimeric Double Cellulase" Biophysical Journal (2005) 88 pp. 2823-2832.
Shen et al., "Deletion of the Linker Connecting the Catalytic and Cellulose-binding Domains of Endoglucanase A (CenA) of *Cellulomonas fimi* Alters Its Conformation and Catalytic Activity", The Journal of Biological Chemistry (1991) No. 17, pp. 11335-11340, vol. 266.
Receveur et al., "Dimension, Shape, and Conformational Flexibility of a Two Domain Fungal Cellulase in Solution Probed by Small Angle X-ray Scattering", The Journal of Biological Chemistry (2002) vol. 277, No. 43, pp. 40887-40892.
Gustavsson et al., "Stable linker peptides for a cellulose-binding domain-lipase fusion protein expressed in *Pichia pastoris*", Protein Engineering (2001) vol. 14, No. 9, pp. 711-715.
Xu et al., "The O-Hyp glycosylation code in tobacco and *Arabidopsis* and a proposed role of Hyp—glycans in secretion", Phytochemistry (2008) 69 pp. 1631-1640.
Taylor et al., "Heterologous Expression of Glycosyl Hydrolases in planta: a new departure for biofuels", Trends Biotechnology, (2008) vol. 25, No. 8, pp. 413-424.
Doran, "Foreign protein degradation and instability in plants and plant tissue cultures", Trends in Biotechnology, (2006) vol. 24, No. 9 pp. 426-432.
Kavoosi et al., "Strategy for Selecting and Characterizing Linker Peptides for CBM9-Tagged Fusion Proteins Expressed in *Escherichia coli*", Biotechnology Bioengineering, (2007) vol. 98, No. 3, pp. 599-610.
Arai et al., "Design of the linkers which effectively separate domains of a bifunctional fusion protein", Protein Engineering, (2001) vol. 14, No. 8, pp. 529-532.

(Continued)

Primary Examiner — Ashwin Mehta
Assistant Examiner — Jason Deveau Rosen
(74) Attorney, Agent, or Firm — Dale Skalla

(57) ABSTRACT

Compositions and methods for expressing a multidomain enzyme in a plant are provided. The compositions include plants, seeds, plant tissues, and plant parts expressing a modified multidomain enzyme enzyme. The modified multidomain enzyme has a heterologous linker region that is not cleaved when the modified multidomain enzyme is expressed in a plant. In various embodiments, the linker region comprises the sequence set forth in SEQ ID NO:18, 19, or 20. Further provided are methods for producing a modified multidomain enzyme enzyme comprising cultivating plants expressing the modified multidomain enzyme. Downstream uses of transgenic plant material of the invention include agronomical and industrial uses, for example, human food, animal feed, pharmaceuticals, biofuel, industrial alcohol, fermentation feedstocks, and the like.

11 Claims, No Drawings

(56) References Cited

OTHER PUBLICATIONS

Ay et al., "Crystal Strucutre of a Phage Library-derived Single-chain Fv Fragment Complexed with Turkey Egg-white Lysozyme at 2.0 AÉ Resolution", Journal of Mol. Biol. (2000) 301, pp. 239-246.

Boer et al., "Characterization of *Trichoderma reesei* Cellobiohydrolase Cel7A Secreted From *Pichia pastoris* Using Two Different Promoters", Biotechnology and Bioengineering (2000) vol. 69, No. 5 pp. 486-494.

Francois et al., "Processing in transgenic *Arabidopsis thaliana* plants of polyproteins with linker peptide variants derived from the *Impatiens balsamina* antimicrobial polyprotein precursor" Plant Physiol. Biochem. (2002) 40 pp. 871-879.

Gomord et al., "Posttranslational modification of therapeutic proteins in plants" Plant Biology (2004) 7:171-181.

Ingeborg et al., "Factors influencing glycosylation of *Trichoderma reesei* cellulases. I: Postsecretorial changes of the O- and N-glycosylation pattern of Cel7A" Glycobiology (2004) vol. 14, No. 8 pp. 713-724.

Ingeborg et al., "Factors influencing glycosylation of *Trichoderma reesei* cellulases. II: N-glycosylation of Cel7A core protein isolated from difference strains" Glycobiology (2004) vol. 14, No. 8 pp. 725-737.

Jeoh et al., "Implications of cellobiohydrolase glycosylation for use in biomass conversion" Biotechnology for Biofuels (2008) vol. 1, No. 10 pp. 1-12.

Karnoup et al., "O-Linked glycosylation in maize-expressed human IgA1" Glycoibology (2005) vol. 15, No. 10 pp. 965-981.

Lin et al., "Role of the linker region in the expression of *Rhizopus oryzae* glucoamylase" BMC Biochemistry (2007) vol. 8, No. 9 pp. 1-13.

Saint-Jore-Dupas et al., "From planta to pharma with glycosylation in the toolbox" TRENDS in Biotechnology (2007) vol. 25, No. 7, pp. 317-323.

Showalter, "Arabinogalactan-proteins: structure, expression and function" CMLS Cellular and Molecular Life Sciences (2001) 58 pp. 1399-1417.

Shpak et al., "Synthetic genes for glycoprotein design and the elucidation of hydroxyproline-O-glycosylation codes" PNAS (1999) vol. 96, No. 26 pp. 14736-14741.

Tan et al., "Glycosylation Motifs That Direct Arabinogalactan Addition to Arabinogalactan-Proteins1" Plant Physiology (2003) 132 pp. 1362-1369.

* cited by examiner

MODIFICATION OF MULTIDOMAIN ENZYME FOR EXPRESSION IN PLANTS

REFERENCE TO SEQUENCE LISTING SUBMITTED ELECTRONICALLY

The official copy of the sequence listing is submitted electronically via EFS-Web as an ASCII formatted sequence listing with a file named "72196WO Sequence Listing.txt", created on Jan. 13, 2010, and having a size of 95 kilobytes and is filed concurrently with the specification. The sequence listing contained in this ASCII formatted document is part of the specification and is herein incorporated by reference in its entirety.

FIELD OF THE INVENTION

This invention relates to plant molecular biology, particularly to methods and compositions for increasing expression and/or activity of a protein in a plant.

BACKGROUND OF THE INVENTION

A number of heterologous expression systems have been devised over the last decade for the production of clinically and agronomically useful recombinant proteins. A significant challenge in most systems is to optimize the yield and quality of the recombinant protein product. Significant progress has been achieved over the last 15 years in the optimization of transgene transcription and translation in plants (Potenza et al., 2004, *In Vitro Cell. Dev. Biol.-Plant*, 40, 1-22; Streatfield, 2007, *Plant Biotechnol. J.* 5, 2-15) and the elucidation and modulation of the complex protein post-translational modifications characteristic of the plant cell machinery (Gomord and Faye, 2004, *Curr. Opin. Plant Biol.* 7, 171-181; Faye et al., 2005, *Vaccine* 23, 1770-1778). Despite these advances, ensuring satisfactory yield and quality of recombinant proteins often remains a difficult task.

One factor strongly influencing recombinant protein quality and yield is the relative inherent stability of polypeptide chains expressed in a heterologous environment (Faye et al., 2005).

Proteolytic enzymes, or proteases, contribute to the overall control of metabolic and transduction pathways by directing the activation or hydrolysis of proteins implicated in key regulatory processes, or by contributing to the elimination of misfolded proteins and the selective recycling of amino acids from short-lived proteins (Vierstra, 2003, *Trends Plant Sci.* 8, 135-142; Schaller, 2004, *Planta*, 220, 183-197). In plants, these enzymes also initiate the general recycling of proteins in senescing organs and the mobilization of amino acid constituents of seed or tuber storage proteins during germination (Müntz, 2007, *J. Exp. Bot.* 58, 2391-2407).

Proteases may affect the integrity of recombinant proteins in different ways, both in planta during protein expression and ex planta during extraction and subsequent downstream processing (Michaud et al., 1998, *Methods Biotechnol.* 3, 177-188; Rivard et al., 2006, *Plant Biotechnol. J.* 4, 359-368). Depending on the number of "susceptible" cleavage sites accessible to endogenous proteases for peptide bond hydrolysis, the protein may undergo complete hydrolysis directly impacting on its final yield or partial trimming, altering the activity or homogeneity of the final protein product. Although interesting yields may be obtained in terms of net protein levels, the final product may show altered integrity, structural heterogeneity and/or deficient biological activity, potentially altering its value for commercialization (Faye et al., 2005).

SUMMARY OF THE INVENTION

Compositions and methods for expressing modified multidomain enzymes in a plant are provided. The compositions comprise plants, seeds, plant tissues, and plant parts expressing a modified multidomain enzyme, wherein the multidomain enzyme is composed of at least a first domain, at least a first linker sequence, and at least a second domain. The modified multidomain comprises a heterologous linker region that is not cleaved when the modified multidomain enzyme is expressed in a plant. Further provided are methods for producing a modified multidomain enzyme comprising cultivating plants expressing the modified multidomain enzyme.

Downstream uses of transgenic plants or plant material comprising the expression constructs of the invention include agronomical, pharmaceutical, and industrial uses, for example, human food, animal feed, biofuel, industrial alcohol, fermentation feedstocks, and the like.

DETAILED DESCRIPTION OF THE INVENTION

Overview

The present invention is directed to the use of plants for transgenic expression of multidomain enzymes. Higher plants are particularly useful for heterologous protein production since plants are amenable to large-scale production, they do not require aseptic conditions like bacterial recombinant protein production systems, and the levels of transgene-encoded proteins in plants may exceed 1% of the total protein content. To date, several proteins of commercial interest have been expressed successfully in plants, including a variety of antibodies, vaccine antigens, protein allergens, enzymes and enzyme inhibitors, coagulation factors, cytokines and hormones. However, expressing high levels of stable and functional proteins remains the bottleneck of many scientific and biotechnological endeavors including producing proteins for agricultural and therapeutic purposes Thus, provided herein are methods and compositions for improving expression, stability, and/or activity of a multidomain enzyme in a plant cell. The methods comprise introducing into the plant cell a nucleic acid construct comprising a modified multidomain enzyme, wherein a native linker sequence in said multidomain enzyme has been replaced with a heterologous linker sequence that is not cleaved by a plant protease. By "heterologous" linker sequence is intended as linker sequence that is not native (i.e., does not naturally occur in the wild-type sequence) to the enzyme being modified. The linker sequence can be derived from a different species or organism, or may be a synthetic linker sequence (i.e., not existing in nature in any organism) or may be the native linker sequence modified. Linker regions that are not cleaved by plant proteases is not intended to be limited to the production of a single polypeptide by a host plant but is intended to refer to a preference for producing full length polypeptide as compared to the range of polypeptides produced when the linker region of the multidomain enzyme is the native sequence.

The modified multidomain enzyme is composed of at least one first domain, at least one heterologous linker, and at least one second domain. The first domain and the second domain are non-heterologous sequences. By "non-heterologous" it is intended that the first domain and the second domain are derived from the same native multidomain enzyme and may contain minor modifications which result in a domain polypeptide sequence which is greater than 80% identical, greater than 85% identical, greater than 90% identical, greater than 95% identical, greater than 96% identical, greater than 97% identical, greater than 98% identical, or greater than 99% identical to the native polypeptide sequence.

In various embodiments, the nucleic acid constructs encoding the modified multidomain enzymes described herein result in an increased expression, stability and/or activity of the enzyme in the plant cell when compared to a control nucleic acid construct. An increase in expression, stability, or activity refers to an increase in a measurable amount of an enzymatically-active enzyme. The stability of an enzyme may also relate to its conformational stability, which is reflected in the enzyme's three-dimensional structure, or its chemical stability, which refers to the chemical composition of the enzyme's constituent amino acids.

It is recognized that polypeptides synthesized in heterologous systems can be produced in a range of sizes. A percentage of the produced polypeptide can be the full length enzyme which is defined as the polypeptide resulting from the translation of the coding sequence in its entirety; however, smaller polypeptides or larger polypeptides can also be produced. Smaller polypeptides may be the result of processing of the polypeptide by proteolytic processing of the polypeptide while larger polypeptides may be the result of the addition of carbohydrates to the polypeptide. The instant application describes a method for producing multidomain proteins in a plant host wherein the amount of full length polypeptide produced is greater when compared to the amount of full length polypeptide produced when the multidomain enzyme contains the native linker. Replacement of the native linker with heterologous linkers that are resistant to cleavage by plant proteases will lead to a greater amount of full length multidomain enzyme produced by the plant host.

While not bound by any particular theory or mechanism, the increase may result from an increase in translation or a decrease in degradation of the enzyme, and/or an increase in the catalytic activity of the enzyme. In another embodiment, the increase relates to an increase in the expression, stability, and/or activity of a full-length multidomain enzyme. For the purposes of the present invention, a full-length multidomain enzyme refers to a multidomain enzyme comprising at least a functional binding domain, a linker, and a functional catalytic domain. A modified protein having a "functional binding domain" is a protein in which the binding properties are substantially similar to, or improved relative to, the binding, properties of the native protein in its native environment. Likewise, a modified protein having a "functional catalytic domain" is a protein in which the catalytic properties are substantially similar to, or improved relative to, the catalytic properties of the native protein in its native environment. By "substantially similar" is intended at least about 80% or more of the binding properties or catalytic properties of the native protein. One of skill in the art will recognize that deletion of one or a few amino acids of any particular multidomain protein may have no significant effect on the stability or activity of the protein.

In one embodiment, the increase in expression, amount of full length polypeptide, stability, and/or activity is at least about 10%, at least about 20%, at least about 30%, at least about 40%, at least about 50%, at least about 60%, at least about 70%, at least about 80%, at least about 90%, at least about 2-fold, at least about 3-fold, at least about 4-fold, at least about 5-fold, at least about 6-fold, at least about 7-fold, at least about 10-fold, at least about 20-fold, or greater when compared to a control. By "control" nucleic acid construct is intended a nucleic acid construct comprising a nucleotide sequence encoding a multidomain enzyme having a native linker sequence; or a linker sequence known to be cleaved by a plant protease. Unless otherwise specified, the control construct comprises a nucleic acid encoding a multidomain enzyme with a native linker sequence. A "native linker sequence" refers to the linker sequence present in the multidomain sequence in the organism from which the multidomain sequence was derived (i.e. the naturally-occurring linker sequence).

Thus, the methods of the invention find particular use in the integration of current practices for the cultivation of crop plants for the purpose of obtaining a commercially desired plant material with increased expression, stability and/or activity eta multidomain enzyme, and the use of the crop plant residues as a source of biomass for the production of fermentable sugars, or for agricultural, pharmaceutical, and/or human consumption.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, oats, tobacco, *Miscanthus* grass, Switch grass, trees, beans in general, rape/canola, alfalfa, flax, sunflower, safflower, millet, rye, sugarcane, sugar beet, cocoa, tea, Brassica, cotton, coffee, sweet potato, flax, peanut, clover; vegetables such as lettuce, tomato, cucurbits, cassava, potato, carrot, radish, pea, lentils, cabbage, cauliflower, broccoli. Brussels sprouts, peppers, and pineapple; tree fruits such as citrus, apples, pears, peaches, apricots, walnuts, avocado, banana, and coconut; and flowers such as orchids, carnations and roses.

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, withers, and the like.

In one embodiment, the plant is an indeterminate plat. These varieties grow vegetatively for indefinite periods in temperate regions. These varieties can be engineered to accumulate the polypeptide of interest in the vacuoles and can be grown until the first frost. At that time, the plant could be allowed to dessicate, harvested dry, and used for food, livestock feed, or in biomass conversion or other commercially-useful processes.

As used herein, "biomass" or "feedstock" refers to useful biological material including a product of interest, which material is to be collected and is intended for further processing to isolate or concentrate the product of interest. The biomass or feedstock may comprise the fruit or parts of it or seeds, leaves, or stems or roots where these are the parts of the plant that are of particular interest for the industrial purpose. "Biomass", as it, refers to plant material, includes any structure or structures of a plant that contain or represent the product of interest.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs. A sequence is also isolated if separated from the chromosome and cell in which it naturally occurs in but inserted into a genetic context, chromosome, or cell in which it does not naturally occur.

Multidomain Enzymes

The methods of the present invention encompass modified multidomain enzymes. A "multidomain enzyme" or a "multidomain protein" refers to any protein containing two or more domains. The domains may be on single polypeptide; they may also be on different polypeptides. Domains are generally regarded as compact, semi-independent units (Richardson (1981) Advan. Protein Chem. 34:167-339) that could fold autonomously Wetlaufer (1973) Proc. Natl Acad. Sci. 70:697-701). Exemplary domains include an immunoglobulin superfamily constant domain such as a CH2 or CH3 domain, a receptor binding domain, a ligand binding domain, an enzymatic or catalytic domain, a fibronectin domain, a dockerin domain, and the like.

In various embodiments, the multidomain enzymes encompassed herein comprise at least a first domain, at least a first linker, and at least a second domain. In some embodiments, the multidomain enzyme comprises at least a first binding domain, at least a first linker, and at least a first catalytic domain. A binding domain is a noncatalytic domain involved in substrate binding or specific protein interactions. Upon binding, proteins may undergo a conformational change. Thus, these binding domains are essential for the function of many proteins. The term "catalytic domain" is defined herein as a structural portion or region of the amino acid sequence of the multidomain enzyme that possesses the catalytic activity of the enzyme. A "linker" is defined as the region connecting two domains. A connection between domains may play an important structural role in positioning domains with respect to one another, or the connection may merely tether two domains within a certain distance of one another. The linker region may also comprise sites for proteolytic cleavage. The linker region of multidomain enzymes is typically three dimensionally a linear region which is a flexible hinge connecting two domains together.

Numerous proteins of higher organisms have a multidomain architecture consisting of strings of mobile modules (Doolittle (1995) Annu Rev Biochem. 64:287-114). Many of the modules identified so far have defined binding and/or catalytic functions (i.e., binding domains or catalytic domains), but some may just act as simple spacer elements required only to arrange binding surfaces in space (i.e., linker regions).

A variety of software applications for protein structure prediction, including domain recognition and linker sequence predictions, are described in Lobley (2009) Bioinformatics Advance Access Online, May 7, 2009; Bryson (2005) Nucl. Acids Res. 33 (Web server issue):W36-38; Jones (1999) J. Mol. Biol. 292: 195-202; McGruffin and Jones (2003) Bioinformatics 19:8740881; Jones (1999) J. Mol. Biol 287: 797-815; Jones (2007) Bioinformatics 23: 538-544; Jones et al (1994) Biochem. 33: 3038-3049; Ebina et al. (2009) Biopolymers 92(1):1-8, and several programs are available on the internet, for example, at tuat.ac.jp/~domserv/cgi-bin/DLP-SVM.cgi; at predictprotein.org/about.html; and at bioinf.cs.ucl.ac.uk/psipred/index.html#more.

Linkers

Provided herein are methods and compositions for improving expression, stability, and/or activity of a multidomain enzyme in a plant cell. The methods comprise introducing into the plant cell a nucleic acid construct comprising a modified multidomain enzyme, wherein a native linker sequence in the modified multidomain enzyme has been replaced with a heterologous linker sequence that is not cleaved by a plant protease. The heterologous linker sequence may be resistant to cleavage by a plant protease due to the replacement of protease sensitive sites with protease insensitive sites or by altering the structural conformation of the multidomain enzyme such that protease-sensitive sites are inaccessible to the plant proteases. A "protease sensitive" site is an amino acid residue or sequence that is recognized by and cleaved by a particular plain protease. As discussed supra, enzymes susceptible to protease cleavage may undergo complete hydrolysis, directly impacting its final yield, or may undergo partial trimming thereby altering the activity or homogeneity of the final protein product. Thus, replacement of native linker sequences with heterologous linker sequences in a multidomain protein may result in improvement in the integrity, structural heterogeneity and/or biological activity of the enzyme.

The linker sequences front different enzymes rarely share any apparent sequence homology but their amino acid composition is typically rich in proline and hydroxyl amino acids (Gilkes et al, (1991) Microbiol. Rev. S5, 303-315; and Claeyssens and Tomme (1989) in *Tkichalenna reesei* Cellulases: Biochemistry, Genetics, Physiology and Application (Kubicek, C. P., Eveleigh, D. E., Esterbauer, H., Steiner, W., and Kubicek-Pranz, E. M., eds) pp. 1-11, Proceedings, Tricell (1989) Royal Society of Chemistry)). In general, a linker may be between about 5 to 60 amino acid residues, between about 15 to 50 amino acid residues, and between about 25 to 45 amino acid residues. See, for example. Srisodsuk et al., 1993, J. Biol. Chem. 268(28): 20756-20761 (herein incorporated by reference in its entirety) for a discussion of the linker peptide of *T. reesei* CBHI.

In one embodiment of the present invention, the native linker sequence is replaced by a linker sequence derived from a fungal organism or from a bacterium. While not bound by any particular theory or mechanism, linker sequences derived from bacterial or fungal organisms may be less susceptible to cleavage by plant enzymes. By "derived from" is intended that the heterologous linker sequence is identified in a protein expressed by the organism and utilized as a linker sequence in the modified multidomain enzyme encompassed herein. The native linker sequence in the modified multidomain enzyme may be replaced with a linker sequence that is identical to the linker sequence identified in the fungal or bacterial protein, or may be modified further to improve the functionality of the linker sequence in a plant (including, but not limited to, using plant-preferred codons to improve expression of the modified enzyme in the plant and/or replacing one or more plant protease-sensitive sites with plant protease-insensitive sites).

In another embodiment, methods for improving the expression, stability, and/or activity of the multidomain enzyme comprise replacement of one or more cleavage-sensitive residues within the linker region with one or more residues comprising a glycosylation site sequence, or by adding one or more glycosylation site sequences. The role of glycosylation in many multidomain enzymes includes providing sufficient spatial separation between the catalytic core and binding domains, and protecting the linker peptide against proteolysis (Srisodsuk et al., 1993. J. Biol. Chem., 268, 20756-20761; Clarke, 1997, Biodegradation of cellulose. In Enzymology and biotechnology. Technomic Publishing, Pennsylvania, p. 55). Thus, while not being bound by any particular theory or mechanism, of the linker region of multidomain enzymes to increase glycosylation may prevent proteolytic degradation of the modified multidomain enzyme by plant enzymes.

In one embodiment, the heterologous linker region comprises one or more N-linked glycosylation sites. An "N-linked glycosylation" site comprises an amino acid residue or sequence that is susceptible to N-linked glycosylation. In various embodiments, the heterologous linker comprises one or more N-linked glycosylation consensus sequences, including one or more Asn-X-Ser/Thr/Cys sequences where X is any amino acid except proline.

Alternatively, or in addition, the heterologous linker region comprises one or more O-finked glycosylation sites. An "O-linked glycosylation site" comprises an amino acid residue or sequence that is susceptible to O-linked glycosylation. To date, a consensus primary amino acid sequence for O-glycosylation has not been identified, however, different structural motifs have been proposed (see, for example. Young, et al., 1979, Biochemistry. 18(20):4444-4448, Muller et al., 1997, J Biol. Chem. 272(40):24780-24793; Yoshida et al., 1997, J Biol Chem, 272(27):16884-16888; Gooley et al. (1991) Biochem Biophys Res Commun. 178(3):1194-1201; and Christlet Veluraja (2001) Biophys. J. 80(2): 952-960, each of which is herein incorporated by reference in its entirety). Thus, in various embodiments, the heterologous linker region comprises one or more O-linked glycosylation structural motifs, including but not limited to one or more of Thr-Ala-Pro-Pro, Thr-Val-X-Pro, Ser/Thr-Pro-X-Pro, and Thr-Ser-Ala-Pro.

Alternatively, the heterologous linker sequence may be derived from the linker sequence of a glycosylated protein, including a plant glycoprotein. The sequences of a number of glycosylated proteins have been published in recent years. SWISSPROT, PIR, PROSITE, PDB, EMBL, HSSP, LISTA, and MIM databases contain glycosylated protein entries. Many O-linked glycosylated proteins are listed in the O-GLY-CBASE database (Gupta et al, (1999) Nucleic Acids Research 27:370-372).

In yet another embodiment, the native linker region of a multidomain enzyme may be replaced with all or part of the transmembrane domain of a transmembrane protein. Certain membrane proteins are "transmembrane proteins" and have an extracellular domain, which interacts with the external cellular environment, an intracellular domain, which interacts with the internal cellular environment, and a transmembrane domain which traverses the cellular lipid bilayer, "Transmembrane domain," which comprises the "transmembrane regions," refers to the domain of transmembrane proteins that lies within the plasma membrane, and may also include the corresponding cytoplasmic (intracellular) and extracellular loops. Thus all or substantially all of the transmembrane region of a transmembrane protein can be used as a linker sequence in a multidomain enzyme. The TMPDB database of transmembrane proteins is described in (Ikeda et al. (2003) Nucleic Acids Res. 31, 406-409) The Protein Data Bank of Transmembrane Proteins (PDBTM) is described in Tusnády et al, (2004) Bioinformatics 20(17):2964-72 and Tusnády et al, (2005) Nucleic Acids Res. 33(Database issue): D275-8.

The expression, stability, and/or activity of a multidomain enzyme may also be improved by removal of protease cleavage sites within the linker sequences. A variety of plant proteases and their target cleavage site sequences are known in the art.

Modified multidomain enzymes may be generated by replacement of native linker regions with linker regions derived from other proteins, or may be generated by mutagenesis approaches. In one embodiment, site-directed or random mutagenesis is used to modify one or more sues within a linker sequence to generate a linker that is less sensitive to protease cleavage. In another embodiment, directed evolution approaches are used to improve the linker regions. In the past several years, directed evolution has emerged as an alternative approach to rational design, enabling the improvement of structural and functional properties, such as stability and performance under different conditions, or changes in their reaction and substrate specificity (Tao and Cornish (2002) Curr Opin Chem Biol 6:858-864). Rather than designing a limited number of site-directed mutants, directed evolution implements an iterative Darwinian optimization process, whereby the fittest variants are selected from an ensemble of random mutations. Improved variants are identified by screening or selection for the properties of interest and then encoding genes are then used as parent genes for the following round of evolution (Roodveldt et al, (2005) Current Opinion in Structural Biology 15(1):50-56).

Screening or selecting for improved variants can be done in two ways: screening or selecting for the protein's own function or screening or selecting for the activity of a reporter protein. Screening or selecting for the protein's own function will vary according to the activity of the multidomain protein being evaluated. Methods for screening or selecting for the activity of a reporter protein are known in the art. See, for example, U.S. Patent Publication 20090092982, which describes a method which couples the folding status and/or stability of the protein (or variant of a protein) to a screenable (e.g., selectable) phenotype imparted by a separate entity (e.g., antibiotic resistance). This screenable phenotype is used to assess stability.

Cellulase

In various embodiments of the present invention, the modified multidomain enzyme is a cellulose-degrading, enzyme. Plants are an abundant source of cellulosic substrate, therefore, expression of cellulose-degrading enzymes within the cellulosic feedstock will minimize or eliminate the need for exogenous addition of enzyme. Thus, provided herein are nucleotide sequences encoding a modified cellulose enzyme. For the purposes of the present invention, a "cellulase" is an enzyme that is capable of catalyzing the hydrolysis of a 1-4-beta-D-glycosidic linkage, and is composed of at least one catalytic domain and at least one other domain selected from the group consisting of a catalytic domain and cellulose binding domain. The structure of many cellulases is described in Gilkes et al. (1991) Microbiological Reviews 55(4303-315, which is herein incorporated by reference in its entirety. Cellulose degradation processes using transgenic biomass produced according to the present invention can be carried out more inexpensively, easily, and more environmentally safe than can conventional methods.

The modified cellulase enzymes encompassed herein have a linker sequence that results in less cleavage when the modified cellulase is expressed in plants. In some embodiments, less than about 90% of the modified enzyme is cleaved when expressed in plants, less than about 80%, less than about 70%, less than about 60%, less than about 50%, less than about 40%, less than about 30%, less than about 20%, less than about 10%, less than about 5%, or none of the modified enzyme is cleaved when expressed in plants. The heterologous linker sequence may result in less cleavage due to the replacement or protection of protease-sensitive cleavage sites as discussed supra. Thus, the modified cellulase encompassed herein has improved expression, stability, and/or activity relative to a control cellulase.

In various embodiments, replacement of one or more native linker sequences with an improved linker sequence results in an increase in the expression, stability, and/or activity of the full-length cellulase enzyme. This full-length enzyme comprises at least one binding domain, at least one heterologous linker, and at least one catalytic domain. A particular advantage of this full-length protein is the retention of the binding domain, particularly the cellulose-binding domain. While not bound by any particular theory or mechanism, the presence of the cellulose-binding domain in the modified cellulase may result in an improvement in hydrolysis of insoluble cellulosic substrates, such as crystalline cellulose.

In some embodiments, the native linker sequence corresponding to amino acid residues 471 through 499 of SEQ ID NO:2 is replaced with a heterologous linker sequence. Alternatively, a native linker sequence in a cellulose homologous to SEQ. ID NO:2 is replaced with a heterologous linker sequence. It will be understood that the native linker region of homologous cellulose sequences may be 1, 2, 3, 4, 5, 6, 7, 8, 9, 10, 11, 12, 13, 14, 15, 16, 17, 18, 19, 20, or more amino acids shorter or longer than the linker region defined by amino acid residues 471 through 499 of SEQ ID NO:2.

In various embodiments of the present invention, the nucleotide sequence encodes a cellulase comprising the linker sequence set forth in SEQ ID NO:18, 19, or 20. Based on this information, as well as detailed information in the art regarding the structural features of cellulose enzymes, additional heterologous linker sequences can be designed and tested for expression in plant cells. Methods for monitoring expression, processing (including cleavage), and activity of cellulase enzymes are known in the art.

In one embodiment, the modified multidomain enzyme is a cellobiohydrolase enzyme or an endoglucanase enzyme. Cellobiohydrolases and endoglucanases are structurally similar and are frequently composed of multiple domains. At least one of the domains is a catalytic core domain which may be associated with additional catalytic domains or at least one cellulose-binding domain (CBD). The two domains are connected by relatively long, glycosylated linker peptides of 6-59 amino acids.

The term "cellobiohydrolase" (CBH) refers to a group of cellulase enzymes classified as EC 3.2.1.91. These enzymes are also known as exoglucanases or exo-cellobiohydrolases. CBH enzymes have been isolated from a variety of sources, microbial sources such as bacteria, yeast, and fungi, each of which is encompassed herein. In various embodiments, the CBH enzyme is a modified cellobiohydrolase I (CBHI) enzyme. CBHI plays a key role in the decomposition of crystalline cellulose (Claeyssens et al. (1990) Biochem J 270 (1):251-256; and Wood et al. (1989) Biochem J 260(1):37-44). In general, a CBHI type enzyme preferentially hydrolyzes cellobiose from the reducing end of cellulose and a cellobiohydrolase II (CBH2) type enzyme preferentially hydrolyzes the non-reducing end of cellulose.

Endoglucanases (1,4-p-D-glucan glucanohydrolase; EC 3.2.1.4) are ubiquitous enzymes that hydrolyze 1,4-β linkages adjacent to unsubstituted glucose residues (Henrissat et al. (1989) Gene 81:83-95), are produced by a broad range of organisms, including fungi, bacteria, plants, and insects.

Glucoamylase

In various embodiments of the present invention, the modified multidomain enzyme is a starch-degrading enzyme. Starch-degrading enzymes are widely distributed throughout many species of animals, plants and microorganisms. These enzymes have been classified as alpha-amylases and glucoamylases belonging to glycoside hydrolase families 13, 14 or 15. In various embodiments, the present invention encompasses a modified glucoamylase enzyme. Glucoamylases (alpha-1,4-glucan glucohydrolases E.C.3.2.1.3) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylase and amylopectin). Commercially glucoamylases are very important enzymes that have been used in a wide variety of applications requiring the hydrolysis of starch. Glucoamylases can be provided through the heterologous expression of glucoamylase in at least one variety in the harvested plant material of the invention.

Similar to other polysaccharide-degrading enzymes die majority of glucoamylases have a modular structure consisting of a catalytic domain, a starch-binding domain, and a highly O-glycosylated linker that connects the two domains (Bourne and Henrissat (2001) Curr. Opin. Struct. Biol, 11(5): 593-600; Sauer et al. (2000) Biochim. Biophys, Acta. 1543 (2): 275-293), A description of the catalytic site, mechanism of action, substrate recognition, the linker region, and multidomain architecture of this class of enzymes can be found in Sauer et al. (2000) Biochim. Biophys. Acta. 1543(2): 275-293, which is herein incorporated by reference in its entirety.

The modified glucoamylase enzymes encompassed herein have a linker sequence that results in less cleavage when the modified glucoamylase is expressed in plants. In some embodiments, less than about 90% of the modified enzyme is cleaved when expressed in plants, less than about 80%, less than about 70%, less than about 60%, less than about 50%, less than about 40%, less than about 30%, less than about 20%, less than about 10%, less than about 5%, or none of the modified enzyme is cleaved when expressed in plants. The heterologous linker sequence may result in less cleavage due to the replacement or protection of protease-sensitive cleavage sites as discussed supra. In various embodiments of the present invention, the modified glucoamylase comprises the linker sequence set forth in SEQ ID NO: 18, 19, or 20. Thus, the modified glucoamylase encompassed herein has improved expression, stability, and/or activity relative to a control glucoamylase.

Plant Expression Cassettes

The compositions of the invention also comprise nucleic acid sequences for transformation and expression of a multidomain enzyme in a plant cell of interest. The nucleic acid sequences may be present in DNA constructs or expression cassettes, "Expression cassette" as used herein means a nucleic acid molecule capable of directing expression of a particular nucleotide sequence in an appropriate host cell, comprising a promoter operatively linked to the nucleotide sequence of interest (i.e., a nucleotide sequence encoding a polypeptide of interest) which is operatively linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette May be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of directing expression of a multidomain enzyme in a plant cell. The expression cassette will include in the 5'-3' direction of transcription, a transcriptional and translational initiation region (i.e., a promoter) and a polynucleotide encoding the modified multidomain enzyme. The expression cassette may optionally comprise a transcriptional and translational termination region (i.e. termination region) functional in plants.

In addition, the construct may further comprise additional regulatory elements to facilitate transcription, translation, or transport of the modified multidomain enzyme. The regulatory sequences of the expression construct are operably linked to the polynucleotide encoding the modified multidomain enzyme. By "operably linked" is intended a functional linkage between a regulatory element and a second sequence wherein the regulatory element initiates and/or mediates transcription, translation, or translocation of the DNA sequence corresponding to the second sequence. Generally, operably linked means that the nucleotide sequences being linked are contiguous. The regulatory elements include promoters, enhances, and signal sequences useful for targeting cytoplasmically-synthesized proteins to the endomembrane system of the plant cell.

The expressed multidomain enzymes may also be targeted to certain organelles such as vacuoles to alleviate toxicity problems. For vacuole-targeted expression of multidomain enzymes, plants are transformed with vectors that include a vacuolar targeting sequence such as that from a tobacco chitinase gene. In this case, the expressed multidomain enzyme will be stored in the vacuoles where they will not be able to degrade cellulose and harm the plant in one embodiment of the present invention, the vacuole sorting signal sequence is derived from the barley polyamino oxidase 2 (BPAO2) signal sequence. BPAO2 has an N-terminal signal peptide for entry into the secretory pathway. The presence of a C-terminal extension of this signal peptide results in vacuolar localization of BPAO in a plant cell (see Cervelli et al. (2004) The Plant Journal 40:410-418). In another embodiment, useful vacuole sorting, signals are described in U.S. application Ser. No. 12/359,421, which is herein incorporated by reference in its entirety.

In various embodiments of the present invention, modified multidomain enzyme coding sequences are fused to promoters active in plants and transformed into the nuclear genome or the plastid genome. Chloroplast expression has the advantage that the multidomain enzyme is less damaging to the plastid as it contains little or no cellulose.

In other embodiments, the construct comprises, in the 5' to 3' direction of transcription, a transcriptional and translational initiation region (i.e., a promoter), a polynucleotide encoding an endoplastic reticulum signal sequence, and a polynucleotide encoding the modified multidomain enzyme. Exemplar signal sequences include the SEKDEL (SEQ ID NO:23) endoplasmic reticulum targeting sequence, the gamma zein 27 kD signal sequence, and the *Glycine max* glycinin GY1 signal sequence. Others useful in the methods of the invention will be apparent to one of skill in the art.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally mewing multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Promoters active in photosynthetic tissue in order to drive transcription in green tissues such as leaves and stems are also of interest for the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al, (1994) Plant Cell Physiol, 35:773-778), the Cab-1 gene promoter from wheat (Fejes et al. (1990) Plain Mol. Biol. 15:921-932), the CAB-1 promoter from spinach (Lubberstedt et al. (1994) Plant Physiol, 104:997-1006), the cab1R promoter front rice (Luan et al. (1992) Plant Cell 4:971-981), the pyruvate orthophosphate dikinase (PPDK) promoter from corn t Matsuoka et al, (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346, herein incorporated by reference in its entirety.

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a green tissue-specific manner in transgenic plants.

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought. With a chemically inducible promoter, expression of the multidomain enzyme genes transformed into plants may be activated at an appropriate time by foliar application of a chemical inducer.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest may be native with the plant host, or may be derived from another source (i.e., foreign or heterologous to the promoter, the DNA sequence of interest, the plant host or any combination thereof). Appropriate transcriptional terminators are those that are known w function in plants and include the CAMV 35S terminator, the mil terminator, the nopaline synthase terminator and the pea rbcs E9 terminator. These can be used in both monocotyledons and dicotyledons. In addition, a gene's native transcription terminator may be used.

In some embodiments, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picomavirus leaders, for example, EMCV leader (Encephalomyocarditis 5' noncoding region) (Elroy-Stein, O., Fuerst T. R., and Moss, B. PNAS USA 86:6126-6130 (1989)); potyvirus leaders, for example, TEV leader (Tobacco Etch Virus) (Allison et. al., 198); MDMV leader (Maize Dwarf Mosaic Virus); Virology 154: 9-20 human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallic, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et at, Plant Physiology 84:965-968 (1987).

It will also be recognized that the nucleotide sequence encoding the modified multidomain enzyme may be optimized for increased expression in the transformed host cell. That is, the nucleotide sequences can be synthesized using host cell-preferred codons for improved expression, or may be synthesized using codons at a host-preferred codon usage frequency. Generally, the GC content of the gene will be increased. See, for example, Campbell and Gowri (1990) Plant Physiol. 92:1-11 for a discussion of host-preferred codon usage. Methods are available in the art for synthesizing plant-preferred genes. Sec, for example, U.S. Pat. Nos. 5,380, 831, and 5,436,391, and Murray et at (1989) Nucleic Acids Res. 17:477-498, herein incorporated by reference.

Plants

Plants useful in the present invention include plants that are transgenic for the modified multidomain enzyme. One of skill in the art will recognize that plants may express one or more additional polypeptide sequences associated with or contributing to one or more secondary trains) of interest. These polypeptides may be cytoplasmically-expressed, may be targeted to a subcellular organelle, or may be secreted by the plant cell. Secondary traits of interest include agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. A secondary trait of interest may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). A plethora of genes useful for generating plants with desired secondary traits are available in the art.

The type of plant selected depends on a variety of factors, including for example, the downstream use of the harvested plant material, amenability of the plant species to transformation and the conditions wider which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

It is further contemplated that the constructs of the invention may be introduced into plant varieties having improved properties suitable or optimal for a particular downstream use.

For example, naturally-occurring genetic variability in plants with altered starch metabolism is useful in the methods of the invention. Many such plants carry mutations in genes encoding isoforms of starch synthesis or starch degradation enzymes. For example, plants have been identified which are heterozygous or homozygous for one or more of the waxy (wx), amylose extender (ae); dull (du), horny (h), shrunken (sh), brittle (bt), floury (fl), opaque (o), or sugary (su) mutant alleles. See, for example, U.S. Pat. Nos. 4,428,972; 4,767, 849; 4,774,328; 4,789,738; 4,789,557; 4,790,997; 4,792,458; 4,798,735; and 4,801,470, herein incorporated by reference. These plants can be used in their native form, or can be modified to exhibit one or more additional traits of interest.

For plants with increased nutritional quality, several varieties of corn are available, such as those with increased lysine (Crow's Hybrid Corn Company, Milford, Ill.), protein (BASF) and oil (Pfister Hybrid Corn Company, El Paso, Ill. under the trademark KERNOIL®) levels. Other suitable high oil corn includes the corn populations known as Illinois High Oil (IHO) and Alexander High Oil (Alexo); samples of which are available from the University of Illinois Maize Genetics Cooperative—Stock Center (Urbana, Ill.).

Sweet corn is also available in which there is a reduction in the amount of starch and an increase in the amount of glucose, sucrose and/or water soluble polysaccharides normally found in the immature corn kernel (Creech, R. and Alexander, D. E. In Maize Breeding and Genetics; D. B. Walden, Ed.; John Wiley and Sons: New York, 1978; pp. 249-264). In several plant species such as corn (Shannon & Garwood, 1984), pea (Bhattacharyya et al, 1990), potato (Hovenkamp-Hermelink et al., 1987), *Arabidopsis* (Caspar et al., 1985; Lin et al., 1988a; Lin et al., 1988b) and tobacco (Hanson et al., 1988), mutants with an altered carbohydrate composition have been found. Brown mid rib (Bmr) corn has been used as an alternative for improving digestibility for silage hybrids for decades. The improvement in ruminal intakes and digestibility is derived from reduced lignin content in Bmr mutated hybrids. Additional varieties, both naturally-occurring and transgenic, with desired traits that are useful for downstream processing as described herein are well known to those of skill in the art.

Plants useful in the present invention also include, but are not limited to, crops producing edible flowers such as cauliflower (*Brassica oleracea*), artichoke (*Cynara scolymus*), and safflower (*Carthamus*, e.g. *tinctorius*); fruits such as apple (*Malus*, e.g. *domesticus*), banana (*Musa*, e.g. *acuminata*), berries (such as the currant; *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut. *Arachis hypoaeae*), orange (*Citrus*, e.g. *maxima*), peach (*Prunus*, e.g. *persica*), pear (*Pyra*, e.g. *communis*), pepper (*Solanum*, e.g. *capsicum*) plum (*Prunus*, e.g. *domestica*), strawberry (*Fragaria*, e.g. *moschata*), tomato (*Lycopersicon*, e.g. *esculentum*); leafs, such as alfalfa (*Medicago*, e.g. *saliva*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (*Glycine*, e.g. *max*), wheat (*Triticum*, e.g. *aestivum*), barley (*Hordeum*, e.g. *vulgare*), corn (*Zea*, e.g. *mays*), rice (*Oryza*, e.g. *sativa*); grasses, such as *Miscanthus* grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. *oleraceae*), potato (*Solanum*, e.g. *tuberosum*), and the like.

Plant Transformation

The expression constructs described herein can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the npt11 gene, which confers resistance to kanamycin and related, antibiotics (Messing & Vierra. Gene 19: 259-268 (1982); Bevan et al., Nature 304: 184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate icon gene, which provides the ability to metabolize mannose (U.S. Pat. Nos. 5,767,378 and 5,994, 629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and Microinjection. The choice of vector depends largely on the preferred selection for the species being transformed. For the construction of such vectors, see, for example, US Application No. 20060260011, herein incorporated by reference.

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al (Plant Cell 2: 603-618 (1990)) and Fromm et al. (Biotechnology 8: 813-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnologyl 11:1553-1558 (1993)) and Weeks et al, (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS®, helium device using a burst pressure of about 1000 psi using a standard 80 mesh screen. After bombardment, the embryos are placed hack into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml). 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin. 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the T1 seed is harvested.

The plants obtained via transformation with a nucleic acid sequence of the present invention can be any of a wide variety of plant species, including those of monocots and dicots; however, the plants used in the method of the invention, are preferably selected from the list of agronomically important target crops set forth supra. The expression of a gene of the present invention in combination with other characteristics important for production and quality can be incorporated into plant lines through breeding. Breeding, approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 umol photons/m2/s) on plates of RMOP medium (Svab, Z. Hajdukiewicz, P. and Maliga, P. (1990) PNAS 87, 8526-8530) containing 5001.10111 spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346349) is separated on 1% Tris-borate (TBE) agarose gels, transferred to nylon membranes (Amersham) and probed with sup.32P-labeled random primed DNA sequences corresponding to a 0.7 kb BamHI/HindIII DNA fragment from pC8 containing a portion of the rps 7/12plastid targeting sequence. Homoplasmic shoots are rooted aseptically on spectinomycin-containing MS/IBA medium (McBride, K. E. et al. (1994) PNAS 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding. Multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

Use

Plant material harvested from the transgenic plants described herein is useful in downstream agronomical and industrial uses, such as human food, animal feed, biofuel, industrial alcohol, fermentation feedstock, and the like. Thus provided herein are methods for producing a modified multidomain enzyme comprising cultivating plants expressing the modified multidomain enzyme. Methods for producing ethanol comprising fermenting a modified multidomain enzyme-expressing plant are also encompassed, as well as methods for enhancing the digestibility of animal feed by adding a modified multidomain enzyme-expressing plant to the feed mix.

In one embodiment, this plant material can be used to formulate food or beverage for human consumption or animal feed, can be used to formulate diet with easily digestible starch and hence more extractable energy, or can be used to improve the nutritional quality of the food or feed (e.g., increased vitamin content, increased oil content, increased protein content, etc). The food, feed, or beverage can be flour, dough, bread, pasta, cookies, cake, thickener, beer, malted beverage, or a food additive. The food, feed, or beer product of can have reduced allergenicity and/or increased digestibility. Further, a dough product can have increased, strength and volume in comparison to a dough made from a non-transgenic seed or grain of the same species. The food, feed, or beverage can have hyperdigestible protein and/or hyperdigestible starch. The food, feed, or beverage can be hypoallergenic.

Oil extracted from the harvested plant material of the invention can be used as a raw material for chemical modification, a component of biodegradable material, a component of a blended food product, a component of an edible oil or cooking oil, lubricant, or a component thereof, biodiesel or a component thereof, a component of a snack food, a fermentation process raw material, or a component of cosmetics.

The harvested plant material of the invention can also be combined with other ingredients to produce a useful product. The specific ingredients included in a product will be determined according to the ultimate use of the product. Exemplary products include animal feed, raw material for chemical modification, biodegradable materials, blended food product, edible oil, cooking oil, lubricant, biodiesel process raw material, snack food, cosmetics, cleaning and detergent compositions (e.g., laundry detergents, dish washing detergents, and hard surface cleaning compositions), and fermentation process raw material. Products incorporating the harvested plant material described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multi-vitamin supplements, diet drinks, and cereal foods. Products incorporating the harvested plant material described herein include, e.g., cardboard, paper products, and industrial materials. These products may incorporate the raw harvested plant material, or may incorporate a processed or extracted form of the harvested plant material (e.g., oil, protein, starch, etc, extracted from the harvested plant material).

The following examples are offered by way of illustration and not by way of limitation.

EXPERIMENTAL

Standard recombinant DNA and molecular cloning techniques used herein are well known in the art and are described by J. Sambrook, E. F. Fritsch and T. Maniatis, Molecular Cloning: A Laboratory Manual, Cold Spring Harbor laboratory, Cold Spring Harbor, N.Y. (1989) and T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, published by Greene Publishing Assoc. and Wiley-Interscience (1987).

Example 1

Dicot Optimized Cellulase Genes

Dicot plant synthetic genes were designed using the back-translation program in Vector NTI 9.0. Six protein sequences were backtranslated into dicot optimized coding sequences using the preferred codons for dicots. Additional sequence was added to the 5' and 3' end of each cellulase gene coding sequence for cloning and differential targeting to subcellular compartments. For construction of dicot transient expression vectors, an AscI, BamHI, and tobacco Kozak sequences were added at the 5' end. An ER targeting sequence and SacI-NotI cloning sites were added at the 3' end. Silent mutations were introduced to remove any restriction sites which interfered with cloning strategies. Synthetic genes were synthesized by GENEART (Germany).

Example 2

Construction of Plant Expression Vectors

Expression vectors capable of directing the expression of an optimized cellobiohydrolase gene (CBHI) with novel linkers in transgenic plants were designed. Table 1 outlines the sequences and vectors generated.

The constitutive CaMV 35S promoter was used to drive expression of the dicot optimized cellulase genes. Tobacco expressed cellulases were targeted to the endoplasmic reticulum (ER) via fusion to the tobacco PR1a signal sequence (SEQ ID NO:13) and the ER retention sequence (SEQ ID NO:14).

Tobacco expression vectors used the binary vector, pGR106, containing potato virus X (PVX) amplicon (Lu et al., 2003; EMBO J, 22:5690-5699). Vector component information is shown in Table 1.

TABLE 1

Description of sequences

| SEQ ID NO: of cellulase insert | Description of gene | Subcellular targeting | Signal sequence |
|---|---|---|---|
| 1, 2 | CBH1 with native linker (pSM439) | ER retention signal | PR1a ER targeting sequence |
| 1, 2 | CBH1 with native linker | None | None |
| 3, 4 | CBH1 with GGG linker (pSM449) | ER retention signal | PR1a ER targeting sequence |
| 3, 4 | CBH1 with GGG linker | None | None |
| 5, 6 | CBH1 with SGGGG linker (pSM450) | ER retention signal | PR1a ER targeting sequence |
| 5, 6 | CHB1 with SGGGG linker | None | None |
| 7, 8 | CBH1 with AP linker (pSM451) | ER retention signal | PR1a ER targeting sequence |
| 7, 8 | CBH1 with AP linker | None | None |
| 9, 10 | CBH1 with VP linker (pSM452) | ER retention signal | PR1a ER targeting sequence |
| 9, 10 | CBH1 with VP linker | None | None |
| 11, 12 | CBH1 with SP linker (pSM453) | ER retention signal | PR1a ER targeting sequence |
| 11, 12 | CHB1 with SP linker (pSM453) | None | None |

Description of C-Terminal Additions

| SEQ ID NO: | Element |
|---|---|
| 13 | Tobacco PR1a ER targeting sequence |
| 14 | ER retention signal |
| 15 | Beta-conglycinin protein storage vacuole targeting sequence |
| 16 | Maize gamma zein 27 kD ER targeting sequence |
| 17 | Barley polyamine oxidase vacuole targeting sequence |

The *Glycine max* glycinin GY1 promoter and signal sequence (GenBank Accession X15121) will be used to drive soybean seed specific expression of celluloses. Targeting of the cellulose in soybean will involve either the C-terminal addition of ER retention sequence (SEQ ID NO:14) or protein storage vacuole (PSV) sequence, (SEQ ID NO:15) from beta-conglycinin (Plant Phys 2004:134, 625-639).

A variety of promoters will be used to drive expression of monocot optimized cellulases with altered linker regions in transgenic plants. The maize PepC promoter (The Plant Journal 1994: 6(3), 311-319) will be used to drive leaf preferred expression of monocot optimized cellulose genes. The maize TrpA promoter (U.S. Pat. No. 6,018,104 and Plant Mol. Biol 27:1183-1188, 1995)) will be used to drive monocot stem specific expression of the monocot optimized cellulase. Each of the maize optimized cellulases will be cloned behind the rice glutei in promoter for expression in the endosperm of the maize seed.

The expression constructs will use a variety of targeting sequences to target the cellulases with altered linker regions to different organelles. For vacuole targeting, the cellulases with altered linkers will be operably linked to the gamma zein 27 kD signal sequence (SEQ ID NO:16) at the N terminus to targets through ER and fused to the vacuole sequence domain (VSD) from barley polyamine oxidase (SEQ ID NO:17) to direct the cellulose into the leaf vacuole (Plant Phys 2004: 134, 625-639). For retention of the cellulose with altered linker regions in the ER, the ER retention sequence (SEQ ID NO:14) will be used in place of the VSD.

All expression cassettes will be subcloned into a binary vector for transformation into tobacco, soybean, sugarcane, sugar beet and maize using recombinant DNA techniques that are known in the art.

Example 3

Transient Expression of Cellulases in Tobacco Leaves

Expression cassettes described in Example 2 above were cloned into PVX vector pGR106 (Lu et al., 2003). The PVX constructs were transferred into *Agrobacterium tumefaciens* strain GV3101 containing the helper plasmid pJIC SA_Rep (available on the Internet at jic.ac.uk/sainsbury-lab/dcb/Services/vigsprotocol.htm) using the freeze-thaw method (An et al., Binary vector. In: Gelvin S B, Schilproot R A (eds), Plant molecular biology manual. Kluwar Academic Publishers, Dordrecht. pp A3 1-19 (1988)).

Transgenic TEV-B tobacco plants (made in the tobacco cultivar Xanthi) containing a mutated P1/HC-Pro gene from TEV that suppresses post-transcriptional gene silencing (Mallory et al., Nat Biotechnol 20:622 (2002)) were used for transient expression of the cellulase genes described in Example 1. Preparation of *Agrobacterium* cultures and infiltration, of tobacco plants were carded out as described by Azhakanandam et al., Plant Mol. Biol, 63: 393-404 (2007). In brief, the genetically modified *Agrobacteria* were grown overnight in 50 ml of LB medium containing 100 µM acetosyringone and 10 µM MES (pH 5.6), and subsequently were pelleted by centrifugation at 4000 g for 10 min. The pellets were resuspended in the infection medium [Murashige and Skoog salts with vitamins, 2% sucrose, 500 µM MES (pH 5.6), 10 µM MgSO4, and 100 µM acetosyringone] to OD600=1.0 and subsequently held at 28° C. for 3 h. Infiltration of individual leaves was carried out on 4 weeks old recipient plants using a 5 ml syringe by pressing the tip of the syringe (without a needle) against the abaxial surface of the leaf. Infiltrated plants were maintained at 21-22° C. with a photoperiod of 16 h light and 8 h dark. Plant tissue was harvested after 5 days post infiltration for subsequent analysis.

Example 4

Enzyme Analysis of Tobacco Leaves Transiently Expressing Cellulases

Protein extracts were obtained from approximately 100-500 mg of leaf tissue collected from tobacco plants transiently expressing cellulases as described in Example 3. Leaf material from tobacco transiently expressing cellulases was placed into 24 deep well blocks containing small steel balls and pre-cooled on dry ice. Samples were ground to a fine powder rising a Genogrinder (SPEC/CertiPrep, Metuchen, N.J.). Samples were extracted in 500-1000 □l of Western Extraction Buffer (WEB=12.5 mM sodium borate, pH10; 2% BME; and 1% SDS at room temperature for approximately 30 minutes followed by centrifugation for 5 minutes at 13,000 rpm.

Alternatively, leaf or seed tissue will be collected from transgenic plants expressing cellulases with altered linkers. Flour samples will be prepared from seed by pooling approximately 10-20 seed and grinding to a fine powder using, a Kleco Grinder (Gracia Machine Company, Visalia, Ca.). Flour will be extracted as described in the paragraph above for tobacco transiently expressing cellulases.

SDS—polyacrylamide gel electrophoresis (SDS-PAGE) was performed by transferring 100 □l of WEB samples to an eppendorf tube and add 25 □l 4×BioRad LDS or modified BioRad loading buffer (4×BioRad LDS:BME at a ratio of 2:1). Samples were heated for 10 minutes at 70° C. then immediately place on ice for 5 minutes. Following incubation on ice, samples were centrifuged briefly. Sample extracts (5-10 □l) were run on BioRad 4-12% Bis/Tris protein gel (18 well) using MOPS buffer.

Immunoblot analysis was performed by transferring SDS-PAGE gels onto a nitrocellulose membrane using chilled Nupage transfer buffer (Invitrogen) for 30 minutes at 100 volts. Total protein transferred to the blot was visualized using Ponceau stain (Sigma). Following Ponceau stamina the membrane was incubated in blocking buffer for 30 minutes in TBST wash buffer (30 mM Tris-HCL, pH 7.5, 100 mM NaCl, and 0.05% Tween 20) with 3% dry milk, then washed three times for 5 minutes in TBST. Primary antibody was added at 1 ug/ml in TBST wash buffer with 3% milk, and the blot incubated 2 hours to overnight. Following overnight incubation, the blot was washed three times for 5 minutes each in TBST wash buffer. Secondary antibody (Rabbit-AP) was diluted 1:8000 (in TBST) and added to blot for at least 30 minutes. Following incubation in the secondary antibody, the blot was again washed three times for 5 minutes each. Visualization of immuno reactive bands was carried out by adding Moss BCIP/NBT—alkaline phosphatase substrate. Blots were rinsed thoroughly in water following incubation in the BCIP/NBT substrate and allowed to air dry.

Western blot analysis (see Table 2) was carried out using sample extracts from tobacco transient expression of cellulases using the constructs described in Example 2. Immuno-reactive bands detected on the western blot varied in apparent size and staining intensity. The predicted size, based on amino acid sequence, of each of the CBHI proteins with either the native linker (pSM439) or the heterologous linker (pSM449, pSM450, pSM451, pSM452, and pSM453) was 53.3, 52.3, 52.1, 53.1, 53.5, and 53.4 kD, respectively. Immuno-reactive bands were detected for constructs pSM439, pSM449, pSM452, and pSM453. Samples from leaves infiltrated with constructs pSM450 and pSM451, along with controls, showed no detectable protein in this experiment. The CBHI-native linker protein (pSM439) was detected as a band that migrates at about 55 kD The CBHI-Gly linker protein (pSM449) showed a band that migrated slightly below the CBHI-native linker protein. Interestingly, the CBHI-VP linker protein showed broad immuno-detectable band between 55-60 kD. Unexpectedly the CBHI-SP linker protein showed a broad immuno-detectable band between 55-64 kD. These results show that the strategy of using heterologous linkers is capable of improving the expression, accumulation and/or stability of the CBHI protein in plant tissue and that the type of linker appears to influence expression, accumulation and/or stability of the CBHI protein in tobacco.

TABLE 2

Western blot results for plant expression vectors used for tobacco transient experiments.

| Linker Region | Western Results | Construct number |
| --- | --- | --- |
| STGGSSTTTASGTTTTKASSTSTSSTSTGTGV (residues 468 through 499 of SEQ ID NO: 2) | +++ | pSM439 |
| GGGGGGGGGG GGGGGGGGGG GGGGGGGGGG (SEQ ID NO: 21) | + | pSM449 |
| SGGGGSGGGGSGGGGSGGGGSGGGGS (SEQ ID NO. 22) | − | pSM450 |
| APAPAPAPAPAPAPAPAPAPAPAPAPAPAPAP SEQ ID NO: 20) | − | pSM451 |
| VPVPVPVPVPVPVPVPAPVPVPVPVPVPVP (SEQ ID NO: 18) | +++ | pSM452 |
| SPSPSPSPSPSPSPSPSPSPSPSPSPSPSP (SEQ ID NO: 19) | ++++ | pSM453 |

Example 5

Enzyme Extraction and Activity Analysis of Transient Expressed CBHI

Approximately 100-500 mg of fresh leaf tissue from tobacco plants transiently expressing cellulases as described in Example 3, was extracted in 2 to 10 ml 100 mM Na Acetate buffer (pH 4.75), 0.02% NaN3, 0.02% Tween, and 1 Complete protease inhibitor cocktail tablet (Roche) per 50 ml of buffer. One of ordinary skill in the art would be able to identify other standard extraction buffers that would be appropriate for extracting protein from leaf. Samples were placed on benchtop rotators for 30-60 minutes then centrifuged at 3000 rpm for 10 minutes. For fresh leaf samples the amount of total protein extracted was measured by Pierce BCA protocol as outlined in product literature. Cellulase activity assays were carried out using methylumbelliferyl-lactoside (MUL). Additional substrates such as pNP-lactoside, carboxymethyl-cellulose, oat-b glucan, phosphoric acid treated cellulose (PASC). Avicel, or other commercially available substrates can used for measuring cellulase activity following previously published protocols (Methods in Enzymology, Vol 160).

CBHI activity results for transient expression of CBHI with native and heterologous linkers are shown in Table 3. All of the constructs, except pSM450, showed activity on the MUL substrate. Unexpectedly, the CBHI-VP and CBHI-SP proteins showed activity which was slightly lower than that observed for the CBHI-native linker protein. These results are significant, showing that it is possible to create proteolytically stable linkers without disrupting the functionality of the CBHI enzyme when expressed in tobacco.

TABLE 3

Summary of CBH1 activity in tobacco leaves transiently expressing cellulases. Activity is reported as an average of four individual leaves from four different plants. Samples were extracted in buffer and CBH1 activity was assayed on methylumbelliferyl-lactoside as the substrate.

| Sample | Avg CBH1 Activity (nmoles/min/mg TSP) | StDev |
|---|---|---|
| unifiltrated leaf | 0.09 | 0.08 |
| culture medium only | 0.15 | 0.17 |
| PV X vector only | 0.20 | 0.22 |
| pSM439 | 1.55 | 0.46 |
| pSM449 | 0.40 | 0.09 |
| pSM450 | 0.21 | 0.22 |
| pSM451 | 0.56 | 0.37 |
| pSM452 | 0.97 | 0.25 |
| pSM453 | 0.89 | 0.29 |

Example 6

Linker Modifications of Glucoamylase

Variants of the glucoamylase of SEQ ID NO: 24 will be generated in which the linker sequence has been replaced with the sequences outlined in Table 4. The glucoamylase variants will be generated by replacing bp 459-513 of SEQ ID: 24 with the sequence described in Table 4. The linker variants described in Table 4 are designed to alter the linker region of the native glucoamylase such that more full length protein accumulates in plant tissues. Glucoamylase variants made with the linkers of SEQ ID NO: 35-69 will generate glucoamylase variants that are less sensitive to degradation by plant proteases. The recognition site for some proteases are known; however, this recognition site may not be a specific string of amino acids but may be a pattern of specific types of amino acids assembled into a string. In particular the recognition sequence for the protease pepsin will be used to design variant linkers that have less similarity to the known recognition sequence for pepsin. The procine pepsin cleavage site is described by Powers in Adv. Exp. Med. Biol 95: 141-157 (1977).

As outlined in Table 4, the variant linker sequences are designed to avoid plant mediated cleavage of the linker region when the variant is expressed in plant cells. Several approaches will be taken to generate the linker variants. One approach is to eliminate protease cleavage sites of the native glucoamylase linker. Variants of the native glucoamylase linker sequence are outlined in Table 4 which have less similarity to the pepsin cleavage site. Additionally, variants have been designed which incorporate sites for plant based N or O linked glycosylation by increasing, the presence of the amino acids threonine and serine. Glycosylation may protect protease cleavage sites from protease attack by physically blocking access of the protease to the linker region. Another alternative outlined in Table 4 is the replacement of the native glucoamylase linker sequence with linkers from other enzymes which may be less sensitive to plant proteases, or replacement of the native glucoamylase linker sequence with synthetic linker sequences which promote plant based N or O linked glycosylation of the linker sequence.

The glucoamylase variants generated by replacing the native linker sequence (bp 459-513 of SEQ ID NO: 24 with the sequences outlined in Table 4) will be cloned into an expression vector which operably links the following components together; a promoter which is functional in plant cells such as the NOS promoter of SEQ ID NO: 70, subcellular targeting sequence such as the ER targeting sequence from the PR1a gene of SEQ ID NO: 13, dicot-optimized gene encoding the glucoamylase variant polypeptide, ER retention sequence of SEQ ID NO: 14. This expression construct will be designed to target the glucoamylase varient protein to the endoplasmic reticulum and to retain the glucoamylase variant protein in the endoplasmic reticulum.

As an alternative, the glucoamylase variants may be targeted to the vacuole in order to accumulate the variant protein for analysis. The expression construct for vacuolar targeting of the variant glucoamylase will consist of the following components operably linked together; a promoter which is functional in plant cells such as the NOS promoter of SEQ ID NO: 70, an ER targeting sequence such SEQ ID NO: 13, a dicot-optimized gene encoding the glucoamylase variant polypeptide, a vacuolar targeting sequence such as SEQ ID NO: 17.

The expression constructs described above will be generated by synthesis of the described expression cassette DNA by Gene Art. The synthesized expression cassette will be cloned into a binary vector also containing an origin of replication from BCTV, beet curly top virus. The BCTV containing binary vectors will be transferred into *Agrobacterium tumefaciens* strain LBA4404 containing a helper plasmid containing a BCTV replicase sequence using the freeze-thaw method (An et al., Binary vector, In: Gelvin S B, Schilproot R A (eds), Plant molecular biology manual. Kluwar Academic Publishers, Dordrecht, pp A3 1-19 (1988)).

TABLE 4

Linker sequences to be used to create glucoamylase variants.

| SEQ. ID NO: | Variant linker sequence | properties |
|---|---|---|
| 35 | CSTGSATGTYSTPTGTSWPSTSTSGTAGT TTTSATTTTSTSVSSTTTTTTSTTSC | Eliminate protease cleavage site |
| 36 | CSTGSATGPYSTPTGTSWPSTSTSGTAGT TTTSATTTTSTSVSSTTTTTTSTTSC | Eliminar protease cleavage site |
| 37 | CSTGSATGPYSTPTGTSWPSTSTSGTAGT TTTSATTTTSTSVSTTTTTTSTTSC | Eliminate protease cleavage site |
| 38 | CSTGSATGPYSTPTGTSWPSTTSGTAGTT TTSATTTTSTSVSGTTTTTTSTTSC | Eliminate protease cleavage site |
| 39 | CSTGSATGTSTPTGTSWPSTVTSGTAGTT TTSATTTTSTSVSGTTTTTTSTTSC | Eliminate protease cleavage site |

TABLE 4 -continued Linker sequences to be used to create glucoamylase variants.

| SEQ. ID NO: | Variant linker sequence | properties |
|---|---|---|
| 40 | CSTGSATGPYSTPTGTSWPSTSTSGTAGT TTTSATTTTSTTTTTTSTTSC | Eliminate protease cleavage site |
| 41 | CSTGSATGPYSTPTGTSWPSTSTSGTAGT TTTSATTTTTTTTTSTTSC | Eliminate protease cleavage site |
| 42 | CSTGSATGPYSTPTGTSWPSTSTSGTAGT TTTSATTTTSTSVSGTTTTTTSTTSC | Eliminate protease cleavage site |
| 43 | CSTGSATGPYSTPTGTSWPSTVTSGTAGT TTTSATTTTSTSVSGTTTTTTSTTSC | Eliminate protease cleavage site |
| 44 | CSTGSATGPYSTPTGTSWPSTSTSGTAGT TTTSATTTTSTSVSKTNTTTTSTTSC | Eliminate protease cleavage site and add a N-glycosylation site |
| 45 | CSTGSATGPYSTPTGTSWPPSQTPGTAGT TTTSATTTTSTSVSSTTTTTTSTTSC | Eliminate protease cleavage site; add linker from other enzyme |
| 46 | CSTGSATGPYSTPTGTSWPSTSTSGTAGT TTTSATTTTSTTSSASTSTTSC | Eliminate protease cleavage site; add linker from other enzyme |
| 47 | CSTGSATGPYSTPTGTSWPSTSTSGGVPTP TGTTTTTTSTTSC | Eliminate protease cleavage site; add linker from other enzyme |
| 48 | CSTGSATGPYATPTNTAWPTTTQPGTAG TTTTSATTTTSTSVSSTTTTTTSTTSC | Eliminate protease cleavage site; add linker from other enzyme |
| 49 | CSTGSATGPYATPTNTAWPTTTQPGTAG TTTTSATTTTSTTTTTTTSTTSC | Eliminate protease cleavage site; add linker from other enzyme |
| 50 | CSTGSATGTYSTPTGTSWPPSQTPKPGVP SGTPYTPLPC | Add linker from other enzyme |
| 51 | CSTGSATGTYSTPTGTSWPPSQTPSPGVPS GTPSTPLPC | Add linker from other enzyme |
| 52 | CSTGSATGTYSTPTGTSWPPSQTPSPGVPS GTPSTPSPC | Add linker from other enzyme |
| 53 | CSTGSATGTSSTPTGTSWPPSQTPSPGVPS GTPSTPSPC | Add linker from other enzyme |
| 54 | CSTGSATGTSSTPTGTSWPTKSPTTTTAT ATTTTAPSTSTTPPSSSEPATFPTGNC | Add linker from other enzyme and promote N glycosylation |
| 55 | CSTGSATGTSSTPTGTSWPTSSPTTTTATA TTTTAPSTSTTPPSSSTPATFPTGNC | Add linker from other enzyme and promote N glycosylation |
| 56 | CSTGSATGTSSTPTGTSWPTSSPTTT-TATS TTPPSSSTPATFPTGNC | Add linker from other enzyme and promote N glycosylation |
| 57 | CSTGSATGTSSTPTGTSWPTSSPTTSTTPPA SSSTPATFPTGNC | Add linker from other enzyme and promote N glycosylation |
| 58 | CSATSATGPYATPTNTAWPSTVTSGTAGT TTTATTTTSTSVSGTTTQPPERPAC | Eliminate protease cleavage site; add linker from other enzyme |
| 59 | CSATSATGPYATPTNTAWTTTQPPERPAC | Add linker from other enzyme |

TABLE 4 -continued

Linker sequences to be used to create glucoamylase variants.

| SEQ. ID NO: | Variant linker sequence | properties |
|---|---|---|
| 60 | CSATSATGPYATPTNTAWGGGGSTTTQP PERPAC | Add linker from other enzyme plus use of synthetic sequence |
| 61 | CSATSATGPYATPTNTAWGGGGSGGGGS TTTQPPERPAC | Add linker from other enzyme plus use of synthetic sequence |
| 62 | CSATSATGPYATPTNTAWGTAGVPTPTG PTPTTTTQPPERPAC | Eliminate protease cleavage site; add linker from other enzyme |
| 63 | CSTGSATGTYSTPTGTSWPGGGGSGGGG SGGGGSC | synthetic |
| 64 | CSTGSATGTYSTPTGTSWPGGGGSGGGG SGGGGSGGGGSC | synthetic |
| 65 | CSTGSATGTYSTPTGTSWPGGGGSGGGG SGGGGSGGGGSGGGGSC | synthetic |
| 66 | CSTGSATGTYSTPTGTSWPGGGGSGGGG SGGGGSGGGGSGGGGSSGGGGSC | synthetic |
| 67 | CSTGSATGTYSTPTGTSWPGGGCSCGGG SGGGGSGGGGSATFPTGNC | Synthetic plus N glycosylation sites |
| 68 | CSTGSATGTYSTPTGTSWPGGGGSGGGG SGGGGSGGGGSGNSTISSC | Synthetic plus N glycosylation site |
| 69 | CSTGSATGTYSTPTGTSWPGGGGSGGGG SGGGGSGGGGSGNSTISSATFPTGNC | Synthetic plus N glycosylation sites |

Glucoamylase variant enzymes will be produced by transient expression of the enzyme in the leaves of tobacco plants Transgenic TEV-B tobacco plants (made in the tobacco cultivar Xanthi) containing a mutated P1/HC-Pro gene from TIN that suppresses post-transcriptional gene silencing (Mallory et al., Nat Biotechnol 20:622 (2002)) will be used for transient expression of selected enzymes in tobacco leaves. Alternatively, leaves from non-transgenic tobacco plants will be used for transient expression of selected enzymes in tobacco leaves. Preparation of *Agrobacterium* cultures and infiltration of tobacco plants will be carried out as described by Azhakanandam et al., Plant Mol. Biol. 63: 393-404 (2007). In brief, the genetically modified *agrobacteria* will be grown overnight in 50 mL of LB medium containing 100 µM acetosyringone and 10 µM MES (pH 5.6), and subsequently will be pelleted by centrifugation at 4000×g for 10 min. The pellets will be resuspended in the infection medium [Murashige and Skoog salts with vitamins, 2% sucrose, 500 µM. MES (pH 5.6), 10 µM MgSO4, and 100 µM acetosyringone] to OD600=1.0 and subsequently held at 28 degrees C. for 3 hours. Infiltration of individual leaves will be carried out on TEV-B or non-transgenic tobacco plants (about 4 weeks old) using a 5 mL syringe by pressing the tip of the syringe (without a needle) against the abaxial surface of the leaf. Infiltrated plants will be maintained at 22-25 degrees C. with a photoperiod of 16 hours light and 8 hours dark. Plant tissue will be harvested after 5 days post infiltration for subsequent analysis.

Analysis of variant glucoamylase production by transient expression in tobacco plants will be performed by western blot of plant extracts essentially as described in Example 4. Leaves from tobacco plants transiently expressing the glucoamylase variants will be collected and total protein extracted from the leaves essentially as described in Example 4. The total protein from the tobacco leaves will be separated on a polyacrylamide gel and subsequently transferred to a nylon membrane essentially as described in Example 4. Antibodies which bind to glucoamylase of SEQ ID NO: 24 will be used to detect the glucoamylase variants using standard assays and techniques for western blot analysis. The size of the glucoamylase variants will be determined by comparing the mobility of the variant glucoamylase with a protein standard. Based upon the size of the glucoamylase variant, it will be determined if the linker variant was less sensitive to cleavage by plant proteases. The percentage of the produced glucoamylase variant that is less sensitive to protease cleavage will be determined by comparing the amount of protein in the varying molecular weight bands identified by western blot. Methods for determining the amount and ratio of different sized proteins are known and include imaging the western blot and determining the area of a specific band of protein.

Example 7

Linker Modifications of Cellobiohydrolase (SEQ ID NO: 25-34)

Dicot optimized plant synthetic genes will be designed using the backtranslation program in Vector NTI 9.0. Protein sequences will be backtranslated into dicot optimized coding sequences using the preferred codons for dicots. Additional sequence may be added to the 5' and/or 3' end of each cellulose gene coding sequence for cloning and differential targeting to subcellular compartments. Synthetic genes will be synthesized by GENEART (Germany).

Dicot optimized expression vectors capable of directing the expression of an optimized cellobiohydrolase gene (CBHI) with novel linkers in transgenic plants will be designed. Table 5 outlines the sequences and vectors that will be generated for transient expression in tobacco leaves. A constitutive promoter will be operably linked to the polynucleotide sequence encoding the cellobiohydrolase variants. An example of a constitutive promoter is the NOS promoter from *Agrobacterium* of SEQ ID NO: 70. The cellulose variant enzyme will be targeted to different subcellular compartments. The use of an endoplasmic reticulum (ER) targeting sequence such as SEQ ID NO: 14 will be used to promote passage of the cellobiohydrolase through the ER for appropriate processing. The use of an ER retention sequence such as SEQ ID NO: 23 will be used to retain the cellobiohydrolase in the ER. Alternatively, the use of a vacuolar targeting sequence such as SEQ ID NO: 15 will be used to target the cellobiohydrolase to the vacuole for accumulation. Alternatively, no targeting sequence will be used to accumulate the cellobiohydrolase in the apoplast of the plant cell.

Monocot optimized expression vectors capable of directing the expression of an optimized cellobiohydrolase with novel linkers in transgenic plants will be designed. The expression constructs designed for monocot expression will use a variety of targeting sequences to target the cellulases with altered linker regions to different organelles. For vacuole targeting, the cellulases with altered linkers will be operably linked to the gamma zein 27 kD signal sequence (SEQ ID NO: 16) at the N terminus to target through the ER, and fused to the vacuole sequence domain (VSD) from barley polyamine oxidase (SEQ ID NO:17) to direct the cellulose into the leaf vacuole (Plant Phys 2004: 134, 625-639). For retention of the cellulose with altered linker regions in the ER, the ER retention sequence (SEQ ID NO:14) will be used in place of the VSD. A variety of promoters will be used to drive expression of monocot optimized cellulases with altered linker regions in transgenic plants. The maize PepC promoter (The Plant Journal 1994: 6(3), 311-319) will be used to drive leaf preferred expression of monocot optimized cellulose genes. The maize TrpA promoter (U.S. Pat. No. 6,018,104 and Plant Mot Biol 27:1183-1188, 1995)) will be used to drive monocot stem specific expression of the monocot optimized cellulose. Each of the maize optimized cellulases will be cloned behind the rice glutelin promoter for expression in the endosperm of the maize seed.

All monocot optimized expression cassettes will be subcloned into a binary vector for transformation into tobacco, soybean, sugarcane, sugar beet and maize using recombinant DNA techniques that are known in the art.

TABLE 5

Expression constructs containing variants of CBH1 with modified linkers.

| Construct | Description of gene (SEQ ID NO:) | Subcelluar targeting (SEQ ID NO:) | Signal sequence (SEQ ID NO:) |
|---|---|---|---|
| CBH1 linker 9 | CBH1, linker modified to promote glycosylation (25) | Vacuole (15) | PR1a ER targeting sequence (14) |
| CBH1 linker 8 | CBH1, linker modified to promote glycosylation (26) | ER retention (23) | ER targeting sequence (13) |
| CBH1 linker 7 | CBH1, linker modified to promote glycosylation (27) | ER retention (23) | ER targeting sequence (13) |
| CBH1 linker 6 | CBH1, linker modified to promote glycosylation (28) | ER retention (23) | ER targeting sequence (13) |
| CBH1 linker 5 | CBH1, linker modified to promote glycosylation (29) | ER retention (23) | ER targeting sequence (13) |
| CBH1 linker 4 | CBH1, linker modified to promote glycosylation (30) | ER retention (23) | ER targeting sequence (13) |
| CBH1 linker 3 | CBH1, linker modified to promote glycosylation (31) | ER retention (23) | ER targeting sequence (13) |
| CBH1 linker 2 | CBH1, linker modified to promote glycosylation (32) | ER retention (23) | ER targeting sequence (13) |
| CBH1 linker 10 | CBH1, linker modified to promote glycosylation (33) | none | ER targeting sequence (14) |
| CBH1 linker 1 | CBH1, linker modified to promote glycosylation (34) | ER retention (23) | ER targeting sequence (I3) |
| pSM439 CBH1 | CBH1 with native linker (pSM439) (1, 2) | Vacuole (17) | PR1a ER targeting sequence (14) |
| pSM449 CBH1 | CBH1 with GGG linker (pSM439) (3, 4) | Vacuole (17) | PR1a ER targeting sequence (14) |
| pSM450 CBH1 | CBH1 with SGGGG linker (pSM450) (5, 6) | Vacuole (17) | PR1a ER targeting sequence (14) |
| pSM451 CBH1 | CBH1 with AP linker (pSM451) (7, 8) | Vacuole (17) | PR1a ER targeting sequence (14) |
| pSM452 CBH1 | CBH1 with VP linker (pSM452) (9, 10) | Vacuole (17) | PR1a ER targeting sequence (14) |
| pSM453 CBH1 | CBH1 with SP linker (pSM453) (11, 12) | Vacuole (17) | PR1a ER targeting sequence (14) |
| pSM439 CBH1 | CBH1 with native linker (pSM439) (1, 2) | None | PR1a ER targeting sequence (14) |
| pSM449 CBH1 | CBH1 with GGG linker (pSM439) (3, 4) | None | PR1a ER targeting sequence (14) |
| pSM450 CBH1 | CBH1 with SGGGG linker (pSM450) (5, 6) | None | PR1a ER targeting sequence (14) |
| pSM451 CBH1 | CBH1 with AP linker (pSM451) (7, 8) | None | PR1a ER targeting sequence (14) |
| pSM452 CBH1 | CBH1 with VP linker (pSM452) (9, 10) | None | PR1a ER targeting sequence (14) |

TABLE 5-continued

Expression constructs containing variants of CBH1 with modified linkers.

| Construct | Description of gene (SEQ ID NO:) | Subcelluar targeting (SEQ ID NO:) | Signal sequence (SEQ ID NO:) |
|---|---|---|---|
| pSM453 CBH1 | CBH1 with SP linker (pSM453) (11, 12) | None | PR1a ER targeting sequence (14) |

Analysis of plant expression of cellobiohydrolase linker variants will be performed by western blot analysis of variants expressed transiently in tobacco leaves. The leaves from tobacco plants transiently expressing the cellobiohydrolase constructs will be generated essentially as described in Example 6 for glucoamylase variants. Briefly, tobacco leaves will be infiltrated with *agrobacterium* containing an expression cassette containing the variant cellobiohydrolase constructs. Tobacco leaves will be collected after approximately 5 days and the protein in the leaves extracted essentially as described in Example 4. Western blot analysis will be formed essentially as described in Example 4 using antibodies that react with the cellobiohydrolase variant protein. Table 6 outlines Western blot analysis of cellobiohydrolase linker variants expressed transiently in tobacco leaves.

TABLE 6

Western blot analysis of Cellobiohydrolase linker variants.

| Construct (SEQ ID NO:) | Subcellular targeting (SEQ ID NO:) | Relative proportion full-lenght protein * |
|---|---|---|
| CBH1 linker 8 (26) | ER retention (23) | +++ |
| CBH1 linker 9 (25) | Vacuole (15) | − |
| CBH1 linker 10 (33) | None | +++ |
| pSM439 CBH1 (1, 2) | Vacuole (17) | + |
| pSM449 CBH1 (3, 4) | Vacuole (17) | ++++ |
| pSM450 CBH1 (5, 6) | Vacuole (17) | ++++ |
| pSM451 CBH1 (7, 8) | Vacuole (17) | ++++ |
| pSM452 CBH1 (9, 10) | Vacuole (17) | ++++ |
| pSM453 CBH1 (11, 12) | Vacuole (17) | ++++ |
| pSM439 CBH1 (1, 2) | None | + |
| pSM449 CBH1 (3, 4) | None | +++ |
| pSM450 CBH1 (5, 6) | None | +++ |
| pSM451 CBH1 (7, 8) | None | +++ |
| pSM452 CBH1 (9, 10) | None | +++ |
| pSM453 CBH1 (11, 12) | None | ++++ |

* Refers to proportion of full-length protein as detected by Western blot by anti CBH1 antibody probe, indicating that all (++++), some (++) or none (−) of the detectable protein had an apparent molecular weight similar to, or greater than, the predicted full length CBH1 protein.

The modified linker variants of CBHI were transiently expressed in tobacco leaves and the lysates of tobacco leaves collected as described above. The lysates were analyzed by Western blot using an antibody that recognizes CBHI and showed significant increase in proportion of full-length CBHI protein compared to similarly expressed CBHI with native linker sequence (pSM439). CBHI linker 8 and CBHI linker 10, displayed resistance to proteolytic cleavage in the ER and apoplast targeted constructs. Linker variants pSM449, pSM450, pSM451, pSM452 and pSM453 were directed to the vacuole and these linker variants resulted in protein with a molecular weight similar to, or greater than pSM439 directed to the vacuole. All of the protein produced is likely full length. Apoplast targeted CBHI linker variants of pSM449, pSM450, pSM451, pSM452 and pSM453, was predominantly similar to or greater than, the predicted molecular weight of full length CBHI, indicating a minimal amount of proteolytic cleavage. The data show that linker amino acid sequences may be engineered to reduce and/or eliminate proteolytic cleavage of CBHI.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for expressing a multidomain enzyme in a plant cell comprising introducing into said plant cell a nucleic acid construct comprising a nucleotide sequence encoding a modified multidomain enzyme, wherein said multidomain enzyme comprises at least one first domain, at least one first linker sequence, and at least one second domain, wherein said first domain and said second domain are non-heterologous sequence, wherein the native linker sequence in said modified multidomain enzyme has been replaced with a heterologous linker sequence, wherein said heterologous linker sequence is a linker sequence that is not cleaved by a plant protease, wherein said heterologous linker sequence is selected from the group consisting of SEQ ID NO:18, 19, and 20, and wherein the multidomain enzyme is targeted to a vacuole.

2. The method of claim 1, wherein said plant cell expresses said modified multidomain enzyme, wherein a full length multidomain enzyme is produced by said plant cell.

3. The method of claim 1, wherein said multidomain enzyme is selected from the group consisting of a cellulase enzyme and a glucoamylase enzyme.

4. The method of claim 1, wherein said plant cell is selected from the group consisting of a rice, wheat, corn, soybean, sugar beet, and sugar cane plant cell.

5. A plant cell comprising a nucleic acid construct comprising a nucleotide sequence encoding a modified multidomain enzyme, wherein said multidomain enzyme comprises at least one first domain, at least one first linker sequence, and at least one second domain, wherein the native linker sequence in said modified multidomain enzyme has been replaced with a heterologous linker sequence, wherein said first domain and said second domain are non-heterologous sequence, wherein the native linker sequence in said modified multidomain enzyme has been replaced with a heterologous linker sequence, wherein said heterologous linker sequence is a linker sequence that is not cleaved by a plant protease, wherein said heterologous linker sequence is selected from the group consisting of SEQ ID NO:18, 19, and 20, and wherein the multidomain enzyme is targeted to a vacuole.

6. The plant cell of claim 5, wherein said plant cell expresses said modified multidomain enzyme, wherein a full length multidomain enzyme is produced by said plant cell.

7. The plant cell of claim 5, wherein said multidomain enzyme is a cellulase enzyme.

8. The plant cell of claim 5, wherein said plant cell is selected from the group consisting of a rice, wheat, corn, soybean, sugar beet, and sugar cane plant cell.

9. A plant comprising the plant cell of claim 5.

10. A transgenic seed produced from said plant of claim 9.

11. A method of producing fermentable sugars from plant biomass, said method comprising:
    (a) obtaining a plant comprising a nucleic acid construct comprising a nucleotide sequence encoding a modified multidomain enzyme, wherein said multidomain enzyme comprises at least one first domain, at least one first linker sequence, and at least one second domain, wherein the native linker sequence in said modified multidomain enzyme has been replaced with a heterologous linker sequence, wherein said first domain and said second domain are non-heterologous sequence, wherein said heterologous linker sequence is a linker sequence that is not cleaved by a plant protease, wherein said heterologous linker sequence is selected from the group consisting of SEQ ID NO:18, 19, and 20, wherein the multidomain enzyme is targeted to a vacuole, and wherein said multidomain enzyme is involved in the conversion of plant material to fermentable sugar;
    (b) growing said plant under conditions in which the nucleic acid construct is expressed; and
    (c) using said plant in a biomass conversion method.

* * * * *

SEQUENCE LISTING

```
<160> NUMBER OF SEQ ID NOS: 69

<210> SEQ ID NO 1
<211> LENGTH: 1623
<212> TYPE: DNA
<213> ORGANISM: Artificial Sequence
<220> FEATURE:
<223> OTHER INFORMATION: dicot optimized gene encoding CBH1 with native
      linker sequence
<220> FEATURE:
<221> NAME/KEY: CDS
<222> LOCATION: (1)..(1623)

<400> SEQUENCE: 1
```

```
atg gga ttc gtg ctt ttc tct cag ctt cct tct ttc ctt ctt gtg tct     48
Met Gly Phe Val Leu Phe Ser Gln Leu Pro Ser Phe Leu Leu Val Ser
1               5                   10                  15 act ctt ctt ctt ttc ctt gtg att tct cac tct tgc agg gct caa cag     96
Thr Leu Leu Leu Phe Leu Val Ile Ser His Ser Cys Arg Ala Gln Gln
            20                  25                  30 att gga act tac act gct gag act cac cca tct ttg tct tgg tct act    144
Ile Gly Thr Tyr Thr Ala Glu Thr His Pro Ser Leu Ser Trp Ser Thr
                35                  40                  45 tgc aag tct ggt gga tct tgc act act aac tct ggt gct att act ctt    192
Cys Lys Ser Gly Gly Ser Cys Thr Thr Asn Ser Gly Ala Ile Thr Leu
        50                  55                  60 gat gct aat tgg aga tgg gtg cac ggt gtt aac act tct act aac tgc    240
Asp Ala Asn Trp Arg Trp Val His Gly Val Asn Thr Ser Thr Asn Cys
65                  70                  75                  80 tac act gga aac act tgg aac act gct att tgc gat act gat gct tct    288
Tyr Thr Gly Asn Thr Trp Asn Thr Ala Ile Cys Asp Thr Asp Ala Ser
                85                  90                  95 tgc gct caa gat tgc gct ctt gat ggt gct gat tac tca gga act tac    336
Cys Ala Gln Asp Cys Ala Leu Asp Gly Ala Asp Tyr Ser Gly Thr Tyr
            100                 105                 110 gga att act act tct gga aac tct ctt agg ctt aac ttc gtg act gga    384
Gly Ile Thr Thr Ser Gly Asn Ser Leu Arg Leu Asn Phe Val Thr Gly
                115                 120                 125 tct aat gtg gga tct agg act tac ctt atg gct gat aac act cac tac    432
Ser Asn Val Gly Ser Arg Thr Tyr Leu Met Ala Asp Asn Thr His Tyr
        130                 135                 140 cag att ttc gat ctt ctt aac cag gaa ttc act ttc act gtt gat gtg    480
Gln Ile Phe Asp Leu Leu Asn Gln Glu Phe Thr Phe Thr Val Asp Val
145                 150                 155                 160 tct cat ctt cca tgc gga ctt aac ggt gct ctt tac ttc gtg act atg    528
Ser His Leu Pro Cys Gly Leu Asn Gly Ala Leu Tyr Phe Val Thr Met
                165                 170                 175 gat gct gat ggt gga gtt tct aag tac cca aac aac aag gct ggt gct    576
Asp Ala Asp Gly Gly Val Ser Lys Tyr Pro Asn Asn Lys Ala Gly Ala
            180                 185                 190 caa tat ggt gtt gga tac tgc gat tct caa tgc cca agg gat ctt aag    624
Gln Tyr Gly Val Gly Tyr Cys Asp Ser Gln Cys Pro Arg Asp Leu Lys
                195                 200                 205 ttc att gct gga cag gct aat gtt gaa gga tgg act cca tct tct aac    672
Phe Ile Ala Gly Gln Ala Asn Val Glu Gly Trp Thr Pro Ser Ser Asn
        210                 215                 220 aac gct aac act gga ctt gga aat cat ggt gct tgc tgc gct gaa ctt    720
Asn Ala Asn Thr Gly Leu Gly Asn His Gly Ala Cys Cys Ala Glu Leu
225                 230                 235                 240 gat att tgg gag gct aac tct att tct gag gct ctt act cca cat cca    768
Asp Ile Trp Glu Ala Asn Ser Ile Ser Glu Ala Leu Thr Pro His Pro
                245                 250                 255 tgc gat act cca gga ctt tct gtg tgc act act gat gct tgt gga gga    816
Cys Asp Thr Pro Gly Leu Ser Val Cys Thr Thr Asp Ala Cys Gly Gly
            260                 265                 270 act tac tct tct gat aga tac gct gga act tgc gat cca gat gga tgc    864
Thr Tyr Ser Ser Asp Arg Tyr Ala Gly Thr Cys Asp Pro Asp Gly Cys
                275                 280                 285 gat ttc aac cca tac agg ctt gga gtg act gat ttc tac gga tct gga    912
Asp Phe Asn Pro Tyr Arg Leu Gly Val Thr Asp Phe Tyr Gly Ser Gly
        290                 295                 300 aag act gtg gat aca act aag cca att act gtg gtg act cag ttc gtg    960
Lys Thr Val Asp Thr Thr Lys Pro Ile Thr Val Val Thr Gln Phe Val
305                 310                 315                 320
```

```
act gat gat gga act tct act gga act ctt tct gag att aga agg tac       1008
Thr Asp Asp Gly Thr Ser Thr Gly Thr Leu Ser Glu Ile Arg Arg Tyr
                325                 330                 335 tac gtt cag aac ggt gtt gtt att cca cag cca tct tct aag att tct       1056
Tyr Val Gln Asn Gly Val Val Ile Pro Gln Pro Ser Ser Lys Ile Ser
    340                 345                 350 ggt gtg tct gga aac gtg att aac tct gat ttc tgt gat gct gag att       1104
Gly Val Ser Gly Asn Val Ile Asn Ser Asp Phe Cys Asp Ala Glu Ile
355                 360                 365 tct act ttc gga gag act gct tct ttt tct aag cac ggt gga ctt gct       1152
Ser Thr Phe Gly Glu Thr Ala Ser Phe Ser Lys His Gly Gly Leu Ala
        370                 375                 380 aaa atg gga gct gga atg gaa gct gga atg gtg ctt gtg atg tct ctt       1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca       1248
Trp Asp Asp Tyr Ser Val Asn Met Leu Trp Leu Asp Ser Thr Tyr Pro
                405                 410                 415 act aac gct act ggt act cca ggt gct gct aga gga tct tgc cca act       1296
Thr Asn Ala Thr Gly Thr Pro Gly Ala Ala Arg Gly Ser Cys Pro Thr
    420                 425                 430 act tct ggt gat cct aag act gtg gag tct cag tct gga tct tct tac       1344
Thr Ser Gly Asp Pro Lys Thr Val Glu Ser Gln Ser Gly Ser Ser Tyr
435                 440                 445 gtg act ttc tct gat att aga gtg gga cca ttc aac tct act ttc tct       1392
Val Thr Phe Ser Asp Ile Arg Val Gly Pro Phe Asn Ser Thr Phe Ser
        450                 455                 460 ggt ggt tct tct act ggt gga tca tct act act act gct tca gga act       1440
Gly Gly Ser Ser Thr Gly Gly Ser Ser Thr Thr Thr Ala Ser Gly Thr
465                 470                 475                 480 act act act aag gct tct tct act tct act tca act tca act ggt           1488
Thr Thr Thr Lys Ala Ser Ser Thr Ser Thr Ser Thr Ser Thr Gly
                485                 490                 495 act ggt gtt gct gct cat tgg gga caa tgt gga gga caa gga tgg act       1536
Thr Gly Val Ala Ala His Trp Gly Gln Cys Gly Gly Gln Gly Trp Thr
    500                 505                 510 gga cca act act tgt gct tct ggt act act tgc act gtg gtg aac cct       1584
Gly Pro Thr Thr Cys Ala Ser Gly Thr Thr Cys Thr Val Val Asn Pro
515                 520                 525 tac tac tct cag tgc ctt tct gag aag gat gag ctt tga                   1623
Tyr Tyr Ser Gln Cys Leu Ser Glu Lys Asp Glu Leu
        530                 535                 540

<210> SEQ ID NO 2
<211> LENGTH: 540
<212> TYPE: PRT
<213> ORGANISM: Artificial Sequence
<220> FEATURE:
<223> OTHER INFORMATION: Synthetic Construct

<400> SEQUENCE: 2

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Gln Gln
            20                  25                  30

Ile Gly Thr Tyr Thr Ala Glu Thr His Pro Ser Leu Ser Trp Ser Thr
        35                  40                  45

Cys Lys Ser Gly Gly Ser Cys Thr Thr Asn Ser Gly Ala Ile Thr Leu
    50                  55                  60
```

-continued

```
Asp Ala Asn Trp Arg Trp Val His Gly Val Asn Thr Ser Thr Asn Cys
 65                  70                  75                  80

Tyr Thr Gly Asn Thr Trp Asn Thr Ala Ile Cys Asp Thr Asp Ala Ser
                 85                  90                  95

Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
        115                 120                 125

Ser Asn Val Gly Ser Arg Thr Tyr Leu Met Ala Asp Asn Thr His Tyr
    130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Ala Gly Gln Ala Asn Val Glu Gly Trp Thr Pro Ser Ser Asn
    210                 215                 220

Asn Ala Asn Thr Gly Leu Gly Asn His Gly Ala Cys Cys Ala Glu Leu
225                 230                 235                 240

Asp Ile Trp Glu Ala Asn Ser Ile Ser Glu Ala Leu Thr Pro His Pro
                245                 250                 255

Cys Asp Thr Pro Gly Leu Ser Val Cys Thr Thr Asp Ala Cys Gly Gly
            260                 265                 270

Thr Tyr Ser Ser Asp Arg Tyr Ala Gly Thr Cys Asp Pro Asp Gly Cys
        275                 280                 285

Asp Phe Asn Pro Tyr Arg Leu Gly Val Thr Asp Phe Tyr Gly Ser Gly
    290                 295                 300

Lys Thr Val Asp Thr Thr Lys Pro Ile Thr Val Val Thr Gln Phe Val
305                 310                 315                 320

Thr Asp Asp Gly Thr Ser Thr Gly Thr Leu Ser Glu Ile Arg Arg Tyr
                325                 330                 335

Tyr Val Gln Asn Gly Val Val Ile Pro Gln Pro Ser Ser Lys Ile Ser
            340                 345                 350

Gly Val Ser Gly Asn Val Ile Asn Ser Asp Phe Cys Asp Ala Glu Ile
        355                 360                 365

Ser Thr Phe Gly Glu Thr Ala Ser Phe Ser Lys His Gly Gly Leu Ala
    370                 375                 380

Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
                405                 410                 415

Thr Asn Ala Thr Gly Thr Pro Gly Ala Ala Arg Gly Ser Cys Pro Thr
            420                 425                 430

Thr Ser Gly Asp Pro Lys Thr Val Glu Ser Gln Ser Gly Ser Ser Tyr
        435                 440                 445

Val Thr Phe Ser Asp Ile Arg Val Gly Pro Phe Asn Ser Thr Phe Ser
    450                 455                 460

Gly Gly Ser Ser Thr Gly Gly Ser Ser Thr Thr Ala Ser Gly Thr
465                 470                 475                 480

Thr Thr Thr Lys Ala Ser Ser Thr Ser Thr Ser Ser Thr Ser Thr Gly
```

```
                        485                 490                 495
Thr Gly Val Ala Ala His Trp Gly Gln Cys Gly Gly Gln Gly Trp Thr
                    500                 505                 510

Gly Pro Thr Thr Cys Ala Ser Gly Thr Thr Cys Thr Val Val Asn Pro
                515                 520                 525

Tyr Tyr Ser Gln Cys Leu Ser Glu Lys Asp Glu Leu
            530                 535                 540

<210> SEQ ID NO 3
<211> LENGTH: 1623
<212> TYPE: DNA
<213> ORGANISM: Artificial Sequence
<220> FEATURE:
<223> OTHER INFORMATION: dicot optimized CBH1 gene with modified linker
      sequence (pSM449)
<220> FEATURE:
<221> NAME/KEY: CDS
<222> LOCATION: (1)..(1623)

<400> SEQUENCE: 3 atg gga ttc gtg ctt ttc tct cag ctt cct tct ttc ctt ctt gtg tct        48
Met Gly Phe Val Leu Phe Ser Gln Leu Pro Ser Phe Leu Leu Val Ser
1               5                   10                  15 act ctt ctt ctt ttc ctt gtg att tct cac tct tgc agg gct caa cag        96
Thr Leu Leu Leu Phe Leu Val Ile Ser His Ser Cys Arg Ala Gln Gln
            20                  25                  30 att gga act tac act gct gag act cac cca tct ttg tct tgg tct act       144
Ile Gly Thr Tyr Thr Ala Glu Thr His Pro Ser Leu Ser Trp Ser Thr
        35                  40                  45 tgc aag tct ggt gga tct tgc act act aac tct ggt gct att act ctt       192
Cys Lys Ser Gly Gly Ser Cys Thr Thr Asn Ser Gly Ala Ile Thr Leu
    50                  55                  60 gat gct aat tgg aga tgg gtg cac ggt gtt aac act tct act aac tgc       240
Asp Ala Asn Trp Arg Trp Val His Gly Val Asn Thr Ser Thr Asn Cys
65                  70                  75                  80 tac act gga aac act tgg aac act gct att tgc gat act gat gct tct       288
Tyr Thr Gly Asn Thr Trp Asn Thr Ala Ile Cys Asp Thr Asp Ala Ser
                85                  90                  95 tgc gct caa gat tgc gct ctt gat ggt gct gat tac tca gga act tac       336
Cys Ala Gln Asp Cys Ala Leu Asp Gly Ala Asp Tyr Ser Gly Thr Tyr
            100                 105                 110 gga att act act tct gga aac tct ctt agg ctt aac ttc gtg act gga       384
Gly Ile Thr Thr Ser Gly Asn Ser Leu Arg Leu Asn Phe Val Thr Gly
        115                 120                 125 tct aat gtg gga tct agg act tac ctt atg gct gat aac act cac tac       432
Ser Asn Val Gly Ser Arg Thr Tyr Leu Met Ala Asp Asn Thr His Tyr
    130                 135                 140 cag att ttc gat ctt ctt aac cag gaa ttc act ttc act gtt gat gtg       480
Gln Ile Phe Asp Leu Leu Asn Gln Glu Phe Thr Phe Thr Val Asp Val
145                 150                 155                 160 tct cat ctt cca tgc gga ctt aac ggt gct ctt tac ttc gtg act atg       528
Ser His Leu Pro Cys Gly Leu Asn Gly Ala Leu Tyr Phe Val Thr Met
                165                 170                 175 gat gct gat ggt gga gtt tct aag tac cca aac aac aag gct ggt gct       576
Asp Ala Asp Gly Gly Val Ser Lys Tyr Pro Asn Asn Lys Ala Gly Ala
            180                 185                 190 caa tat ggt gtt gga tac tgc gat tct caa tgc cca agg gat ctt aag       624
Gln Tyr Gly Val Gly Tyr Cys Asp Ser Gln Cys Pro Arg Asp Leu Lys
        195                 200                 205 ttc att gct gga cag gct aat gtt gaa gga tgg act cca tct tct aac       672
Phe Ile Ala Gly Gln Ala Asn Val Glu Gly Trp Thr Pro Ser Ser Asn
```

```
                    210                 215                 220
aac gct aac act gga ctt gga aat cat ggt gct tgc tgc gct gaa ctt      720
Asn Ala Asn Thr Gly Leu Gly Asn His Gly Ala Cys Cys Ala Glu Leu
225                 230                 235                 240 gat att tgg gag gct aac tct att tct gag gct ctt act cca cat cca      768
Asp Ile Trp Glu Ala Asn Ser Ile Ser Glu Ala Leu Thr Pro His Pro
                        245                 250                 255 tgc gat act cca gga ctt tct gtg tgc act act gat gct tgt gga gga      816
Cys Asp Thr Pro Gly Leu Ser Val Cys Thr Thr Asp Ala Cys Gly Gly
                260                 265                 270 act tac tct tct gat aga tac gct gga act tgc gat cca gat gga tgc      864
Thr Tyr Ser Ser Asp Arg Tyr Ala Gly Thr Cys Asp Pro Asp Gly Cys
                    275                 280                 285 gat ttc aac cca tac agg ctt gga gtg act gat ttc tac gga tct gga      912
Asp Phe Asn Pro Tyr Arg Leu Gly Val Thr Asp Phe Tyr Gly Ser Gly
            290                 295                 300 aag act gtg gat aca act aag cca att act gtg gtg act cag ttc gtg      960
Lys Thr Val Asp Thr Thr Lys Pro Ile Thr Val Val Thr Gln Phe Val
305                 310                 315                 320 act gat gat gga act tct act gga act ctt tct gag att aga agg tac     1008
Thr Asp Asp Gly Thr Ser Thr Gly Thr Leu Ser Glu Ile Arg Arg Tyr
                        325                 330                 335 tac gtt cag aac ggt gtt gtt att cca cag cca tct tct aag att tct     1056
Tyr Val Gln Asn Gly Val Val Ile Pro Gln Pro Ser Ser Lys Ile Ser
                340                 345                 350 ggt gtg tct gga aac gtg att aac tct gat ttc tgt gat gct gag att     1104
Gly Val Ser Gly Asn Val Ile Asn Ser Asp Phe Cys Asp Ala Glu Ile
                    355                 360                 365 tct act ttc gga gag act gct tct ttt tct aag cac ggt gga ctt gct     1152
Ser Thr Phe Gly Glu Thr Ala Ser Phe Ser Lys His Gly Gly Leu Ala
            370                 375                 380 aaa atg gga gct gga atg gaa gct gga atg gtg ctt gtg atg tct ctt     1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca     1248
Trp Asp Asp Tyr Ser Val Asn Met Leu Trp Leu Asp Ser Thr Tyr Pro
                        405                 410                 415 act aac gct act ggt act cca ggt gct gct aga gga tct tgc cca act     1296
Thr Asn Ala Thr Gly Thr Pro Gly Ala Ala Arg Gly Ser Cys Pro Thr
                420                 425                 430 act tct ggt gat cct aag act gtg gag tct cag tct gga tct tct tac     1344
Thr Ser Gly Asp Pro Lys Thr Val Glu Ser Gln Ser Gly Ser Ser Tyr
                    435                 440                 445 gtg act ttc tct gat att aga gtg gga cca ttc aac tct act ttc tcc     1392
Val Thr Phe Ser Asp Ile Arg Val Gly Pro Phe Asn Ser Thr Phe Ser
            450                 455                 460 ggt gga tct tct act ggt gga ggt gga ggt ggt gga ggt gga ggt         1440
Gly Gly Ser Ser Thr Gly Gly Gly Gly Gly Gly Gly Gly Gly Gly
465                 470                 475                 480 ggt ggt ggt gga ggt gga ggt gga ggt ggt ggt ggt gga ggt gga         1488
Gly Gly Gly Gly Gly Gly Gly Gly Gly Gly Gly Gly Gly Gly Gly
                        485                 490                 495 ggt ggt gga gct gct cat tgg gga caa tgt gga gga caa gga tgg act     1536
Gly Gly Gly Ala Ala His Trp Gly Gln Cys Gly Gly Gln Gly Trp Thr
                500                 505                 510 gga cca act act tgt gct tct gga act act tgc act gtg gtg aac cct     1584
Gly Pro Thr Thr Cys Ala Ser Gly Thr Thr Cys Thr Val Val Asn Pro
                    515                 520                 525 tac tac tct cag tgc ctt tct gag aag gat gag ctt tga                 1623
Tyr Tyr Ser Gln Cys Leu Ser Glu Lys Asp Glu Leu
```

Tyr Tyr Ser Gln Cys Leu Ser Glu Lys Asp Glu Leu
            530                 535                 540

<210> SEQ ID NO 4
<211> LENGTH: 540
<212> TYPE: PRT
<213> ORGANISM: Artificial Sequence
<220> FEATURE:
<223> OTHER INFORMATION: Synthetic Construct

<400> SEQUENCE: 4

Met Gly Phe Val Leu Phe Ser Gln Leu Pro Ser Phe Leu Leu Val Ser
1               5                   10                  15

Thr Leu Leu Phe Leu Val Ile Ser His Ser Cys Arg Ala Gln Gln
            20                  25                  30

Ile Gly Thr Tyr Thr Ala Glu Thr His Pro Ser Leu Ser Trp Ser Thr
            35                  40                  45

Cys Lys Ser Gly Gly Ser Cys Thr Asn Ser Gly Ala Ile Thr Leu
        50                  55                  60

Asp Ala Asn Trp Arg Trp Val His Gly Val Asn Thr Ser Thr Asn Cys
65                  70                  75                  80

Tyr Thr Gly Asn Thr Trp Asn Thr Ala Ile Cys Asp Thr Asp Ala Ser
                85                  90                  95

Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
        115                 120                 125

Ser Asn Val Gly Ser Arg Thr Tyr Leu Met Ala Asp Asn Thr His Tyr
    130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Ala Gly Gln Ala Asn Val Glu Gly Trp Thr Pro Ser Ser Asn
210                 215                 220

Asn Ala Asn Thr Gly Leu Gly Asn His Gly Ala Cys Cys Ala Glu Leu
225                 230                 235                 240

Asp Ile Trp Glu Ala Asn Ser Ile Ser Glu Ala Leu Thr Pro His Pro
                245                 250                 255

Cys Asp Thr Pro Gly Leu Ser Val Cys Thr Thr Asp Ala Cys Gly Gly
            260                 265                 270

Thr Tyr Ser Ser Asp Arg Tyr Ala Gly Thr Cys Asp Pro Asp Gly Cys
        275                 280                 285

Asp Phe Asn Pro Tyr Arg Leu Gly Val Thr Asp Phe Tyr Gly Ser Gly
    290                 295                 300

Lys Thr Val Asp Thr Thr Lys Pro Ile Thr Val Thr Gln Phe Val
305                 310                 315                 320

Thr Asp Asp Gly Thr Ser Thr Gly Thr Leu Ser Glu Ile Arg Arg Tyr
                325                 330                 335

Tyr Val Gln Asn Gly Val Val Ile Pro Gln Pro Ser Ser Lys Ile Ser
            340                 345                 350

```
Gly Val Ser Gly Asn Val Ile Asn Ser Asp Phe Cys Asp Ala Glu Ile
            355                 360                 365

Ser Thr Phe Gly Glu Thr Ala Ser Phe Ser Lys His Gly Gly Leu Ala
    370                 375                 380

Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
                405                 410                 415

Thr Asn Ala Thr Gly Thr Pro Gly Ala Ala Arg Gly Ser Cys Pro Thr
            420                 425                 430

Thr Ser Gly Asp Pro Lys Thr Val Glu Ser Gln Ser Gly Ser Ser Tyr
        435                 440                 445

Val Thr Phe Ser Asp Ile Arg Val Gly Pro Phe Asn Ser Thr Phe Ser
    450                 455                 460

Gly Gly Ser Ser Thr Gly Gly Gly Gly Gly Gly Gly Gly Gly Gly Gly
465                 470                 475                 480

Gly Gly Gly Gly Gly Gly Gly Gly Gly Gly Gly Gly Gly Gly Gly Gly
                485                 490                 495

Gly Gly Gly Ala Ala His Trp Gly Gln Cys Gly Gly Gln Gly Trp Thr
            500                 505                 510

Gly Pro Thr Thr Cys Ala Ser Gly Thr Thr Cys Thr Val Val Asn Pro
        515                 520                 525

Tyr Tyr Ser Gln Cys Leu Ser Glu Lys Asp Glu Leu
    530                 535                 540

<210> SEQ ID NO 5
<211> LENGTH: 1605
<212> TYPE: DNA
<213> ORGANISM: Artificial Sequence
<220> FEATURE:
<223> OTHER INFORMATION: dicot optimized CBH1 gene with modified linker
      (pSM450)
<220> FEATURE:
<221> NAME/KEY: CDS
<222> LOCATION: (1)..(1605)

<400> SEQUENCE: 5 atg gga ttc gtg ctt ttc tct cag ctt cct tct ttc ctt ctt gtg tct      48
Met Gly Phe Val Leu Phe Ser Gln Leu Pro Ser Phe Leu Leu Val Ser
1               5                   10                  15 act ctt ctt ctt ttc ctt gtg att tct cac tct tgc agg gct caa cag      96
Thr Leu Leu Leu Phe Leu Val Ile Ser His Ser Cys Arg Ala Gln Gln
            20                  25                  30 att gga act tac act gct gag act cac cca tct ttg tct tgg tct act     144
Ile Gly Thr Tyr Thr Ala Glu Thr His Pro Ser Leu Ser Trp Ser Thr
        35                  40                  45 tgc aag tct ggt gga tct tgc act act aac tct ggt gct att act ctt     192
Cys Lys Ser Gly Gly Ser Cys Thr Thr Asn Ser Gly Ala Ile Thr Leu
    50                  55                  60 gat gct aat tgg aga tgg gtg cac ggt gtt aac act tct act aac tgc     240
Asp Ala Asn Trp Arg Trp Val His Gly Val Asn Thr Ser Thr Asn Cys
65                  70                  75                  80 tac act gga aac act tgg aac act gct att tgc gat act gat gct tct     288
Tyr Thr Gly Asn Thr Trp Asn Thr Ala Ile Cys Asp Thr Asp Ala Ser
                85                  90                  95 tgc gct caa gat tgc gct ctt gat ggt gct gat tac tca gga act tac     336
Cys Ala Gln Asp Cys Ala Leu Asp Gly Ala Asp Tyr Ser Gly Thr Tyr
            100                 105                 110 gga att act act tct gga aac tct ctt agg ctt aac ttc gtg act gga     384
```

```
Gly Ile Thr Thr Ser Gly Asn Ser Leu Arg Leu Asn Phe Val Thr Gly
        115                 120                 125 tct aat gtg gga tct agg act tac ctt atg gct gat aac act cac tac    432
Ser Asn Val Gly Ser Arg Thr Tyr Leu Met Ala Asp Asn Thr His Tyr
        130                 135                 140 cag att ttc gat ctt ctt aac cag gaa ttc act ttc act gtt gat gtg    480
Gln Ile Phe Asp Leu Leu Asn Gln Glu Phe Thr Phe Thr Val Asp Val
145                 150                 155                 160 tct cat ctt cca tgc gga ctt aac ggt gct ctt tac ttc gtg act atg    528
Ser His Leu Pro Cys Gly Leu Asn Gly Ala Leu Tyr Phe Val Thr Met
                165                 170                 175 gat gct gat ggt gga gtt tct aag tac cca aac aac aag gct ggt gct    576
Asp Ala Asp Gly Gly Val Ser Lys Tyr Pro Asn Asn Lys Ala Gly Ala
        180                 185                 190 caa tat ggt gtt gga tac tgc gat tct caa tgc cca agg gat ctt aag    624
Gln Tyr Gly Val Gly Tyr Cys Asp Ser Gln Cys Pro Arg Asp Leu Lys
        195                 200                 205 ttc att gct gga cag gct aat gtt gaa gga tgg act cca tct tct aac    672
Phe Ile Ala Gly Gln Ala Asn Val Glu Gly Trp Thr Pro Ser Ser Asn
210                 215                 220 aac gct aac act gga ctt gga aat cat ggt gct tgc tgc gct gaa ctt    720
Asn Ala Asn Thr Gly Leu Gly Asn His Gly Ala Cys Cys Ala Glu Leu
225                 230                 235                 240 gat att tgg gag gct aac tct att tct gag gct ctt act cca cat cca    768
Asp Ile Trp Glu Ala Asn Ser Ile Ser Glu Ala Leu Thr Pro His Pro
                245                 250                 255 tgc gat act cca gga ctt tct gtg tgc act act gat gct tgt gga gga    816
Cys Asp Thr Pro Gly Leu Ser Val Cys Thr Thr Asp Ala Cys Gly Gly
                260                 265                 270 act tac tct tct gat aga tac gct gga act tgc gat cca gat gga tgc    864
Thr Tyr Ser Ser Asp Arg Tyr Ala Gly Thr Cys Asp Pro Asp Gly Cys
        275                 280                 285 gat ttc aac cca tac agg ctt gga gtg act gat ttc tac gga tct gga    912
Asp Phe Asn Pro Tyr Arg Leu Gly Val Thr Asp Phe Tyr Gly Ser Gly
        290                 295                 300 aag act gtg gat aca act aag cca att act gtg gtg act cag ttc gtg    960
Lys Thr Val Asp Thr Thr Lys Pro Ile Thr Val Val Thr Gln Phe Val
305                 310                 315                 320 act gat gat gga act tct act gga act ctt tct gag att aga agg tac   1008
Thr Asp Asp Gly Thr Ser Thr Gly Thr Leu Ser Glu Ile Arg Arg Tyr
                325                 330                 335 tac gtt cag aac ggt gtt gtt att cca cag cca tct tct aag att tct   1056
Tyr Val Gln Asn Gly Val Val Ile Pro Gln Pro Ser Ser Lys Ile Ser
                340                 345                 350 ggt gtg tct gga aac gtg att aac tct gat ttc tgt gat gct gag att   1104
Gly Val Ser Gly Asn Val Ile Asn Ser Asp Phe Cys Asp Ala Glu Ile
        355                 360                 365 tct act ttc gga gag act gct tct ttt tct aag cac ggt gga ctt gct   1152
Ser Thr Phe Gly Glu Thr Ala Ser Phe Ser Lys His Gly Gly Leu Ala
370                 375                 380 aaa atg gga gct gga atg gaa gct gga atg gtg ctt gtg atg tct ctt   1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca   1248
Trp Asp Asp Tyr Ser Val Asn Met Leu Trp Leu Asp Ser Thr Tyr Pro
                405                 410                 415 act aac gct act ggt act cca ggt gct gct aga gga tct tgc cca act   1296
Thr Asn Ala Thr Gly Thr Pro Gly Ala Ala Arg Gly Ser Cys Pro Thr
        420                 425                 430
```

```
act tct ggt gat cct aag act gtg gag tct cag tct gga tct tct tac    1344
Thr Ser Gly Asp Pro Lys Thr Val Glu Ser Gln Ser Gly Ser Ser Tyr
        435                 440                 445 gtg act ttc tct gat att aga gtg gga cca ttc aac tct act ttc tcc    1392
Val Thr Phe Ser Asp Ile Arg Val Gly Pro Phe Asn Ser Thr Phe Ser
450                 455                 460 ggt gga tct tct ggt ggc gga gga tct ggt ggt ggt agt gga ggt        1440
Gly Gly Ser Ser Gly Gly Gly Gly Ser Gly Gly Gly Ser Gly Gly
465                 470                 475                 480 ggt ggt tct ggc gga ggt gga agt ggt ggt gga gga agt gct gct cat    1488
Gly Gly Ser Gly Gly Gly Gly Ser Gly Gly Gly Gly Ser Ala Ala His
                485                 490                 495 tgg gga caa tgt gga gga caa gga tgg act gga cca act act tgt gct   1536
Trp Gly Gln Cys Gly Gly Gln Gly Trp Thr Gly Pro Thr Thr Cys Ala
                500                 505                 510 tct gga act act tgc act gtg gtg aac cct tac tac tct cag tgc ctt   1584
Ser Gly Thr Thr Cys Thr Val Val Asn Pro Tyr Tyr Ser Gln Cys Leu
            515                 520                 525 tct gag aag gat gag ctt tga                                         1605
Ser Glu Lys Asp Glu Leu
        530
```

<210> SEQ ID NO 6
<211> LENGTH: 534
<212> TYPE: PRT
<213> ORGANISM: Artificial Sequence
<220> FEATURE:
<223> OTHER INFORMATION: Synthetic Construct

<400> SEQUENCE: 6

```
Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Gln Gln
            20                  25                  30

Ile Gly Thr Tyr Thr Ala Glu Thr His Pro Ser Leu Ser Trp Ser Thr
        35                  40                  45

Cys Lys Ser Gly Gly Ser Cys Thr Thr Asn Ser Gly Ala Ile Thr Leu
    50                  55                  60

Asp Ala Asn Trp Arg Trp Val His Gly Val Asn Thr Ser Thr Asn Cys
65                  70                  75                  80

Tyr Thr Gly Asn Thr Trp Asn Thr Ala Ile Cys Asp Thr Asp Ala Ser
                85                  90                  95

Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
        115                 120                 125

Ser Asn Val Gly Ser Arg Thr Tyr Leu Met Ala Asp Asn Thr His Tyr
    130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Ala Gly Gln Ala Asn Val Glu Gly Trp Thr Pro Ser Ser Asn
    210                 215                 220
```

-continued

| | | | | | | | | | | | | | | |
|---|---|---|---|---|---|---|---|---|---|---|---|---|---|---|
Asn Ala Asn Thr Gly Leu Gly Asn His Gly Ala Cys Cys Ala Glu Leu
225                 230                 235                 240

Asp Ile Trp Glu Ala Asn Ser Ile Ser Glu Ala Leu Thr Pro His Pro
            245                 250                 255

Cys Asp Thr Pro Gly Leu Ser Val Cys Thr Thr Asp Ala Cys Gly Gly
        260                 265                 270

Thr Tyr Ser Ser Asp Arg Tyr Ala Gly Thr Cys Asp Pro Asp Gly Cys
    275                 280                 285

Asp Phe Asn Pro Tyr Arg Leu Gly Val Thr Asp Phe Tyr Gly Ser Gly
290                 295                 300

Lys Thr Val Asp Thr Thr Lys Pro Ile Thr Val Val Thr Gln Phe Val
305                 310                 315                 320

Thr Asp Asp Gly Thr Ser Thr Gly Thr Leu Ser Glu Ile Arg Arg Tyr
            325                 330                 335

Tyr Val Gln Asn Gly Val Val Ile Pro Gln Pro Ser Ser Lys Ile Ser
        340                 345                 350

Gly Val Ser Gly Asn Val Ile Asn Ser Asp Phe Cys Asp Ala Glu Ile
    355                 360                 365

Ser Thr Phe Gly Glu Thr Ala Ser Phe Ser Lys His Gly Gly Leu Ala
370                 375                 380

Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
            405                 410                 415

Thr Asn Ala Thr Gly Thr Pro Gly Ala Ala Arg Gly Ser Cys Pro Thr
        420                 425                 430

Thr Ser Gly Asp Pro Lys Thr Val Glu Ser Gln Ser Gly Ser Ser Tyr
    435                 440                 445

Val Thr Phe Ser Asp Ile Arg Val Gly Pro Phe Asn Ser Thr Phe Ser
450                 455                 460

Gly Gly Ser Ser Gly Gly Gly Ser Gly Gly Gly Ser Gly Gly
465                 470                 475                 480

Gly Gly Ser Gly Gly Gly Ser Gly Gly Gly Ser Ala Ala His
        485                 490                 495

Trp Gly Gln Cys Gly Gly Gln Gly Trp Thr Gly Pro Thr Thr Cys Ala
    500                 505                 510

Ser Gly Thr Thr Cys Thr Val Val Asn Pro Tyr Tyr Ser Gln Cys Leu
        515                 520                 525

Ser Glu Lys Asp Glu Leu
        530

<210> SEQ ID NO 7
<211> LENGTH: 1623
<212> TYPE: DNA
<213> ORGANISM: Artificial Sequence
<220> FEATURE:
<223> OTHER INFORMATION: dicot optimized CBH1 gene with modified linker
      (pSM451)
<220> FEATURE:
<221> NAME/KEY: CDS
<222> LOCATION: (1)..(1623)

<400> SEQUENCE: 7 atg gga ttc gtg ctt ttc tct cag ctt cct tct ttc ctt ctt gtg tct     48
Met Gly Phe Val Leu Phe Ser Gln Leu Pro Ser Phe Leu Leu Val Ser
1               5                   10                  15

| | | |
|---|---|---|
| act ctt ctt ctt ttc ctt gtg att tct cac tct tgc agg gct caa cag<br>Thr Leu Leu Leu Phe Leu Val Ile Ser His Ser Cys Arg Ala Gln Gln<br>       20                      25                30 | | 96 |
| att gga act tac act gct gag act cac cca tct ttg tct tgg tct act<br>Ile Gly Thr Tyr Thr Ala Glu Thr His Pro Ser Leu Ser Trp Ser Thr<br>            35                      40              45 | | 144 |
| tgc aag tct ggt gga tct tgc act act aac tct ggt gct att act ctt<br>Cys Lys Ser Gly Gly Ser Cys Thr Thr Asn Ser Gly Ala Ile Thr Leu<br> 50                      55                      60 | | 192 |
| gat gct aat tgg aga tgg gtg cac ggt gtt aac act tct act aac tgc<br>Asp Ala Asn Trp Arg Trp Val His Gly Val Asn Thr Ser Thr Asn Cys<br>65                 70                    75               80 | | 240 |
| tac act gga aac act tgg aac act gct att tgc gat act gat gct tct<br>Tyr Thr Gly Asn Thr Trp Asn Thr Ala Ile Cys Asp Thr Asp Ala Ser<br>                85                      90              95 | | 288 |
| tgc gct caa gat tgc gct ctt gat ggt gct gat tac tca gga act tac<br>Cys Ala Gln Asp Cys Ala Leu Asp Gly Ala Asp Tyr Ser Gly Thr Tyr<br>                  100                      105             110 | | 336 |
| gga att act act tct gga aac tct ctt agg ctt aac ttc gtg act gga<br>Gly Ile Thr Thr Ser Gly Asn Ser Leu Arg Leu Asn Phe Val Thr Gly<br>            115                      120                 125 | | 384 |
| tct aat gtg gga tct agg act tac ctt atg gct gat aac act cac tac<br>Ser Asn Val Gly Ser Arg Thr Tyr Leu Met Ala Asp Asn Thr His Tyr<br>130                      135                      140 | | 432 |
| cag att ttc gat ctt ctt aac cag gaa ttc act ttc act gtt gat gtg<br>Gln Ile Phe Asp Leu Leu Asn Gln Glu Phe Thr Phe Thr Val Asp Val<br>145                    150                      155                160 | | 480 |
| tct cat ctt cca tgc gga ctt aac ggt gct ctt tac ttc gtg act atg<br>Ser His Leu Pro Cys Gly Leu Asn Gly Ala Leu Tyr Phe Val Thr Met<br>                  165                      170                 175 | | 528 |
| gat gct gat ggt gga gtt tct aag tac cca aac aac aag gct ggt gct<br>Asp Ala Asp Gly Gly Val Ser Lys Tyr Pro Asn Asn Lys Ala Gly Ala<br>                     180                      185                 190 | | 576 |
| caa tat ggt gtt gga tac tgc gat tct caa tgc cca agg gat ctt aag<br>Gln Tyr Gly Val Gly Tyr Cys Asp Ser Gln Cys Pro Arg Asp Leu Lys<br>            195                      200                 205 | | 624 |
| ttc att gct gga cag gct aat gtt gaa gga tgg act cca tct tct aac<br>Phe Ile Ala Gly Gln Ala Asn Val Glu Gly Trp Thr Pro Ser Ser Asn<br>            210                      215                 220 | | 672 |
| aac gct aac act gga ctt gga aat cat ggt gct tgc tgc gct gaa ctt<br>Asn Ala Asn Thr Gly Leu Gly Asn His Gly Ala Cys Cys Ala Glu Leu<br>225                      230                      235                240 | | 720 |
| gat att tgg gag gct aac tct att tct gag gct ctt act cca cat cca<br>Asp Ile Trp Glu Ala Asn Ser Ile Ser Glu Ala Leu Thr Pro His Pro<br>                  245                      250               255 | | 768 |
| tgc gat act cca gga ctt tct gtg tgc act act gat gct tgt gga gga<br>Cys Asp Thr Pro Gly Leu Ser Val Cys Thr Thr Asp Ala Cys Gly Gly<br>                     260                      265                 270 | | 816 |
| act tac tct tct gat aga tac gct gga act tgc gat cca gat gga tgc<br>Thr Tyr Ser Ser Asp Arg Tyr Ala Gly Thr Cys Asp Pro Asp Gly Cys<br>            275                      280                 285 | | 864 |
| gat ttc aac cca tac agg ctt gga gtg act gat ttc tac gga tct gga<br>Asp Phe Asn Pro Tyr Arg Leu Gly Val Thr Asp Phe Tyr Gly Ser Gly<br>                  290                      295               300 | | 912 |
| aag act gtg gat aca act aag cca att act gtg gtg act cag ttc gtg<br>Lys Thr Val Asp Thr Thr Lys Pro Ile Thr Val Val Thr Gln Phe Val<br>305                      310                      315                320 | | 960 |
| act gat gat gga act tct act gga act ctt tct gag att aga agg tac<br>Thr Asp Asp Gly Thr Ser Thr Gly Thr Leu Ser Glu Ile Arg Arg Tyr<br>                  325                      330               335 | | 1008 |

```
tac gtt cag aac ggt gtt gtt att cca cag cca tct tct aag att tct      1056
Tyr Val Gln Asn Gly Val Val Ile Pro Gln Pro Ser Ser Lys Ile Ser
                340                 345                 350 ggt gtg tct gga aac gtg att aac tct gat ttc tgt gat gct gag att      1104
Gly Val Ser Gly Asn Val Ile Asn Ser Asp Phe Cys Asp Ala Glu Ile
            355                 360                 365 tct act ttc gga gag act gct tct ttt tct aag cac ggt gga ctt gct      1152
Ser Thr Phe Gly Glu Thr Ala Ser Phe Ser Lys His Gly Gly Leu Ala
        370                 375                 380 aaa atg gga gct gga atg gaa gct gga atg gtg ctt gtg atg tct ctt      1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca      1248
Trp Asp Asp Tyr Ser Val Asn Met Leu Trp Leu Asp Ser Thr Tyr Pro
                405                 410                 415 act aac gct act ggt act cca ggt gct gct aga gga tct tgc cca act      1296
Thr Asn Ala Thr Gly Thr Pro Gly Ala Ala Arg Gly Ser Cys Pro Thr
            420                 425                 430 act tct ggt gat cct aag act gtg gag tct cag tct gga tct tct tac      1344
Thr Ser Gly Asp Pro Lys Thr Val Glu Ser Gln Ser Gly Ser Ser Tyr
        435                 440                 445 gtg act ttc tct gat att aga gtg gga cca ttc aac tct act ttc tct      1392
Val Thr Phe Ser Asp Ile Arg Val Gly Pro Phe Asn Ser Thr Phe Ser
    450                 455                 460 ggt ggt tct tct act gct cca gct cca gct cct gca cca gca cct gct      1440
Gly Gly Ser Ser Thr Ala Pro Ala Pro Ala Pro Ala Pro Ala Pro Ala
465                 470                 475                 480 cca gca cca gca cct gca cct gct cca gct cca gca cca gct cca gct      1488
Pro Ala Pro Ala Pro Ala Pro Ala Pro Ala Pro Ala Pro Ala Pro Ala
                485                 490                 495 cca gct cct gct gct cat tgg gga caa tgt gga gga caa gga tgg act      1536
Pro Ala Pro Ala Ala His Trp Gly Gln Cys Gly Gly Gln Gly Trp Thr
            500                 505                 510 gga cca act act tgt gct tct gga act act tgc act gtg gtg aac cct      1584
Gly Pro Thr Thr Cys Ala Ser Gly Thr Thr Cys Thr Val Val Asn Pro
        515                 520                 525 tac tac tct cag tgc ctt tct gag aag gat gag ctt tga                  1623
Tyr Tyr Ser Gln Cys Leu Ser Glu Lys Asp Glu Leu
    530                 535                 540

<210> SEQ ID NO 8
<211> LENGTH: 540
<212> TYPE: PRT
<213> ORGANISM: Artificial Sequence
<220> FEATURE:
<223> OTHER INFORMATION: Synthetic Construct

<400> SEQUENCE: 8

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Gln Gln
                20                  25                  30

Ile Gly Thr Tyr Thr Ala Glu Thr His Pro Ser Leu Ser Trp Ser Thr
            35                  40                  45

Cys Lys Ser Gly Gly Ser Cys Thr Thr Asn Ser Gly Ala Ile Thr Leu
        50                  55                  60

Asp Ala Asn Trp Arg Trp Val His Gly Val Asn Thr Ser Thr Asn Cys
65                  70                  75                  80

Tyr Thr Gly Asn Thr Trp Asn Thr Ala Ile Cys Asp Thr Asp Ala Ser
```

```
                        85                  90                  95
Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
            115                 120                 125

Ser Asn Val Gly Ser Arg Thr Tyr Leu Met Ala Asp Asn Thr His Tyr
    130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
            195                 200                 205

Phe Ile Ala Gly Gln Ala Asn Val Glu Gly Trp Thr Pro Ser Ser Asn
    210                 215                 220

Asn Ala Asn Thr Gly Leu Gly Asn His Gly Ala Cys Cys Ala Glu Leu
225                 230                 235                 240

Asp Ile Trp Glu Ala Asn Ser Ile Ser Glu Ala Leu Thr Pro His Pro
                245                 250                 255

Cys Asp Thr Pro Gly Leu Ser Val Cys Thr Thr Asp Ala Cys Gly Gly
            260                 265                 270

Thr Tyr Ser Ser Asp Arg Tyr Ala Gly Thr Cys Asp Pro Asp Gly Cys
            275                 280                 285

Asp Phe Asn Pro Tyr Arg Leu Gly Val Thr Asp Phe Tyr Gly Ser Gly
    290                 295                 300

Lys Thr Val Asp Thr Thr Lys Pro Ile Thr Val Val Thr Gln Phe Val
305                 310                 315                 320

Thr Asp Asp Gly Thr Ser Thr Gly Thr Leu Ser Glu Ile Arg Arg Tyr
                325                 330                 335

Tyr Val Gln Asn Gly Val Val Ile Pro Gln Pro Ser Ser Lys Ile Ser
            340                 345                 350

Gly Val Ser Gly Asn Val Ile Asn Ser Asp Phe Cys Asp Ala Glu Ile
            355                 360                 365

Ser Thr Phe Gly Glu Thr Ala Ser Phe Ser Lys His Gly Gly Leu Ala
    370                 375                 380

Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
                405                 410                 415

Thr Asn Ala Thr Gly Thr Pro Gly Ala Ala Arg Gly Ser Cys Pro Thr
            420                 425                 430

Thr Ser Gly Asp Pro Lys Thr Val Glu Ser Gln Ser Gly Ser Ser Tyr
            435                 440                 445

Val Thr Phe Ser Asp Ile Arg Val Gly Pro Phe Asn Ser Thr Phe Ser
    450                 455                 460

Gly Gly Ser Ser Thr Ala Pro Ala Pro Ala Pro Ala Pro Ala Pro Ala
465                 470                 475                 480

Pro Ala Pro Ala Pro Ala Pro Ala Pro Ala Pro Ala Pro Ala Pro Ala
                485                 490                 495

Pro Ala Pro Ala Ala His Trp Gly Gln Cys Gly Gly Gln Gly Trp Thr
            500                 505                 510
```

-continued

```
Gly Pro Thr Thr Cys Ala Ser Gly Thr Thr Cys Thr Val Val Asn Pro
            515                 520                 525

Tyr Tyr Ser Gln Cys Leu Ser Glu Lys Asp Glu Leu
            530                 535                 540

<210> SEQ ID NO 9
<211> LENGTH: 1623
<212> TYPE: DNA
<213> ORGANISM: Artificial Sequence
<220> FEATURE:
<223> OTHER INFORMATION: dicot optimized CBH1 gene with modified lnker
      (pSM452)
<220> FEATURE:
<221> NAME/KEY: CDS
<222> LOCATION: (1)..(1623)

<400> SEQUENCE: 9 atg gga ttc gtg ctt ttc tct cag ctt cct tct ttc ctt ctt gtg tct      48
Met Gly Phe Val Leu Phe Ser Gln Leu Pro Ser Phe Leu Leu Val Ser
1               5                   10                  15 act ctt ctt ctt ttc ctt gtg att tct cac tct tgc agg gct caa cag      96
Thr Leu Leu Leu Phe Leu Val Ile Ser His Ser Cys Arg Ala Gln Gln
                20                  25                  30 att gga act tac act gct gag act cac cca tct ttg tct tgg tct act     144
Ile Gly Thr Tyr Thr Ala Glu Thr His Pro Ser Leu Ser Trp Ser Thr
            35                  40                  45 tgc aag tct ggt gga tct tgc act act aac tct ggt gct att act ctt     192
Cys Lys Ser Gly Gly Ser Cys Thr Thr Asn Ser Gly Ala Ile Thr Leu
        50                  55                  60 gat gct aat tgg aga tgg gtg cac ggt gtt aac act tct act aac tgc     240
Asp Ala Asn Trp Arg Trp Val His Gly Val Asn Thr Ser Thr Asn Cys
65                  70                  75                  80 tac act gga aac act tgg aac act gct att tgc gat act gat gct tct     288
Tyr Thr Gly Asn Thr Trp Asn Thr Ala Ile Cys Asp Thr Asp Ala Ser
                85                  90                  95 tgc gct caa gat tgc gct ctt gat ggt gct gat tac tca gga act tac     336
Cys Ala Gln Asp Cys Ala Leu Asp Gly Ala Asp Tyr Ser Gly Thr Tyr
                100                 105                 110 gga att act act tct gga aac tct ctt agg ctt aac ttc gtg act gga     384
Gly Ile Thr Thr Ser Gly Asn Ser Leu Arg Leu Asn Phe Val Thr Gly
            115                 120                 125 tct aat gtg gga tct agg act tac ctt atg gct gat aac act cac tac     432
Ser Asn Val Gly Ser Arg Thr Tyr Leu Met Ala Asp Asn Thr His Tyr
        130                 135                 140 cag att ttc gat ctt ctt aac cag gaa ttc act ttc act gtt gat gtg     480
Gln Ile Phe Asp Leu Leu Asn Gln Glu Phe Thr Phe Thr Val Asp Val
145                 150                 155                 160 tct cat ctt cca tgc gga ctt aac ggt gct ctt tac ttc gtg act atg     528
Ser His Leu Pro Cys Gly Leu Asn Gly Ala Leu Tyr Phe Val Thr Met
                165                 170                 175 gat gct gat ggt gga gtt tct aag tac cca aac aac aag gct ggt gct     576
Asp Ala Asp Gly Gly Val Ser Lys Tyr Pro Asn Asn Lys Ala Gly Ala
            180                 185                 190 caa tat ggt gtt gga tac tgc gat tct caa tgc cca agg gat ctt aag     624
Gln Tyr Gly Val Gly Tyr Cys Asp Ser Gln Cys Pro Arg Asp Leu Lys
        195                 200                 205 ttc att gct gga cag gct aat gtt gaa gga tgg act cca tct tct aac     672
Phe Ile Ala Gly Gln Ala Asn Val Glu Gly Trp Thr Pro Ser Ser Asn
        210                 215                 220 aac gct aac act gga ctt gga aat cat ggt gct tgc tgc gct gaa ctt     720
Asn Ala Asn Thr Gly Leu Gly Asn His Gly Ala Cys Cys Ala Glu Leu
```

```
                225                 230                 235                 240
gat att tgg gag gct aac tct att tct gag gct ctt act cca cat cca            768
Asp Ile Trp Glu Ala Asn Ser Ile Ser Glu Ala Leu Thr Pro His Pro
                245                 250                 255 tgc gat act cca gga ctt tct gtg tgc act act gat gct tgt gga gga            816
Cys Asp Thr Pro Gly Leu Ser Val Cys Thr Thr Asp Ala Cys Gly Gly
                260                 265                 270 act tac tct tct gat aga tac gct gga act tgc gat cca gat gga tgc            864
Thr Tyr Ser Ser Asp Arg Tyr Ala Gly Thr Cys Asp Pro Asp Gly Cys
                275                 280                 285 gat ttc aac cca tac agg ctt gga gtg act gat ttc tac gga tct gga            912
Asp Phe Asn Pro Tyr Arg Leu Gly Val Thr Asp Phe Tyr Gly Ser Gly
        290                 295                 300 aag act gtg gat aca act aag cca att act gtg gtg act cag ttc gtg            960
Lys Thr Val Asp Thr Thr Lys Pro Ile Thr Val Val Thr Gln Phe Val
305                 310                 315                 320 act gat gat gga act tct act gga act ctt tct gag att aga agg tac           1008
Thr Asp Asp Gly Thr Ser Thr Gly Thr Leu Ser Glu Ile Arg Arg Tyr
                325                 330                 335 tac gtt cag aac ggt gtt gtt att cca cag cca tct tct aag att tct           1056
Tyr Val Gln Asn Gly Val Val Ile Pro Gln Pro Ser Ser Lys Ile Ser
                340                 345                 350 ggt gtg tct gga aac gtg att aac tct gat ttc tgt gat gct gag att           1104
Gly Val Ser Gly Asn Val Ile Asn Ser Asp Phe Cys Asp Ala Glu Ile
                355                 360                 365 tct act ttc gga gag act gct tct ttt tct aag cac ggt gga ctt gct           1152
Ser Thr Phe Gly Glu Thr Ala Ser Phe Ser Lys His Gly Gly Leu Ala
        370                 375                 380 aaa atg gga gct gga atg gaa gct gga atg gtg ctt gtg atg tct ctt           1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca           1248
Trp Asp Asp Tyr Ser Val Asn Met Leu Trp Leu Asp Ser Thr Tyr Pro
                405                 410                 415 act aac gct act ggt act cca ggt gct gct aga gga tct tgc cca act           1296
Thr Asn Ala Thr Gly Thr Pro Gly Ala Ala Arg Gly Ser Cys Pro Thr
                420                 425                 430 act tct ggt gat cct aag act gtg gag tct cag tct gga tct tct tac           1344
Thr Ser Gly Asp Pro Lys Thr Val Glu Ser Gln Ser Gly Ser Ser Tyr
        435                 440                 445 gtg act ttc tct gat att aga gtg gga cca ttc aac tct act ttc tct           1392
Val Thr Phe Ser Asp Ile Arg Val Gly Pro Phe Asn Ser Thr Phe Ser
450                 455                 460 ggt ggt tct tct act gtt cca gtt cca gtt cct gtg cca gtg cct gtt           1440
Gly Gly Ser Ser Thr Val Pro Val Pro Val Pro Val Pro Val Pro Val
465                 470                 475                 480 cct gtt cct gtt cca gtg cca gtt cca gtg cct gtt cca gtt cct gtg           1488
Pro Val Pro Val Pro Val Pro Val Pro Val Pro Val Pro Val Pro Val
                485                 490                 495 cct gtt cct gct gct cat tgg gga caa tgt gga gga caa gga tgg act           1536
Pro Val Pro Ala Ala His Trp Gly Gln Cys Gly Gly Gln Gly Trp Thr
                500                 505                 510 gga cca act act tgt gct tct gga act act tgc act gtg gtg aac cct           1584
Gly Pro Thr Thr Cys Ala Ser Gly Thr Thr Cys Thr Val Val Asn Pro
        515                 520                 525 tac tac tct cag tgc ctt tct gag aag gat gag ctt tga                       1623
Tyr Tyr Ser Gln Cys Leu Ser Glu Lys Asp Glu Leu
                530                 535                 540
```

```
<210> SEQ ID NO 10
<211> LENGTH: 540
<212> TYPE: PRT
<213> ORGANISM: Artificial Sequence
<220> FEATURE:
<223> OTHER INFORMATION: Synthetic Construct

<400> SEQUENCE: 10

Met Gly Phe Val Leu Phe Ser Gln Leu Pro Ser Phe Leu Val Ser
1               5                   10                  15

Thr Leu Leu Leu Phe Leu Val Ile Ser His Ser Cys Arg Ala Gln Gln
            20                  25                  30

Ile Gly Thr Tyr Thr Ala Glu Thr His Pro Ser Leu Ser Trp Ser Thr
        35                  40                  45

Cys Lys Ser Gly Gly Ser Cys Thr Thr Asn Ser Gly Ala Ile Thr Leu
    50                  55                  60

Asp Ala Asn Trp Arg Trp Val His Gly Val Asn Thr Ser Thr Asn Cys
65                  70                  75                  80

Tyr Thr Gly Asn Thr Trp Asn Thr Ala Ile Cys Asp Thr Asp Ala Ser
                85                  90                  95

Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
        115                 120                 125

Ser Asn Val Gly Ser Arg Thr Tyr Leu Met Ala Asp Asn Thr His Tyr
130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Ala Gly Gln Ala Asn Val Glu Gly Trp Thr Pro Ser Ser Asn
210                 215                 220

Asn Ala Asn Thr Gly Leu Gly Asn His Gly Ala Cys Cys Ala Glu Leu
225                 230                 235                 240

Asp Ile Trp Glu Ala Asn Ser Ile Ser Glu Ala Leu Thr Pro His Pro
                245                 250                 255

Cys Asp Thr Pro Gly Leu Ser Val Cys Thr Thr Asp Ala Cys Gly Gly
            260                 265                 270

Thr Tyr Ser Ser Asp Arg Tyr Ala Gly Thr Cys Asp Pro Asp Gly Cys
        275                 280                 285

Asp Phe Asn Pro Tyr Arg Leu Gly Val Thr Asp Phe Tyr Gly Ser Gly
290                 295                 300

Lys Thr Val Asp Thr Thr Lys Pro Ile Thr Val Val Thr Gln Phe Val
305                 310                 315                 320

Thr Asp Asp Gly Thr Ser Thr Gly Thr Leu Ser Glu Ile Arg Arg Tyr
                325                 330                 335

Tyr Val Gln Asn Gly Val Val Ile Pro Gln Pro Ser Ser Lys Ile Ser
            340                 345                 350

Gly Val Ser Gly Asn Val Ile Asn Ser Asp Phe Cys Asp Ala Glu Ile
        355                 360                 365

Ser Thr Phe Gly Glu Thr Ala Ser Phe Ser Lys His Gly Gly Leu Ala
```

```
              370                 375                 380
Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
                405                 410                 415

Thr Asn Ala Thr Gly Thr Pro Gly Ala Ala Arg Gly Ser Cys Pro Thr
                420                 425                 430

Thr Ser Gly Asp Pro Lys Thr Val Glu Ser Gln Ser Gly Ser Ser Tyr
                435                 440                 445

Val Thr Phe Ser Asp Ile Arg Val Gly Pro Phe Asn Ser Thr Phe Ser
                450                 455                 460

Gly Gly Ser Ser Thr Val Pro Val Pro Val Pro Val Pro Val Pro Val
465                 470                 475                 480

Pro Val Pro Val Pro Val Pro Val Pro Val Pro Val Pro Val Pro Val
                485                 490                 495

Pro Val Pro Ala Ala His Trp Gly Gln Cys Gly Gly Gln Gly Trp Thr
                500                 505                 510

Gly Pro Thr Thr Cys Ala Ser Gly Thr Thr Cys Thr Val Val Asn Pro
                515                 520                 525

Tyr Tyr Ser Gln Cys Leu Ser Glu Lys Asp Glu Leu
                530                 535                 540

<210> SEQ ID NO 11
<211> LENGTH: 1623
<212> TYPE: DNA
<213> ORGANISM: Artificial Sequence
<220> FEATURE:
<223> OTHER INFORMATION: dicot optimized CBH1 with modified linker
      (pSM453)
<220> FEATURE:
<221> NAME/KEY: CDS
<222> LOCATION: (1)..(1623)

<400> SEQUENCE: 11 atg gga ttc gtg ctt ttc tct cag ctt cct tct ttc ctt ctt gtg tct    48
Met Gly Phe Val Leu Phe Ser Gln Leu Pro Ser Phe Leu Leu Val Ser
1               5                  10                  15 act ctt ctt ctt ttc ctt gtg att tct cac tct tgc agg gct caa cag    96
Thr Leu Leu Leu Phe Leu Val Ile Ser His Ser Cys Arg Ala Gln Gln
            20                  25                  30 att gga act tac act gct gag act cac cca tct ttg tct tgg tct act   144
Ile Gly Thr Tyr Thr Ala Glu Thr His Pro Ser Leu Ser Trp Ser Thr
        35                  40                  45 tgc aag tct ggt gga tct tgc act act aac tct ggt gct att act ctt   192
Cys Lys Ser Gly Gly Ser Cys Thr Thr Asn Ser Gly Ala Ile Thr Leu
    50                  55                  60 gat gct aat tgg aga tgg gtg cac ggt gtt aac act tct act aac tgc   240
Asp Ala Asn Trp Arg Trp Val His Gly Val Asn Thr Ser Thr Asn Cys
65                  70                  75                  80 tac act gga aac act tgg aac act gct att tgc gat act gat gct tct   288
Tyr Thr Gly Asn Thr Trp Asn Thr Ala Ile Cys Asp Thr Asp Ala Ser
                85                  90                  95 tgc gct caa gat tgc gct ctt gat ggt gct gat tac tca gga act tac   336
Cys Ala Gln Asp Cys Ala Leu Asp Gly Ala Asp Tyr Ser Gly Thr Tyr
            100                 105                 110 gga att act act tct gga aac tct ctt agg ctt aac ttc gtg act gga   384
Gly Ile Thr Thr Ser Gly Asn Ser Leu Arg Leu Asn Phe Val Thr Gly
        115                 120                 125 tct aat gtg gga tct agg act tac ctt atg gct gat aac act cac tac   432
```

```
Ser Asn Val Gly Ser Arg Thr Tyr Leu Met Ala Asp Asn Thr His Tyr
        130                 135                 140 cag att ttc gat ctt ctt aac cag gaa ttc act ttc act gtt gat gtg      480
Gln Ile Phe Asp Leu Leu Asn Gln Glu Phe Thr Phe Thr Val Asp Val
145                 150                 155                 160 tct cat ctt cca tgc gga ctt aac ggt gct ctt tac ttc gtg act atg      528
Ser His Leu Pro Cys Gly Leu Asn Gly Ala Leu Tyr Phe Val Thr Met
                165                 170                 175 gat gct gat ggt gga gtt tct aag tac cca aac aac aag gct ggt gct      576
Asp Ala Asp Gly Gly Val Ser Lys Tyr Pro Asn Asn Lys Ala Gly Ala
            180                 185                 190 caa tat ggt gtt gga tac tgc gat tct caa tgc cca agg gat ctt aag      624
Gln Tyr Gly Val Gly Tyr Cys Asp Ser Gln Cys Pro Arg Asp Leu Lys
        195                 200                 205 ttc att gct gga cag gct aat gtt gaa gga tgg act cca tct tct aac      672
Phe Ile Ala Gly Gln Ala Asn Val Glu Gly Trp Thr Pro Ser Ser Asn
    210                 215                 220 aac gct aac act gga ctt gga aat cat ggt gct tgc tgc gct gaa ctt      720
Asn Ala Asn Thr Gly Leu Gly Asn His Gly Ala Cys Cys Ala Glu Leu
225                 230                 235                 240 gat att tgg gag gct aac tct att tct gag gct ctt act cca cat cca      768
Asp Ile Trp Glu Ala Asn Ser Ile Ser Glu Ala Leu Thr Pro His Pro
                245                 250                 255 tgc gat act cca gga ctt tct gtg tgc act act gat gct tgt gga gga      816
Cys Asp Thr Pro Gly Leu Ser Val Cys Thr Thr Asp Ala Cys Gly Gly
            260                 265                 270 act tac tct tct gat aga tac gct gga act tgc gat cca gat gga tgc      864
Thr Tyr Ser Ser Asp Arg Tyr Ala Gly Thr Cys Asp Pro Asp Gly Cys
        275                 280                 285 gat ttc aac cca tac agg ctt gga gtg act gat ttc tac gga tct gga      912
Asp Phe Asn Pro Tyr Arg Leu Gly Val Thr Asp Phe Tyr Gly Ser Gly
    290                 295                 300 aag act gtg gat aca act aag cca att act gtg gtg act cag ttc gtg      960
Lys Thr Val Asp Thr Thr Lys Pro Ile Thr Val Val Thr Gln Phe Val
305                 310                 315                 320 act gat gat gga act tct act gga act ctt tct gag att aga agg tac     1008
Thr Asp Asp Gly Thr Ser Thr Gly Thr Leu Ser Glu Ile Arg Arg Tyr
                325                 330                 335 tac gtt cag aac ggt gtt gtt att cca cag cca tct tct aag att tct     1056
Tyr Val Gln Asn Gly Val Val Ile Pro Gln Pro Ser Ser Lys Ile Ser
            340                 345                 350 ggt gtg tct gga aac gtg att aac tct gat ttc tgt gat gct gag att     1104
Gly Val Ser Gly Asn Val Ile Asn Ser Asp Phe Cys Asp Ala Glu Ile
        355                 360                 365 tct act ttc gga gag act gct tct ttt tct aag cac ggt gga ctt gct     1152
Ser Thr Phe Gly Glu Thr Ala Ser Phe Ser Lys His Gly Gly Leu Ala
    370                 375                 380 aaa atg gga gct gga atg gaa gct gga atg gtg ctt gtg atg tct ctt     1200
Lys Met Gly Ala Gly Met Glu Ala Gly Met Val Leu Val Met Ser Leu
385                 390                 395                 400 tgg gat gat tac tct gtg aac atg ctt tgg ctt gat tct act tac cca     1248
Trp Asp Asp Tyr Ser Val Asn Met Leu Trp Leu Asp Ser Thr Tyr Pro
                405                 410                 415 act aac gct act ggt act cca ggt gct gct aga gga tct tgc cca act     1296
Thr Asn Ala Thr Gly Thr Pro Gly Ala Ala Arg Gly Ser Cys Pro Thr
            420                 425                 430 act tct ggt gat cct aag act gtg gag tct cag tct gga tct tct tac     1344
Thr Ser Gly Asp Pro Lys Thr Val Glu Ser Gln Ser Gly Ser Ser Tyr
        435                 440                 445
```

```
gtg act ttc tct gat att aga gtg gga cca ttc aac tct act ttc tct    1392
Val Thr Phe Ser Asp Ile Arg Val Gly Pro Phe Asn Ser Thr Phe Ser
450                 455                 460 ggt ggt tct tct act tct cca tct cca tca cct tcc cca tct cca agt    1440
Gly Gly Ser Ser Thr Ser Pro Ser Pro Ser Pro Ser Pro Ser Pro Ser
465                 470                 475                 480 cca agt cca tct cct tct cca agt cct tca cca tca cct agt cct tca    1488
Pro Ser Pro Ser Pro Ser Pro Ser Pro Ser Pro Ser Pro Ser Pro Ser
                485                 490                 495 cct tct cca gct gct cat tgg gga caa tgt gga gga caa gga tgg act    1536
Pro Ser Pro Ala Ala His Trp Gly Gln Cys Gly Gly Gln Gly Trp Thr
                500                 505                 510 gga cca act act tgt gct tct gga act act tgc act gtg gtg aac cct    1584
Gly Pro Thr Thr Cys Ala Ser Gly Thr Thr Cys Thr Val Val Asn Pro
                515                 520                 525 tac tac tct cag tgc ctt tct gag aag gat gag ctt tga                1623
Tyr Tyr Ser Gln Cys Leu Ser Glu Lys Asp Glu Leu
                530                 535                 540

<210> SEQ ID NO 12
<211> LENGTH: 540
<212> TYPE: PRT
<213> ORGANISM: Artificial Sequence
<220> FEATURE:
<223> OTHER INFORMATION: Synthetic Construct

<400> SEQUENCE: 12

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala Gln Gln
                20                  25                  30

Ile Gly Thr Tyr Thr Ala Glu Thr His Pro Ser Leu Ser Trp Ser Thr
            35                  40                  45

Cys Lys Ser Gly Gly Ser Cys Thr Thr Asn Ser Gly Ala Ile Thr Leu
        50                  55                  60

Asp Ala Asn Trp Arg Trp Val His Gly Val Asn Thr Ser Thr Asn Cys
65                  70                  75                  80

Tyr Thr Gly Asn Thr Trp Asn Thr Ala Ile Cys Asp Thr Asp Ala Ser
                85                  90                  95

Cys Ala Gln Asp Cys Ala Leu Asp Gly Ala Asp Tyr Ser Gly Thr Tyr
            100                 105                 110

Gly Ile Thr Thr Ser Gly Asn Ser Leu Arg Leu Asn Phe Val Thr Gly
        115                 120                 125

Ser Asn Val Gly Ser Arg Thr Tyr Leu Met Ala Asp Asn Thr His Tyr
    130                 135                 140

Gln Ile Phe Asp Leu Leu Asn Gln Glu Phe Thr Phe Thr Val Asp Val
145                 150                 155                 160

Ser His Leu Pro Cys Gly Leu Asn Gly Ala Leu Tyr Phe Val Thr Met
                165                 170                 175

Asp Ala Asp Gly Gly Val Ser Lys Tyr Pro Asn Asn Lys Ala Gly Ala
            180                 185                 190

Gln Tyr Gly Val Gly Tyr Cys Asp Ser Gln Cys Pro Arg Asp Leu Lys
        195                 200                 205

Phe Ile Ala Gly Gln Ala Asn Val Glu Gly Trp Thr Pro Ser Ser Asn
    210                 215                 220

Asn Ala Asn Thr Gly Leu Gly Asn His Gly Ala Cys Cys Ala Glu Leu
225                 230                 235                 240
```

-continued

```
Asp Ile Trp Glu Ala Asn Ser Ile Ser Glu Ala Leu Thr Pro His Pro
                245                 250                 255

Cys Asp Thr Pro Gly Leu Ser Val Cys Thr Thr Asp Ala Cys Gly Gly
            260                 265                 270

Thr Tyr Ser Ser Asp Arg Tyr Ala Gly Thr Cys Asp Pro Asp Gly Cys
        275                 280                 285

Asp Phe Asn Pro Tyr Arg Leu Gly Val Thr Asp Phe Tyr Gly Ser Gly
    290                 295                 300

Lys Thr Val Asp Thr Thr Lys Pro Ile Thr Val Val Thr Gln Phe Val
305                 310                 315                 320

Thr Asp Asp Gly Thr Ser Thr Gly Thr Leu Ser Glu Ile Arg Arg Tyr
                325                 330                 335

Tyr Val Gln Asn Gly Val Val Ile Pro Gln Pro Ser Ser Lys Ile Ser
            340                 345                 350

Gly Val Ser Gly Asn Val Ile Asn Ser Asp Phe Cys Asp Ala Glu Ile
        355                 360                 365

Ser Thr Phe Gly Glu Thr Ala Ser Phe Ser Lys His Gly Gly Leu Ala
    370                 375                 380

Lys Met Gly Ala Gly Met Glu Ala Gly Met Val Leu Val Met Ser Leu
385                 390                 395                 400

Trp Asp Asp Tyr Ser Val Asn Met Leu Trp Leu Asp Ser Thr Tyr Pro
                405                 410                 415

Thr Asn Ala Thr Gly Thr Pro Gly Ala Ala Arg Gly Ser Cys Pro Thr
            420                 425                 430

Thr Ser Gly Asp Pro Lys Thr Val Glu Ser Gln Ser Gly Ser Ser Tyr
        435                 440                 445

Val Thr Phe Ser Asp Ile Arg Val Gly Pro Phe Asn Ser Thr Phe Ser
    450                 455                 460

Gly Gly Ser Ser Thr Ser Pro Ser Pro Ser Pro Ser Pro Ser Pro Ser
465                 470                 475                 480

Pro Ser Pro Ser Pro Ser Pro Ser Pro Ser Pro Ser Pro Ser Pro Ser
                485                 490                 495

Pro Ser Pro Ala Ala His Trp Gly Gln Cys Gly Gly Gln Gly Trp Thr
            500                 505                 510

Gly Pro Thr Thr Cys Ala Ser Gly Thr Thr Cys Thr Val Val Asn Pro
        515                 520                 525

Tyr Tyr Ser Gln Cys Leu Ser Glu Lys Asp Glu Leu
    530                 535                 540

<210> SEQ ID NO 13
<211> LENGTH: 30
<212> TYPE: PRT
<213> ORGANISM: Nicotiana

<400> SEQUENCE: 13

Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala
            20                  25                  30

<210> SEQ ID NO 14
<211> LENGTH: 19
<212> TYPE: PRT
<213> ORGANISM: Artificial Sequence
<220> FEATURE:
<223> OTHER INFORMATION: endoplasmic reticulum retention sequence
```

```
<400> SEQUENCE: 14

Met Ala Lys Leu Val Phe Ser Leu Cys Phe Leu Leu Phe Ser Gly Cys
1               5                   10                  15

Cys Phe Ala

<210> SEQ ID NO 15
<211> LENGTH: 10
<212> TYPE: PRT
<213> ORGANISM: Glycine soja

<400> SEQUENCE: 15

Pro Leu Ser Ser Ile Leu Arg Ala Phe Tyr
1               5                   10

<210> SEQ ID NO 16
<211> LENGTH: 19
<212> TYPE: PRT
<213> ORGANISM: Zea mays

<400> SEQUENCE: 16

Met Arg Val Leu Leu Val Ala Leu Ala Leu Leu Ala Leu Ala Ala Ser
1               5                   10                  15

Ala Thr Ser

<210> SEQ ID NO 17
<211> LENGTH: 8
<212> TYPE: PRT
<213> ORGANISM: Hordeum vulgare

<400> SEQUENCE: 17

Asp Glu Leu Lys Ala Glu Ala Lys
1               5

<210> SEQ ID NO 18
<211> LENGTH: 30
<212> TYPE: PRT
<213> ORGANISM: Artificial Sequence
<220> FEATURE:
<223> OTHER INFORMATION: linker sequence

<400> SEQUENCE: 18

Val Pro Val Pro Val Pro Val Pro Val Pro Val Pro Val Pro Val Pro
1               5                   10                  15

Val Pro Val Pro Val Pro Val Pro Val Pro Val Pro Val Pro
                20                  25                  30

<210> SEQ ID NO 19
<211> LENGTH: 30
<212> TYPE: PRT
<213> ORGANISM: Artificial Sequence
<220> FEATURE:
<223> OTHER INFORMATION: linker sequence

<400> SEQUENCE: 19

Ser Pro Ser Pro Ser Pro Ser Pro Ser Pro Ser Pro Ser Pro Ser Pro
1               5                   10                  15

Ser Pro Ser Pro Ser Pro Ser Pro Ser Pro Ser Pro Ser Pro
                20                  25                  30

<210> SEQ ID NO 20
<211> LENGTH: 30
<212> TYPE: PRT
<213> ORGANISM: Artificial Sequence
```

```
<220> FEATURE:
<223> OTHER INFORMATION: linker sequence

<400> SEQUENCE: 20

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: linker sequence

<400> SEQUENCE: 21

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 22
<211> LENGTH: 26
<212> TYPE: PRT
<213> ORGANISM: Artificial Sequence
<220> FEATURE:
<223> OTHER INFORMATION: linker sequence

<400> SEQUENCE: 22

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 23
<211> LENGTH: 6
<212> TYPE: PRT
<213> ORGANISM: Artificial Sequence
<220> FEATURE:
<223> OTHER INFORMATION: ER retention sequence

<400> SEQUENCE: 23

Ser Glu Lys Asp Glu Leu
1               5

<210> SEQ ID NO 24
<211> LENGTH: 620
<212> TYPE: PRT
<213> ORGANISM: Artificial Sequence
<220> FEATURE:
<223> OTHER INFORMATION: evolved glucoamylase BD20082

<400> SEQUENCE: 24

Met Ala Pro Gln Leu Ser Pro Arg Ala Thr Thr Ser Leu Asp Ala Trp
1               5                   10                  15

Leu Ala Ser Glu Thr Thr Val Ser Leu Asn Gly Ile Leu Asp Asn Ile
            20                  25                  30

Gly Ala Ser Gly Ala Tyr Ala Gln Ser Ala Lys Ala Gly Val Val Ile
        35                  40                  45

Ala Ser Pro Ser Thr Ser Ser Pro Asp Tyr Tyr Tyr Thr Trp Thr Arg
    50                  55                  60

Asp Ser Ala Leu Thr Leu Lys Val Leu Ile Asp Leu Phe Arg Asn Gly
```

-continued

```
            65                  70                  75                  80
Asn Val Asp Leu Gln Thr Val Ile Glu Glu Tyr Ile Thr Ala Gln Ala
                85                  90                  95
Tyr Leu Gln Thr Val Ser Asn Pro Ser Gly Asp Leu Ser Ser Gly Ala
               100                 105                 110
Gly Leu Ala Glu Pro Lys Phe Asn Val Asp Met Ser Ala Tyr Thr Gly
               115                 120                 125
Ala Trp Gly Arg Pro Gln Arg Asp Gly Pro Ala Leu Arg Ala Ile Ala
               130                 135                 140
Leu Ile Asp Phe Gly Asn Trp Leu Ile Asp Asn Gly Tyr Ser Ser Tyr
145                150                 155                 160
Ala Val Ser Asn Val Trp Pro Ile Val Arg Asn Asp Leu Ser Tyr Val
               165                 170                 175
Ala Gln Tyr Trp Ser Gln Ser Gly Tyr Asp Leu Trp Glu Glu Val Asn
               180                 185                 190
Ser Met Ser Phe Phe Thr Ile Ala Asn Gln His Arg Ala Leu Val Glu
               195                 200                 205
Gly Ser Thr Phe Ala Gly Arg Val Gly Ala Ser Cys Ser Trp Cys Asp
               210                 215                 220
Ser Gln Ala Pro Gln Ile Leu Cys Tyr Met Gln Asn Phe Trp Thr Gly
225                230                 235                 240
Ser Tyr Ile Asn Ala Asn Thr Gly Gly Arg Ser Gly Lys Asp Ala
               245                 250                 255
Asn Thr Val Leu Ala Ser Ile Ser Thr Phe Asp Pro Glu Ala Thr Cys
               260                 265                 270
Asp Asp Val Thr Phe Gln Pro Cys Ser Ser Arg Ala Leu Ala Asn His
               275                 280                 285
Lys Val Tyr Thr Asp Ser Phe Arg Ser Val Tyr Ser Leu Asp Ser Gly
               290                 295                 300
Ile Ala Glu Gly Val Ala Val Ala Val Gly Arg Tyr Pro Glu Asp Ser
305                310                 315                 320
Tyr Tyr Asn Gly Asn Pro Trp Phe Leu Thr Leu Ala Ala Ala Glu
               325                 330                 335
Gln Leu Tyr Asp Ala Ile Tyr Gln Trp Asn Lys Ile Gly Ser Ile Thr
               340                 345                 350
Ile Thr Ser Thr Ser Leu Ala Phe Phe Asn Asp Val Tyr Ser Ser Ala
               355                 360                 365
Ala Val Gly Thr Tyr Ala Ser Gly Ser Thr Ala Tyr Thr Ala Ile Val
               370                 375                 380
Ser Ala Val Lys Thr Tyr Ala Asp Gly Tyr Val Ser Ile Val Gln Ala
385                390                 395                 400
His Ala Met Thr Asn Gly Ser Leu Ser Glu Gln Phe Asp Lys Ala Ser
               405                 410                 415
Gly Thr Gln Leu Ser Ala Arg Asp Leu Thr Trp Ser Tyr Ala Ala Leu
               420                 425                 430
Leu Thr Ala Asn Met Arg Arg Asn Gly Ile Val Pro Pro Ser Trp Gly
               435                 440                 445
Ala Ala Ser Ala Asn Ser Ile Pro Ser Ser Cys Ser Thr Gly Ser Ala
               450                 455                 460
Thr Gly Thr Tyr Ser Thr Pro Thr Gly Thr Ser Trp Pro Ser Thr Leu
465                470                 475                 480
Thr Ser Gly Thr Ala Gly Thr Thr Thr Thr Ser Ala Thr Thr Thr
               485                 490                 495
```

Ser Thr Ser Val Ser Lys Thr Thr Thr Thr Thr Ser Thr Thr Ser
            500                 505                 510

Cys Thr Thr Pro Thr Ser Val Ala Val Thr Phe Asp Glu Ile Ala Thr
            515                 520                 525

Thr Tyr Tyr Gly Glu Asn Val Tyr Ile Ser Gly Ser Ile Ser Gln Leu
    530                 535                 540

Gly Ser Trp Asp Thr Ser Ser Ala Ile Ala Leu Ser Ala Ser Gln Tyr
545                 550                 555                 560

Thr Ser Ser Asn Asn Leu Trp Phe Val Thr Ile Asn Leu Pro Ala Gly
                565                 570                 575

Thr Thr Phe Gln Tyr Lys Tyr Ile Arg Lys Glu Ser Asp Gly Ser Ile
            580                 585                 590

Val Trp Glu Ser Asp Pro Asn Arg Ser Tyr Thr Val Pro Ser Gly Cys
            595                 600                 605

Gly Val Ser Thr Ala Thr Glu Ser Asp Thr Trp Arg
    610                 615                 620

<210> SEQ ID NO 25
<211> LENGTH: 505
<212> TYPE: PRT
<213> ORGANISM: Artificial Sequence
<220> FEATURE:
<223> OTHER INFORMATION: cellobiohydrolase I with modified linker #9

<400> SEQUENCE: 25

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
    130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

```
Cys Gly Gly Thr Tyr Ser Ser Asp Arg Tyr Ala Thr Cys Asp Pro
            245                 250                 255

Asp Gly Cys Asp Phe Asn Pro Tyr Arg Leu Gly Val Thr Asp Phe Tyr
        260                 265                 270

Gly Ser Gly Lys Thr Val Asp Thr Thr Lys Pro Ile Thr Val Val Thr
            275                 280                 285

Gln Phe Val Thr Asp Asp Gly Thr Ser Thr Gly Thr Leu Ser Glu Ile
        290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
        355                 360                 365

Met Ser Leu Trp Asp Asp Tyr Ser Val Asn Met Leu Trp Leu Asp Ser
    370                 375                 380

Thr Tyr Pro Thr Asn Ala Thr Gly Thr Pro Gly Ala Ala Arg Gly Ser
385                 390                 395                 400

Asn Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Arg Ala Ser Pro Ser Pro Thr Gly
        435                 440                 445

Pro Thr Pro Thr Thr Thr Lys Ala Pro Pro Gly Pro His Ser Pro Pro
450                 455                 460

Pro Thr Leu Ser Pro Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
            500                 505

<210> SEQ ID NO 26
<211> LENGTH: 505
<212> TYPE: PRT
<213> ORGANISM: Artificial Sequence
<220> FEATURE:
<223> OTHER INFORMATION: cellobiohydrolase 1 with modified linker #8

<400> SEQUENCE: 26

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95
```

```
Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
            115                 120                 125

Val Asp Val Ser His Leu Pro Cys Gly Leu Asn Gly Ala Leu Tyr Phe
        130                 135                 140

Val Thr Met Asp Ala Asp Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
            195                 200                 205

Ala Glu Leu Asp Ile Trp Glu Ala Asn Ser Ile Ser Glu Ala Leu Thr
            210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
            275                 280                 285

Gln Phe Val Thr Asp Asp Gly Thr Ser Thr Gly Thr Leu Ser Glu Ile
            290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
            355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Asn Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Arg Ala Ser Pro Ser Pro Thr Gly
            435                 440                 445

Pro Thr Pro Thr Thr Lys Ala Pro Pro Gly Pro His Ser Pro Pro
450                 455                 460

Pro Thr Leu Ser Pro Val Ala Ala His Trp Gly Gln Cys Gly Gly Gln
465                 470                 475                 480

Gly Trp Thr Gly Pro Thr Thr Cys Ala Ser Gly Thr Cys Thr Val
                485                 490                 495

Val Asn Pro Tyr Tyr Ser Gln Cys Leu
            500                 505
```

<210> SEQ ID NO 27
<211> LENGTH: 505
<212> TYPE: PRT
<213> ORGANISM: Artificial Sequence
<220> FEATURE:
<223> OTHER INFORMATION: cellobiohydrolase 1 with modified linker #7

<400> SEQUENCE: 27

```
Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
        275                 280                 285

Gln Phe Val Thr Asp Asp Gly Thr Ser Thr Gly Thr Leu Ser Glu Ile
    290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
        355                 360                 365
```

```
Met Ser Leu Trp Asp Asp Tyr Ser Val Asn Met Leu Trp Leu Asp Ser
        370             375                 380
Thr Tyr Pro Thr Asn Ala Thr Gly Thr Pro Gly Ala Ala Arg Gly Ser
385             390                 395                 400
Cys Pro Thr Thr Ser Gly Asp Pro Lys Thr Val Glu Ser Gln Asn Gly
                405                 410                 415
Ser Ser Tyr Val Thr Phe Ser Asp Ile Arg Val Gly Pro Phe Asn Ser
                420                 425                 430
Thr Phe Ser Gly Gly Ser Ser Thr Gly Gly Ser Ser Asn Thr Thr Ala
                435                 440                 445
Ser Gly Thr Thr Thr Lys Ala Ser Ser Thr Ser Thr Asn Ser Thr
450                 455                 460
Ser Thr Gly Thr Gly Val Ala Ala His Trp Gly Gln Cys Gly Gly Gln
465                 470                 475                 480
Gly Trp Thr Gly Pro Thr Thr Cys Ala Ser Gly Thr Thr Cys Thr Val
                485                 490                 495
Val Asn Pro Tyr Tyr Ser Gln Cys Leu
                500                 505

<210> SEQ ID NO 28
<211> LENGTH: 505
<212> TYPE: PRT
<213> ORGANISM: Artificial Sequence
<220> FEATURE:
<223> OTHER INFORMATION: cellobiohydrolase I with modified linker #6

<400> SEQUENCE: 28

Met Gln Gln Ile Gly Thr Tyr Thr Ala Glu Thr His Pro Ser Leu Ser
1               5                   10                  15
Trp Ser Thr Cys Lys Ser Gly Gly Ser Cys Thr Thr Asn Ser Gly Ala
                20                  25                  30
Ile Thr Leu Asp Ala Asn Trp Arg Trp Val His Gly Val Asn Thr Ser
                35                  40                  45
Thr Asn Cys Tyr Thr Gly Asn Thr Trp Asn Thr Ala Ile Cys Asp Thr
        50                  55                  60
Asp Ala Ser Cys Ala Gln Asp Cys Ala Leu Asp Gly Ala Asp Tyr Ser
65                  70                  75                  80
Gly Thr Tyr Gly Ile Thr Thr Ser Gly Asn Ser Leu Arg Leu Asn Phe
                85                  90                  95
Val Thr Gly Ser Asn Val Gly Ser Arg Thr Tyr Leu Met Ala Asp Asn
                100                 105                 110
Thr His Tyr Gln Ile Phe Asp Leu Leu Asn Gln Glu Phe Thr Phe Thr
        115                 120                 125
Val Asp Val Ser His Leu Pro Cys Gly Leu Asn Gly Ala Leu Tyr Phe
130                 135                 140
Val Thr Met Asp Ala Asp Gly Gly Val Ser Lys Tyr Pro Asn Asn Lys
145                 150                 155                 160
Ala Gly Ala Gln Tyr Gly Val Gly Tyr Cys Asp Ser Gln Cys Pro Arg
                165                 170                 175
Asp Leu Lys Phe Ile Ala Gly Gln Ala Asn Val Glu Gly Trp Thr Pro
        180                 185                 190
Ser Ser Asn Asn Ala Asn Thr Gly Leu Gly Asn His Gly Ala Cys Cys
                195                 200                 205
Ala Glu Leu Asp Ile Trp Glu Ala Asn Ser Ile Ser Glu Ala Leu Thr
        210                 215                 220
```

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
            245                 250                 255

Asp Gly Cys Asp Phe Asn Pro Tyr Arg Leu Gly Val Thr Asp Phe Tyr
        260                 265                 270

Gly Ser Gly Lys Thr Val Asp Thr Thr Lys Pro Ile Thr Val Val Thr
        275                 280                 285

Gln Phe Val Thr Asp Asp Gly Thr Ser Thr Gly Thr Leu Ser Glu Ile
    290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
                340                 345                 350

Gly Leu Ala Lys Met Gly Ala Gly Met Glu Ala Gly Met Val Leu Val
                355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Asn Gly
                405                 410                 415

Ser Ser Tyr Val Thr Phe Ser Asp Ile Arg Val Gly Pro Phe Asn Ser
                420                 425                 430

Thr Phe Ser Gly Gly Ser Ser Thr Gly Gly Ser Ser Asn Thr Thr Ala
            435                 440                 445

Ser Gly Thr Thr Thr Lys Ala Ser Ser Thr Ser Thr Asn Ser Thr
            450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
                500                 505

<210> SEQ ID NO 29
<211> LENGTH: 505
<212> TYPE: PRT
<213> ORGANISM: Artificial Sequence
<220> FEATURE:
<223> OTHER INFORMATION: cellobiohydrolase I with modified linker #5

<400> SEQUENCE: 29

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
                20                  25                  30

Ile Thr Leu Asp Ala Asn Trp Arg Trp Val His Gly Val Asn Thr Ser
            35                  40                  45

Thr Asn Cys Tyr Thr Gly Asn Thr Trp Asn Thr Ala Ile Cys Asp Thr
        50                  55                  60

Asp Ala Ser Cys Ala Gln Asp Cys Ala Leu Asp Gly Ala Asp Tyr Ser
65                  70                  75                  80

```
Gly Thr Tyr Gly Ile Thr Thr Ser Gly Asn Ser Leu Arg Leu Asn Phe
             85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
            115                 120                 125

Val Asp Val Ser His Leu Pro Cys Gly Leu Asn Gly Ala Leu Tyr Phe
130                 135                 140

Val Thr Met Asp Ala Asp Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
                180                 185                 190

Ser Ser Asn Asn Ala Asn Thr Gly Leu Gly Asn His Gly Ala Cys Cys
                195                 200                 205

Ala Glu Leu Asp Ile Trp Glu Ala Asn Ser Ile Ser Glu Ala Leu Thr
                210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
                260                 265                 270

Gly Ser Gly Lys Thr Val Asp Thr Thr Lys Pro Ile Thr Val Val Thr
                275                 280                 285

Gln Phe Val Thr Asp Asp Gly Thr Ser Thr Gly Thr Leu Ser Glu Ile
                290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
                340                 345                 350

Gly Leu Ala Lys Met Gly Ala Gly Met Glu Ala Gly Met Val Leu Val
                355                 360                 365

Met Ser Leu Trp Asp Asp Tyr Ser Val Asn Met Leu Trp Leu Asp Ser
                370                 375                 380

Thr Tyr Pro Thr Asn Ala Thr Gly Thr Pro Gly Ala Ala Arg Gly Ser
385                 390                 395                 400

Gln Pro Thr Thr Ser Gly Asp Pro Lys Thr Val Glu Ser Gln Asn Gly
                405                 410                 415

Ser Ser Tyr Val Thr Phe Ser Asp Ile Arg Val Gly Pro Phe Asn Ser
                420                 425                 430

Thr Phe Ser Gly Gly Ser Ser Thr Gly Gly Ser Ser Asn Thr Thr Ala
                435                 440                 445

Ser Gly Thr Thr Thr Thr Lys Ala Ser Ser Thr Ser Thr Ser Ser Thr
                450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
```

<210> SEQ ID NO 30
<211> LENGTH: 505
<212> TYPE: PRT
<213> ORGANISM: Artificial Sequence
<220> FEATURE:
<223> OTHER INFORMATION: cellobiohydrolase with modified linker #4

<400> SEQUENCE: 30

```
Met Gln Gln Ile Gly Thr Tyr Thr Ala Glu Thr His Pro Ser Leu Ser
1               5                   10                  15

Trp Ser Thr Cys Lys Ser Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
        275                 280                 285

Gln Phe Val Thr Asp Asp Gly Ser Thr Gly Thr Leu Ser Glu Ile
    290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
```

```
                355                 360                 365
Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Gln Pro Thr Thr Ser Gly Asp Pro Lys Thr Val Glu Ser Gln Asn Gly
                405                 410                 415

Ser Ser Tyr Val Thr Phe Ser Asp Ile Arg Val Gly Pro Phe Asn Ser
                420                 425                 430

Thr Phe Ser Gly Gly Ser Ser Thr Gly Gly Ser Ser Thr Thr Thr Ala
                435                 440                 445

Ser Gly Thr Thr Thr Lys Ala Ser Ser Thr Ser Thr Asn Ser Thr
                450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
                500                 505

<210> SEQ ID NO 31
<211> LENGTH: 505
<212> TYPE: PRT
<213> ORGANISM: Artificial Sequence
<220> FEATURE:
<223> OTHER INFORMATION: cellobiohydrolase with modified linker #3

<400> SEQUENCE: 31

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
                20                  25                  30

Ile Thr Leu Asp Ala Asn Trp Arg Trp Val His Gly Val Asn Thr Ser
                35                  40                  45

Thr Asn Cys Tyr Thr Gly Asn Thr Trp Asn Thr Ala Ile Cys Asp Thr
                50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
                100                 105                 110

Thr His Tyr Gln Ile Phe Asp Leu Leu Asn Gln Glu Phe Thr Phe Thr
                115                 120                 125

Val Asp Val Ser His Leu Pro Cys Gly Leu Asn Gly Ala Leu Tyr Phe
                130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
                180                 185                 190

Ser Ser Asn Asn Ala Asn Thr Gly Leu Gly Asn His Gly Ala Cys Cys
                195                 200                 205

Ala Glu Leu Asp Ile Trp Glu Ala Asn Ser Ile Ser Glu Ala Leu Thr
```

```
            210                 215                 220
Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
                260                 265                 270

Gly Ser Gly Lys Thr Val Asp Thr Thr Lys Pro Ile Thr Val Val Thr
            275                 280                 285

Gln Phe Val Thr Asp Asp Gly Thr Ser Thr Gly Thr Leu Ser Glu Ile
        290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
                340                 345                 350

Gly Leu Ala Lys Met Gly Ala Gly Met Glu Ala Gly Met Val Leu Val
            355                 360                 365

Met Ser Leu Trp Asp Asp Tyr Ser Val Asn Met Leu Trp Leu Asp Ser
        370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
                420                 425                 430

Thr Phe Ser Gly Gly Ser Ser Thr Gly Gly Ser Ser Thr Thr Thr Ala
            435                 440                 445

Ser Gly Thr Thr Thr Thr Lys Ala Ser Ser Thr Ser Thr Asn Ser Thr
450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
                500                 505

<210> SEQ ID NO 32
<211> LENGTH: 505
<212> TYPE: PRT
<213> ORGANISM: Artificial Sequence
<220> FEATURE:
<223> OTHER INFORMATION: cellobiohydrolase I with modified linker #2

<400> SEQUENCE: 32

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
                20                  25                  30

Ile Thr Leu Asp Ala Asn Trp Arg Trp Val His Gly Val Asn Thr Ser
            35                  40                  45

Thr Asn Cys Tyr Thr Gly Asn Thr Trp Asn Thr Ala Ile Cys Asp Thr
        50                  55                  60

Asp Ala Ser Cys Ala Gln Asp Cys Ala Leu Asp Gly Ala Asp Tyr Ser
```

```
            65                  70                  75                  80
Gly Thr Tyr Gly Ile Thr Thr Ser Gly Asn Ser Leu Arg Leu Asn Phe
                    85                  90                  95

Val Thr Gly Ser Asn Val Gly Ser Arg Thr Tyr Leu Met Ala Asp Asn
                100                 105                 110

Thr His Tyr Gln Ile Phe Asp Leu Leu Asn Gln Glu Phe Thr Phe Thr
                115                 120                 125

Val Asp Val Ser His Leu Pro Cys Gly Leu Asn Gly Ala Leu Tyr Phe
            130                 135                 140

Val Thr Met Asp Ala Asp Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
                180                 185                 190

Ser Ser Asn Asn Ala Asn Thr Gly Leu Gly Asn His Gly Ala Cys Cys
                195                 200                 205

Ala Glu Leu Asp Ile Trp Glu Ala Asn Ser Ile Ser Glu Ala Leu Thr
            210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
                260                 265                 270

Gly Ser Gly Lys Thr Val Asp Thr Thr Lys Pro Ile Thr Val Val Thr
                275                 280                 285

Gln Phe Val Thr Asp Asp Gly Thr Ser Thr Gly Thr Leu Ser Glu Ile
            290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
                340                 345                 350

Gly Leu Ala Lys Met Gly Ala Gly Met Glu Ala Gly Met Val Leu Val
            355                 360                 365

Met Ser Leu Trp Asp Asp Tyr Ser Val Asn Met Leu Trp Leu Asp Ser
    370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Ser Gly
                405                 410                 415

Ser Ser Tyr Val Thr Phe Ser Asp Ile Arg Val Gly Pro Phe Asn Ser
                420                 425                 430

Thr Phe Ser Gly Gly Ser Ser Thr Gly Gly Ser Ser Asn Thr Thr Ala
            435                 440                 445

Ser Gly Thr Thr Thr Lys Ala Ser Ser Thr Ser Ser Ser Thr
450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495
```

```
Val Asn Pro Tyr Tyr Ser Gln Cys Leu
            500                 505

<210> SEQ ID NO 33
<211> LENGTH: 505
<212> TYPE: PRT
<213> ORGANISM: Artificial Sequence
<220> FEATURE:
<223> OTHER INFORMATION: cellobiohydrolase I with modified linker #10

<400> SEQUENCE: 33

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
                20                  25                  30

Ile Thr Leu Asp Ala Asn Trp Arg Trp Val His Gly Val Asn Thr Ser
            35                  40                  45

Thr Asn Cys Tyr Thr Gly Asn Thr Trp Asn Thr Ala Ile Cys Asp Thr
        50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
                100                 105                 110

Thr His Tyr Gln Ile Phe Asp Leu Leu Asn Gln Glu Phe Thr Phe Thr
            115                 120                 125

Val Asp Val Ser His Leu Pro Cys Gly Leu Asn Gly Ala Leu Tyr Phe
        130                 135                 140

Val Thr Met Asp Ala Asp Gly Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

Ala Glu Leu Asp Ile Trp Glu Ala Asn Ser Ile Ser Glu Ala Leu Thr
210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Thr Lys Pro Ile Thr Val Val Thr
        275                 280                 285

Gln Phe Val Thr Asp Asp Gly Thr Ser Thr Gly Thr Leu Ser Glu Ile
        290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350
```

Gly Leu Ala Lys Met Gly Ala Gly Met Glu Ala Gly Met Val Leu Val
            355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Asn Pro Thr Thr Ser Gly Asp Pro Lys Thr Val Glu Ser Gln Ser Gly
            405                 410                 415

Ser Ser Tyr Val Thr Phe Ser Asp Ile Arg Val Gly Pro Phe Asn Ser
        420                 425                 430

Thr Phe Ser Gly Gly Ser Ser Thr Arg Ala Ser Pro Ser Pro Thr Gly
    435                 440                 445

Pro Thr Pro Thr Thr Lys Ala Pro Pro Gly Pro His Ser Pro Pro
450                 455                 460

Pro Thr Leu Ser Pro Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
            485                 490                 495

Val Asn Pro Tyr Tyr Ser Gln Cys Leu
        500                 505

<210> SEQ ID NO 34
<211> LENGTH: 505
<212> TYPE: PRT
<213> ORGANISM: Artificial Sequence
<220> FEATURE:
<223> OTHER INFORMATION: cellobiohydrolase I modified linker #1

<400> SEQUENCE: 34

Met Gln Gln Ile Gly Thr Tyr Thr Ala Glu Thr His Pro Ser Leu Ser
1               5                   10                  15

Trp Ser Thr Cys Lys Ser Gly Gly Ser Cys Thr Thr Asn Ser Gly Ala
            20                  25                  30

Ile Thr Leu Asp Ala Asn Trp Arg Trp Val His Gly Val Asn Thr Ser
        35                  40                  45

Thr Asn Cys Tyr Thr Gly Asn Thr Trp Asn Thr Ala Ile Cys Asp Thr
    50                  55                  60

Asp Ala Ser Cys Ala Gln Asp Cys Ala Leu Asp Gly Ala Asp Tyr Ser
65                  70                  75                  80

Gly Thr Tyr Gly Ile Thr Thr Ser Gly Asn Ser Leu Arg Leu Asn Phe
                85                  90                  95

Val Thr Gly Ser Asn Val Gly Ser Arg Thr Tyr Leu Met Ala Asp Asn
            100                 105                 110

Thr His Tyr Gln Ile Phe Asp Leu Leu Asn Gln Glu Phe Thr Phe Thr
        115                 120                 125

Val Asp Val Ser His Leu Pro Cys Gly Leu Asn Gly Ala Leu Tyr Phe
    130                 135                 140

Val Thr Met Asp Ala Asp Gly Val Ser Lys Tyr Pro Asn Asn Lys
145                 150                 155                 160

Ala Gly Ala Gln Tyr Gly Val Gly Tyr Cys Asp Ser Gln Cys Pro Arg
                165                 170                 175

Asp Leu Lys Phe Ile Ala Gly Gln Ala Asn Val Glu Gly Trp Thr Pro
            180                 185                 190

Ser Ser Asn Asn Ala Asn Thr Gly Leu Gly Asn His Gly Ala Cys Cys
        195                 200                 205

```
Ala Glu Leu Asp Ile Trp Glu Ala Asn Ser Ile Ser Glu Ala Leu Thr
    210                 215                 220

Pro His Pro Cys Asp Thr Pro Gly Leu Ser Val Cys Thr Thr Asp Ala
225                 230                 235                 240

Cys Gly Gly Thr Tyr Ser Ser Asp Arg Tyr Ala Gly Thr Cys Asp Pro
                245                 250                 255

Asp Gly Cys Asp Phe Asn Pro Tyr Arg Leu Gly Val Thr Asp Phe Tyr
            260                 265                 270

Gly Ser Gly Lys Thr Val Asp Thr Lys Pro Ile Thr Val Val Thr
        275                 280                 285

Gln Phe Val Thr Asp Asp Gly Thr Ser Thr Gly Thr Leu Ser Glu Ile
    290                 295                 300

Arg Arg Tyr Tyr Val Gln Asn Gly Val Val Ile Pro Gln Pro Ser Ser
305                 310                 315                 320

Lys Ile Ser Gly Val Ser Gly Asn Val Ile Asn Ser Asp Phe Cys Asp
                325                 330                 335

Ala Glu Ile Ser Thr Phe Gly Glu Thr Ala Ser Phe Ser Lys His Gly
            340                 345                 350

Gly Leu Ala Lys Met Gly Ala Gly Met Glu Ala Gly Met Val Leu Val
        355                 360                 365

Met Ser Leu Trp Asp Asp Tyr Ser Val Asn Met Leu Trp Leu Asp Ser
370                 375                 380

Thr Tyr Pro Thr Asn Ala Thr Gly Thr Pro Gly Ala Ala Arg Gly Ser
385                 390                 395                 400

Cys Pro Thr Thr Ser Gly Asp Pro Lys Thr Val Glu Ser Gln Asn Gly
                405                 410                 415

Ser Ser Tyr Val Thr Phe Ser Asp Ile Arg Val Gly Pro Phe Asn Ser
            420                 425                 430

Thr Phe Ser Gly Gly Ser Ser Thr Gly Gly Ser Ser Thr Thr Thr Ala
        435                 440                 445

Ser Gly Thr Thr Thr Lys Ala Ser Ser Thr Ser Thr Ser Ser Thr
450                 455                 460

Ser Thr Gly Thr Gly Val Ala Ala His Trp Gly Gln Cys Gly Gly Gln
465                 470                 475                 480

Gly Trp Thr Gly Pro Thr Thr Cys Ala Ser Gly Thr Thr Cys Thr Val
                485                 490                 495

Val Asn Pro Tyr Tyr Ser Gln Cys Leu
            500                 505

<210> SEQ ID NO 35
<211> LENGTH: 55
<212> TYPE: PRT
<213> ORGANISM: Artificial Sequence
<220> FEATURE:
<223> OTHER INFORMATION: modified linker V01

<400> SEQUENCE: 35

Cys Ser Thr Gly Ser Ala Thr Gly Thr Tyr Ser Thr Pro Thr Gly Thr
1               5                   10                  15

Ser Trp Pro Ser Thr Ser Thr Gly Thr Ala Gly Thr Thr Thr
            20                  25                  30

Ser Ala Thr Thr Thr Thr Ser Thr Ser Val Ser Ser Thr Thr Thr Thr
            35                  40                  45

Thr Thr Ser Thr Thr Ser Cys
        50                  55
```

<210> SEQ ID NO 36
<211> LENGTH: 55
<212> TYPE: PRT
<213> ORGANISM: Artificial Sequence
<220> FEATURE:
<223> OTHER INFORMATION: modified linker V06

<400> SEQUENCE: 36

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Ser Thr Ser Val Ser Ser Thr Thr Thr Thr
        35                  40                  45

Thr Thr Ser Thr Thr Ser Cys
    50                  55

<210> SEQ ID NO 37
<211> LENGTH: 54
<212> TYPE: PRT
<213> ORGANISM: Artificial Sequence
<220> FEATURE:
<223> OTHER INFORMATION: modified linker V29

<400> SEQUENCE: 37

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Ser Thr Ser Val Ser Thr Thr Thr Thr Thr
        35                  40                  45

Thr Ser Thr Thr Ser Cys
    50

<210> SEQ ID NO 38
<211> LENGTH: 54
<212> TYPE: PRT
<213> ORGANISM: Artificial Sequence
<220> FEATURE:
<223> OTHER INFORMATION: modified linker V28

<400> SEQUENCE: 38

Cys Ser Thr Gly Ser Ala Thr Gly Pro Tyr Ser Thr Pro Thr Gly Thr
1               5                   10                  15

Ser Trp Pro Ser Thr Thr Ser Gly Thr Ala Gly Thr Thr Thr Thr Ser
            20                  25                  30

Ala Thr Thr Thr Ser Thr Ser Val Ser Gly Thr Thr Thr Thr Thr Thr
        35                  40                  45

Thr Ser Thr Thr Ser Cys
    50

<210> SEQ ID NO 39
<211> LENGTH: 54
<212> TYPE: PRT
<213> ORGANISM: Artificial Sequence
<220> FEATURE:
<223> OTHER INFORMATION: modified linker V30

<400> SEQUENCE: 39

Cys Ser Thr Gly Ser Ala Thr Gly Thr Ser Thr Pro Thr Gly Thr Ser
1               5                   10                  15

Trp Pro Ser Thr Val Thr Ser Gly Thr Ala Gly Thr Thr Thr Ser
            20                  25                  30

Ala Thr Thr Thr Thr Ser Thr Ser Val Ser Gly Thr Thr Thr Thr
            35                  40                  45

Thr Ser Thr Thr Ser Cys
            50

<210> SEQ ID NO 40
<211> LENGTH: 51
<212> TYPE: PRT
<213> ORGANISM: Artificial Sequence
<220> FEATURE:
<223> OTHER INFORMATION: modified linker V08

<400> SEQUENCE: 40

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Ser Thr Thr Thr Thr Thr Thr Thr Ser Thr
            35                  40                  45

Thr Ser Cys
            50

<210> SEQ ID NO 41
<211> LENGTH: 49
<212> TYPE: PRT
<213> ORGANISM: Artificial Sequence
<220> FEATURE:
<223> OTHER INFORMATION: modified linker V09

<400> SEQUENCE: 41

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Thr Thr Thr Thr Thr Thr Ser Thr Thr Ser
            35                  40                  45

Cys

<210> SEQ ID NO 42
<211> LENGTH: 55
<212> TYPE: PRT
<213> ORGANISM: Artificial Sequence
<220> FEATURE:
<223> OTHER INFORMATION: modified linker V27

<400> SEQUENCE: 42

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Ser Thr Ser Val Ser Gly Thr Thr Thr Thr
            35                  40                  45

Thr Thr Ser Thr Thr Ser Cys
            50                  55

<210> SEQ ID NO 43
<211> LENGTH: 55
<212> TYPE: PRT

```
<213> ORGANISM: Artificial Sequence
<220> FEATURE:
<223> OTHER INFORMATION: modified linker V26

<400> SEQUENCE: 43

Cys Ser Thr Gly Ser Ala Thr Gly Pro Tyr Ser Thr Pro Thr Gly Thr
1               5                   10                  15

Ser Trp Pro Ser Thr Val Thr Ser Gly Thr Ala Gly Thr Thr Thr Thr
            20                  25                  30

Ser Ala Thr Thr Thr Thr Ser Thr Ser Val Ser Gly Thr Thr Thr Thr
        35                  40                  45

Thr Thr Ser Thr Thr Ser Cys
    50                  55

<210> SEQ ID NO 44
<211> LENGTH: 55
<212> TYPE: PRT
<213> ORGANISM: Artificial Sequence
<220> FEATURE:
<223> OTHER INFORMATION: modified linker V13

<400> SEQUENCE: 44

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Ser Thr Ser Val Ser Lys Thr Asn Thr Thr
        35                  40                  45

Thr Thr Ser Thr Thr Ser Cys
    50                  55

<210> SEQ ID NO 45
<211> LENGTH: 55
<212> TYPE: PRT
<213> ORGANISM: Artificial Sequence
<220> FEATURE:
<223> OTHER INFORMATION: modified linker V07

<400> SEQUENCE: 45

Cys Ser Thr Gly Ser Ala Thr Gly Pro Tyr Ser Thr Pro Thr Gly Thr
1               5                   10                  15

Ser Trp Pro Pro Ser Gln Thr Pro Gly Thr Ala Gly Thr Thr Thr Thr
            20                  25                  30

Ser Ala Thr Thr Thr Thr Ser Thr Ser Val Ser Ser Thr Thr Thr Thr
        35                  40                  45

Thr Thr Ser Thr Thr Ser Cys
    50                  55

<210> SEQ ID NO 46
<211> LENGTH: 51
<212> TYPE: PRT
<213> ORGANISM: Artificial Sequence
<220> FEATURE:
<223> OTHER INFORMATION: modified linker V12

<400> SEQUENCE: 46

Cys Ser Thr Gly Ser Ala Thr Gly Pro Tyr Ser Thr Pro Thr Gly Thr
1               5                   10                  15

Ser Trp Pro Ser Thr Ser Thr Ser Gly Thr Ala Gly Thr Thr Thr Thr
            20                  25                  30

Ser Ala Thr Thr Thr Thr Ser Thr Thr Ser Ser Ala Ser Thr Ser Thr
```

-continued

```
                35                  40                  45

Thr Ser Cys
    50

<210> SEQ ID NO 47
<211> LENGTH: 43
<212> TYPE: PRT
<213> ORGANISM: Artificial Sequence
<220> FEATURE:
<223> OTHER INFORMATION: modified linker V14

<400> SEQUENCE: 47

Cys Ser Thr Gly Ser Ala Thr Gly Pro Tyr Ser Thr Pro Thr Gly Thr
1               5                   10                  15

Ser Trp Pro Ser Thr Ser Thr Ser Gly Gly Val Pro Thr Pro Thr Gly
            20                  25                  30

Thr Thr Thr Thr Thr Thr Ser Thr Thr Ser Cys
        35                  40

<210> SEQ ID NO 48
<211> LENGTH: 55
<212> TYPE: PRT
<213> ORGANISM: Artificial Sequence
<220> FEATURE:
<223> OTHER INFORMATION: modified linker V10

<400> SEQUENCE: 48

Cys Ser Thr Gly Ser Ala Thr Gly Pro Tyr Ala Thr Pro Thr Asn Thr
1               5                   10                  15

Ala Trp Pro Thr Thr Thr Gln Pro Gly Thr Ala Gly Thr Thr Thr Thr
            20                  25                  30

Ser Ala Thr Thr Thr Thr Ser Thr Ser Val Ser Ser Thr Thr Thr Thr
        35                  40                  45

Thr Thr Ser Thr Thr Ser Cys
    50                  55

<210> SEQ ID NO 49
<211> LENGTH: 51
<212> TYPE: PRT
<213> ORGANISM: Artificial Sequence
<220> FEATURE:
<223> OTHER INFORMATION: modified linker V11

<400> SEQUENCE: 49

Cys Ser Thr Gly Ser Ala Thr Gly Pro Tyr Ala Thr Pro Thr Asn Thr
1               5                   10                  15

Ala Trp Pro Thr Thr Thr Gln Pro Gly Thr Ala Gly Thr Thr Thr Thr
            20                  25                  30

Ser Ala Thr Thr Thr Thr Ser Thr Thr Thr Thr Thr Thr Ser Thr
        35                  40                  45

Thr Ser Cys
    50

<210> SEQ ID NO 50
<211> LENGTH: 39
<212> TYPE: PRT
<213> ORGANISM: Artificial Sequence
<220> FEATURE:
<223> OTHER INFORMATION: modified linker V02

<400> SEQUENCE: 50

Cys Ser Thr Gly Ser Ala Thr Gly Thr Tyr Ser Thr Pro Thr Gly Thr
```

```
                1               5                  10                  15
Ser Trp Pro Pro Ser Gln Thr Pro Lys Pro Gly Val Pro Ser Gly Thr
                    20                  25                  30

Pro Tyr Thr Pro Leu Pro Cys
            35

<210> SEQ ID NO 51
<211> LENGTH: 39
<212> TYPE: PRT
<213> ORGANISM: Artificial Sequence
<220> FEATURE:
<223> OTHER INFORMATION: modified linker V03

<400> SEQUENCE: 51

Cys Ser Thr Gly Ser Ala Thr Gly Thr Tyr Ser Thr Pro Thr Gly Thr
1               5                   10                  15

Ser Trp Pro Pro Ser Gln Thr Pro Ser Pro Gly Val Pro Ser Gly Thr
                    20                  25                  30

Pro Ser Thr Pro Leu Pro Cys
            35

<210> SEQ ID NO 52
<211> LENGTH: 39
<212> TYPE: PRT
<213> ORGANISM: Artificial Sequence
<220> FEATURE:
<223> OTHER INFORMATION: modified linker V20

<400> SEQUENCE: 52

Cys Ser Thr Gly Ser Ala Thr Gly Thr Tyr Ser Thr Pro Thr Gly Thr
1               5                   10                  15

Ser Trp Pro Pro Ser Gln Thr Pro Ser Pro Gly Val Pro Ser Gly Thr
                    20                  25                  30

Pro Ser Thr Pro Ser Pro Cys
            35

<210> SEQ ID NO 53
<211> LENGTH: 39
<212> TYPE: PRT
<213> ORGANISM: Artificial Sequence
<220> FEATURE:
<223> OTHER INFORMATION: modified linker V21

<400> SEQUENCE: 53

Cys Ser Thr Gly Ser Ala Thr Gly Thr Ser Ser Thr Pro Thr Gly Thr
1               5                   10                  15

Ser Trp Pro Pro Ser Gln Thr Pro Ser Pro Gly Val Pro Ser Gly Thr
                    20                  25                  30

Pro Ser Thr Pro Ser Pro Cys
            35

<210> SEQ ID NO 54
<211> LENGTH: 56
<212> TYPE: PRT
<213> ORGANISM: Artificial Sequence
<220> FEATURE:
<223> OTHER INFORMATION: modified linker V22

<400> SEQUENCE: 54

Cys Ser Thr Gly Ser Ala Thr Gly Thr Ser Ser Thr Pro Thr Gly Thr
1               5                   10                  15

Ser Trp Pro Thr Lys Ser Pro Thr Thr Thr Thr Ala Thr Ala Thr Thr
```

```
                    20                  25                  30

Thr Thr Ala Pro Ser Thr Ser Thr Thr Pro Pro Ser Ser Glu Pro
            35                  40                  45

Ala Thr Phe Pro Thr Gly Asn Cys
    50                  55

<210> SEQ ID NO 55
<211> LENGTH: 56
<212> TYPE: PRT
<213> ORGANISM: Artificial Sequence
<220> FEATURE:
<223> OTHER INFORMATION: modified linker V23

<400> SEQUENCE: 55

Cys Ser Thr Gly Ser Ala Thr Gly Thr Ser Ser Thr Pro Thr Gly Thr
1               5                   10                  15

Ser Trp Pro Thr Ser Ser Pro Thr Thr Thr Ala Thr Ala Thr Thr
            20                  25                  30

Thr Thr Ala Pro Ser Thr Ser Thr Thr Pro Pro Ser Ser Thr Pro
            35                  40                  45

Ala Thr Phe Pro Thr Gly Asn Cys
    50                  55

<210> SEQ ID NO 56
<211> LENGTH: 47
<212> TYPE: PRT
<213> ORGANISM: Artificial Sequence
<220> FEATURE:
<223> OTHER INFORMATION: modified linker V24

<400> SEQUENCE: 56

Cys Ser Thr Gly Ser Ala Thr Gly Thr Ser Ser Thr Pro Thr Gly Thr
1               5                   10                  15

Ser Trp Pro Thr Ser Ser Pro Thr Thr Thr Thr Ala Thr Ser Thr Thr
            20                  25                  30

Pro Pro Ser Ser Ser Thr Pro Ala Thr Phe Pro Thr Gly Asn Cys
            35                  40                  45

<210> SEQ ID NO 57
<211> LENGTH: 43
<212> TYPE: PRT
<213> ORGANISM: Artificial Sequence
<220> FEATURE:
<223> OTHER INFORMATION: modified linker V24

<400> SEQUENCE: 57

Cys Ser Thr Gly Ser Ala Thr Gly Thr Ser Ser Thr Pro Thr Gly Thr
1               5                   10                  15

Ser Trp Pro Thr Ser Ser Pro Thr Thr Ser Thr Thr Pro Pro Ser Ser
            20                  25                  30

Ser Thr Pro Ala Thr Phe Pro Thr Gly Asn Cys
            35                  40

<210> SEQ ID NO 58
<211> LENGTH: 55
<212> TYPE: PRT
<213> ORGANISM: Artificial Sequence
<220> FEATURE:
<223> OTHER INFORMATION: modified linker V31

<400> SEQUENCE: 58

Cys Ser Ala Thr Ser Ala Thr Gly Pro Tyr Ala Thr Pro Thr Asn Thr
```

```
                1               5                  10                 15
Ala Trp Pro Ser Thr Val Thr Ser Gly Thr Ala Gly Thr Thr Thr
                20                 25                 30

Ser Ala Thr Thr Thr Thr Ser Thr Ser Val Ser Gly Thr Thr Gln
        35                 40                 45

Pro Pro Glu Arg Pro Ala Cys
        50                 55

<210> SEQ ID NO 59
<211> LENGTH: 29
<212> TYPE: PRT
<213> ORGANISM: Artificial Sequence
<220> FEATURE:
<223> OTHER INFORMATION: modified linker V32

<400> SEQUENCE: 59

Cys Ser Ala Thr Ser Ala Thr Gly Pro Tyr Ala Thr Pro Thr Asn Thr
1               5                  10                 15

Ala Trp Thr Thr Thr Gln Pro Pro Glu Arg Pro Ala Cys
        20                 25

<210> SEQ ID NO 60
<211> LENGTH: 34
<212> TYPE: PRT
<213> ORGANISM: Artificial Sequence
<220> FEATURE:
<223> OTHER INFORMATION: modified linker V33

<400> SEQUENCE: 60

Cys Ser Ala Thr Ser Ala Thr Gly Pro Tyr Ala Thr Pro Thr Asn Thr
1               5                  10                 15

Ala Trp Gly Gly Gly Gly Ser Thr Thr Thr Gln Pro Pro Glu Arg Pro
        20                 25                 30

Ala Cys

<210> SEQ ID NO 61
<211> LENGTH: 39
<212> TYPE: PRT
<213> ORGANISM: Artificial Sequence
<220> FEATURE:
<223> OTHER INFORMATION: modified linker V34

<400> SEQUENCE: 61

Cys Ser Ala Thr Ser Ala Thr Gly Pro Tyr Ala Thr Pro Thr Asn Thr
1               5                  10                 15

Ala Trp Gly Gly Gly Gly Ser Gly Gly Gly Gly Ser Thr Thr Thr Gln
        20                 25                 30

Pro Pro Glu Arg Pro Ala Cys
        35

<210> SEQ ID NO 62
<211> LENGTH: 43
<212> TYPE: PRT
<213> ORGANISM: Artificial Sequence
<220> FEATURE:
<223> OTHER INFORMATION: modified linker V35

<400> SEQUENCE: 62

Cys Ser Ala Thr Ser Ala Thr Gly Pro Tyr Ala Thr Pro Thr Asn Thr
1               5                  10                 15

Ala Trp Gly Thr Ala Gly Val Pro Thr Pro Thr Gly Pro Thr Pro Thr
        20                 25                 30
```

```
Thr Thr Thr Gln Pro Pro Glu Arg Pro Ala Cys
         35                  40

<210> SEQ ID NO 63
<211> LENGTH: 35
<212> TYPE: PRT
<213> ORGANISM: Artificial Sequence
<220> FEATURE:
<223> OTHER INFORMATION: modified linker V04

<400> SEQUENCE: 63

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Ser Gly Gly Gly
            20                  25                  30

Gly Ser Cys
        35

<210> SEQ ID NO 64
<211> LENGTH: 40
<212> TYPE: PRT
<213> ORGANISM: Artificial Sequence
<220> FEATURE:
<223> OTHER INFORMATION: modified linker V05

<400> SEQUENCE: 64

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Cys
        35                  40

<210> SEQ ID NO 65
<211> LENGTH: 45
<212> TYPE: PRT
<213> ORGANISM: Artificial Sequence
<220> FEATURE:
<223> OTHER INFORMATION: modified linker V15

<400> SEQUENCE: 65

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Gly Gly Gly Ser Cys
        35                  40                  45

<210> SEQ ID NO 66
<211> LENGTH: 51
<212> TYPE: PRT
<213> ORGANISM: Artificial Sequence
<220> FEATURE:
<223> OTHER INFORMATION: modified linker V16

<400> SEQUENCE: 66

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Gly Gly Gly Ser Ser Gly Gly Gly
        35                  40                  45
```

```
Gly Ser Cys
     50

<210> SEQ ID NO 67
<211> LENGTH: 47
<212> TYPE: PRT
<213> ORGANISM: Artificial Sequence
<220> FEATURE:
<223> OTHER INFORMATION: modified linker V17

<400> SEQUENCE: 67

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Ala Thr Phe Pro Thr Gly Asn Cys
        35                  40                  45

<210> SEQ ID NO 68
<211> LENGTH: 47
<212> TYPE: PRT
<213> ORGANISM: Artificial Sequence
<220> FEATURE:
<223> OTHER INFORMATION: modified linker V18

<400> SEQUENCE: 68

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Gly Asn Ser Thr Ile Ser Ser Cys
        35                  40                  45

<210> SEQ ID NO 69
<211> LENGTH: 54
<212> TYPE: PRT
<213> ORGANISM: Artificial Sequence
<220> FEATURE:
<223> OTHER INFORMATION: modified linker V19

<400> SEQUENCE: 69

Cys Ser Thr Gly Ser Ala Thr Gly Thr Tyr Ser Thr Pro Thr Gly Thr
1               5                   10                  15

Ser Trp Pro Gly Gly Gly Gly Ser Gly Gly Gly Gly Ser Gly Gly Gly
            20                  25                  30

Gly Ser Gly Gly Gly Gly Ser Gly Asn Ser Thr Ile Ser Ser Ala Thr
        35                  40                  45

Phe Pro Thr Gly Asn Cys
     50
```